US010828065B2

(12) United States Patent
Holsten

(10) Patent No.: US 10,828,065 B2
(45) Date of Patent: Nov. 10, 2020

(54) SURGICAL ACCESS SYSTEM

(71) Applicant: Covidien LP, Mansfield, MA (US)

(72) Inventor: Henry E. Holsten, Hamden, CT (US)

(73) Assignee: COVIDIEN LP, Mansfield, MA (US)

( * ) Notice: Subject to any disclaimer, the term of this patent is extended or adjusted under 35 U.S.C. 154(b) by 171 days.

(21) Appl. No.: 16/043,907

(22) Filed: Jul. 24, 2018

(65) Prior Publication Data

US 2019/0059944 A1    Feb. 28, 2019

Related U.S. Application Data

(60) Provisional application No. 62/550,783, filed on Aug. 28, 2017.

(51) Int. Cl.
*A61B 17/34* (2006.01)
*A61B 17/02* (2006.01)
*A61B 17/00* (2006.01)

(52) U.S. Cl.
CPC ...... *A61B 17/3462* (2013.01); *A61B 17/3417* (2013.01); *A61B 17/3423* (2013.01); *A61B 17/3474* (2013.01); *A61B 17/3498* (2013.01); *A61B 17/0281* (2013.01); *A61B 2017/00902* (2013.01); *A61B 2017/3433* (2013.01); *A61B 2017/3445* (2013.01); *A61B 2017/3454* (2013.01); *A61B 2017/3456* (2013.01)

(58) Field of Classification Search
CPC ..... A61M 13/00; A61B 17/34; A61B 17/3421
See application file for complete search history.

(56) References Cited

U.S. PATENT DOCUMENTS

| | | | |
|---|---|---|---|
| 3,402,710 | A | 9/1968 | Paleschuck |
| 3,495,586 | A | 2/1970 | Regenbogen |
| 4,016,884 | A | 4/1977 | Kwan-Gett |
| 4,112,932 | A | 9/1978 | Chiulli |
| 4,183,357 | A | 1/1980 | Bentley et al. |
| 4,356,826 | A | 11/1982 | Kubota |
| 4,402,683 | A | 9/1983 | Kopman |
| 4,653,476 | A | 3/1987 | Bonnet |
| 4,737,148 | A | 4/1988 | Blake |
| 4,863,430 | A | 9/1989 | Klyce et al. |

(Continued)

FOREIGN PATENT DOCUMENTS

| | | |
|---|---|---|
| CA | 2702419 A1 | 11/2010 |
| CN | 103083064 A | 5/2013 |

(Continued)

OTHER PUBLICATIONS

Extended European Search Report issued in European Application No. 18190660.3 dated Dec. 13, 2018.

*Primary Examiner* — Laura A Bouchelle

(74) *Attorney, Agent, or Firm* — Carter, DeLuca & Farrell LLP

(57) ABSTRACT

A surgical access system includes a cannula assembly and an obturator assembly. The obturator assembly provides an insufflation channel or fluid passage for delivery of insufflation fluids directly to an underlying cavity, e.g., the abdominal cavity. The fluid passage is completely confined within the obturator assembly isolated from the cannula assembly and terminates at a location distal of the cannula assembly such that the insufflation fluids released from the fluid passage are directed toward the abdominal cavity and not within the cannula assembly.

20 Claims, 48 Drawing Sheets

(56) References Cited

U.S. PATENT DOCUMENTS

| | | |
|---|---|---|
| 4,863,438 A | 9/1989 | Gauderer et al. |
| 4,984,564 A | 1/1991 | Yuen |
| 5,002,557 A | 3/1991 | Hasson |
| 5,073,169 A | 12/1991 | Raiken |
| 5,082,005 A | 1/1992 | Kaldany |
| 5,122,122 A | 6/1992 | Allgood |
| 5,159,921 A | 11/1992 | Hoover |
| 5,176,697 A | 1/1993 | Hasson et al. |
| 5,183,471 A | 2/1993 | Wilk |
| 5,192,301 A | 3/1993 | Kamiya et al. |
| 5,209,741 A | 5/1993 | Spaeth |
| 5,209,754 A | 5/1993 | Ahluwalia |
| 5,217,466 A | 6/1993 | Hasson |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,269,772 A | 12/1993 | Wilk |
| 5,290,249 A | 3/1994 | Foster et al. |
| 5,312,391 A | 5/1994 | Wilk |
| 5,312,417 A | 5/1994 | Wilk |
| 5,314,417 A | 5/1994 | Stephens et al. |
| 5,318,516 A | 6/1994 | Cosmescu |
| 5,330,486 A | 7/1994 | Wilk |
| 5,334,143 A | 8/1994 | Carroll |
| 5,336,169 A | 8/1994 | Divilio et al. |
| 5,336,203 A | 8/1994 | Goldhardt et al. |
| 5,337,937 A | 8/1994 | Remiszewski et al. |
| 5,345,927 A | 9/1994 | Bonutti |
| 5,360,417 A | 11/1994 | Gravener et al. |
| 5,366,478 A | 11/1994 | Brinkerhoff et al. |
| 5,375,588 A | 12/1994 | Yoon |
| 5,378,588 A | 1/1995 | Tsuchiya |
| 5,391,156 A | 2/1995 | Hildwein et al. |
| 5,394,863 A | 3/1995 | Sanford et al. |
| 5,395,367 A | 3/1995 | Wilk |
| 5,437,683 A | 8/1995 | Neumann et al. |
| 5,445,615 A | 8/1995 | Yoon |
| 5,451,222 A | 9/1995 | De Maagd et al. |
| 5,460,170 A | 10/1995 | Hammerslag |
| 5,464,409 A | 11/1995 | Mohajer |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,514,153 A | 5/1996 | Bonutti |
| 5,520,698 A | 5/1996 | Koh |
| 5,522,791 A | 6/1996 | Leyva |
| 5,524,644 A | 6/1996 | Crook |
| 5,540,648 A | 7/1996 | Yoon |
| 5,545,150 A | 8/1996 | Danks et al. |
| 5,545,179 A | 8/1996 | Williamson, IV |
| 5,556,385 A | 9/1996 | Andersen |
| 5,569,159 A | 10/1996 | Anderson et al. |
| 5,577,993 A | 11/1996 | Zhu et al. |
| 5,601,581 A | 2/1997 | Fogarty et al. |
| 5,624,399 A | 4/1997 | Ackerman |
| 5,634,911 A | 6/1997 | Hermann et al. |
| 5,634,937 A | 6/1997 | Mollenauer et al. |
| 5,643,285 A | 7/1997 | Rowden et al. |
| 5,649,550 A | 7/1997 | Crook |
| 5,651,771 A | 7/1997 | Tangherlini et al. |
| 5,653,705 A | 8/1997 | de la Torre et al. |
| 5,656,013 A | 8/1997 | Yoon |
| 5,672,168 A | 9/1997 | de la Torre et al. |
| 5,683,378 A | 11/1997 | Christy |
| 5,685,857 A | 11/1997 | Negus et al. |
| 5,697,946 A | 12/1997 | Hopper et al. |
| 5,709,675 A | 1/1998 | Williams |
| 5,713,858 A | 2/1998 | Heruth et al. |
| 5,713,869 A | 2/1998 | Morejon |
| 5,722,962 A | 3/1998 | Garcia |
| 5,728,103 A | 3/1998 | Picha et al. |
| 5,730,748 A | 3/1998 | Fogarty et al. |
| 5,735,791 A | 4/1998 | Alexander, Jr. et al. |
| 5,741,298 A | 4/1998 | MacLeod |
| 5,752,970 A | 5/1998 | Yoon |
| 5,782,817 A | 7/1998 | Franzel et al. |
| 5,795,290 A | 8/1998 | Bridges |
| 5,803,921 A | 9/1998 | Bonadio |
| 5,810,712 A | 9/1998 | Dunn |
| 5,813,409 A | 9/1998 | Leahy et al. |
| 5,830,191 A | 11/1998 | Hildwein et al. |
| 5,836,871 A | 11/1998 | Wallace et al. |
| 5,836,913 A | 11/1998 | Orth et al. |
| 5,840,077 A | 11/1998 | Rowden et al. |
| 5,842,971 A | 12/1998 | Yoon |
| 5,848,992 A | 12/1998 | Hart et al. |
| 5,853,417 A | 12/1998 | Fogarty et al. |
| 5,857,461 A | 1/1999 | Levitsky et al. |
| 5,865,817 A | 2/1999 | Moenning et al. |
| 5,871,474 A | 2/1999 | Hermann et al. |
| 5,876,413 A | 3/1999 | Fogarty et al. |
| 5,894,843 A | 4/1999 | Benetti et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,914,415 A | 6/1999 | Tago |
| 5,916,198 A | 6/1999 | Dillow |
| 5,941,898 A | 8/1999 | Moenning et al. |
| 5,951,588 A | 9/1999 | Moenning |
| 5,957,913 A | 9/1999 | de la Torre et al. |
| 5,964,781 A | 10/1999 | Mollenauer et al. |
| 5,976,174 A | 11/1999 | Ruiz |
| 5,997,515 A | 12/1999 | de la Torre et al. |
| 6,017,355 A | 1/2000 | Hessel et al. |
| 6,018,094 A | 1/2000 | Fox |
| 6,024,736 A | 2/2000 | de la Torre et al. |
| 6,030,402 A | 2/2000 | Thompson et al. |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,068,639 A | 5/2000 | Fogarty et al. |
| 6,077,288 A | 6/2000 | Shimomura et al. |
| 6,086,603 A | 7/2000 | Termin et al. |
| 6,099,506 A | 8/2000 | Macoviak et al. |
| 6,110,154 A | 8/2000 | Shimomura et al. |
| 6,142,936 A | 11/2000 | Beane et al. |
| 6,156,006 A | 12/2000 | Brosens et al. |
| 6,162,196 A | 12/2000 | Hart et al. |
| 6,171,282 B1 | 1/2001 | Ragsdale |
| 6,197,002 B1 | 3/2001 | Peterson |
| 6,217,555 B1 | 4/2001 | Hart et al. |
| 6,228,063 B1 | 5/2001 | Aboul-Hosn |
| 6,234,958 B1 | 5/2001 | Snoke et al. |
| 6,238,373 B1 | 5/2001 | de la Torre et al. |
| 6,241,768 B1 | 6/2001 | Agarwal et al. |
| 6,251,119 B1 | 6/2001 | Addis |
| 6,254,534 B1 | 7/2001 | Butler et al. |
| 6,264,604 B1 | 7/2001 | Kieturakis et al. |
| 6,276,661 B1 | 8/2001 | Laird |
| 6,293,952 B1 | 9/2001 | Brosens et al. |
| 6,315,770 B1 | 11/2001 | de la Torre et al. |
| 6,319,246 B1 | 11/2001 | de la Torre et al. |
| 6,328,720 B1 | 12/2001 | McNally et al. |
| 6,329,637 B1 | 12/2001 | Hembree et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,485,410 B1 | 11/2002 | Loy |
| 6,488,620 B1 | 12/2002 | Segermark et al. |
| 6,488,692 B1 | 12/2002 | Spence et al. |

(56) References Cited

U.S. PATENT DOCUMENTS

| | | |
|---|---|---|
| 6,524,283 B1 | 2/2003 | Hopper et al. |
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,558,371 B2 | 5/2003 | Dorn |
| 6,562,022 B2 | 5/2003 | Hoste et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,684,405 B2 | 2/2004 | Lezdey |
| 6,706,050 B1 | 3/2004 | Giannadakis |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,493,703 B2 | 2/2009 | Kim et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,753,901 B2 | 7/2010 | Piskun et al. |
| 7,758,500 B2 | 7/2010 | Boyd et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 | 12/2010 | Piskun |
| 7,850,667 B2 | 12/2010 | Gresham |
| 7,867,164 B2 | 1/2011 | Butler et al. |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,913,697 B2 | 3/2011 | Nguyen et al. |
| 7,951,076 B2 | 5/2011 | Hart et al. |
| 7,955,257 B2 | 6/2011 | Frasier et al. |
| 7,955,313 B2 | 6/2011 | Boismier |
| 7,998,068 B2 | 8/2011 | Bonadio et al. |
| 8,021,296 B2 | 9/2011 | Bonadio et al. |
| 8,025,670 B2 | 9/2011 | Sharp et al. |
| 8,038,652 B2 | 10/2011 | Morrison et al. |
| 8,066,673 B2 | 11/2011 | Hart et al. |
| 8,079,986 B2 | 12/2011 | Taylor et al. |
| 8,092,430 B2 | 1/2012 | Richard et al. |
| 8,105,234 B2 | 1/2012 | Ewers et al. |
| 8,109,873 B2 | 2/2012 | Albrecht et al. |
| 8,157,786 B2 | 4/2012 | Miller et al. |
| 8,157,817 B2 | 4/2012 | Bonadio et al. |
| 8,187,177 B2 | 5/2012 | Kahle et al. |
| 8,187,178 B2 | 5/2012 | Bonadio et al. |
| 8,241,209 B2 | 8/2012 | Shelton, IV et al. |
| 8,262,568 B2 | 9/2012 | Albrecht et al. |
| 8,323,184 B2 | 12/2012 | Spiegal et al. |
| 8,335,783 B2 | 12/2012 | Milby |
| 8,343,047 B2 | 1/2013 | Albrecht et al. |
| 8,353,824 B2 | 1/2013 | Shelton, IV et al. |
| 8,403,889 B2 | 3/2013 | Richard |
| 8,480,683 B2 | 7/2013 | Fowler et al. |
| 8,574,153 B2 | 11/2013 | Richard |
| 8,585,632 B2 | 11/2013 | Okoniewski |
| 9,155,558 B2 | 10/2015 | Albrecht et al. |
| 2001/0037053 A1 | 11/2001 | Bonadio et al. |
| 2002/0055714 A1 | 5/2002 | Rothschild |
| 2003/0014076 A1 | 1/2003 | Mollenauer et al. |
| 2003/0093104 A1 | 5/2003 | Bonner et al. |

(56) References Cited

U.S. PATENT DOCUMENTS

| | | |
|---|---|---|
| 2003/0187376 A1 | 10/2003 | Rambo |
| 2003/0233115 A1 | 12/2003 | Eversull et al. |
| 2003/0236549 A1 | 12/2003 | Bonadio et al. |
| 2004/0059297 A1 | 3/2004 | Racenet et al. |
| 2004/0092795 A1 | 5/2004 | Bonadio et al. |
| 2004/0102804 A1 | 5/2004 | Chin |
| 2004/0111061 A1 | 6/2004 | Curran |
| 2004/0138529 A1 | 7/2004 | Wiltshire et al. |
| 2004/0204734 A1 | 10/2004 | Wagner et al. |
| 2004/0267096 A1 | 12/2004 | Caldwell et al. |
| 2005/0020884 A1 | 1/2005 | Hart et al. |
| 2005/0070935 A1 | 3/2005 | Ortiz |
| 2005/0096695 A1 | 5/2005 | Olich |
| 2005/0119525 A1 | 6/2005 | Takemoto |
| 2005/0119613 A1* | 6/2005 | Moenning ............ A61M 31/00 604/93.01 |
| 2005/0137459 A1 | 6/2005 | Chin et al. |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0209608 A1 | 9/2005 | O'Heeron |
| 2005/0245876 A1 | 11/2005 | Khosravi et al. |
| 2005/0251092 A1 | 11/2005 | Howell et al. |
| 2005/0277946 A1 | 12/2005 | Greenhalgh |
| 2006/0071432 A1 | 4/2006 | Staudner |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0212063 A1 | 9/2006 | Wilk |
| 2006/0224161 A1 | 10/2006 | Bhattacharyya |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0270911 A1 | 11/2006 | Voegele et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0203398 A1 | 8/2007 | Bonadio et al. |
| 2007/0208312 A1 | 9/2007 | Norton et al. |
| 2007/0225650 A1 | 9/2007 | Hart et al. |
| 2007/0270654 A1 | 11/2007 | Pignato et al. |
| 2007/0270882 A1 | 11/2007 | Hjelle et al. |
| 2008/0009826 A1 | 1/2008 | Miller et al. |
| 2008/0021360 A1 | 1/2008 | Fihe et al. |
| 2008/0027476 A1 | 1/2008 | Piskun |
| 2008/0048011 A1 | 2/2008 | Weller |
| 2008/0091143 A1 | 4/2008 | Taylor et al. |
| 2008/0097162 A1 | 4/2008 | Bonadio et al. |
| 2008/0097332 A1 | 4/2008 | Greenhalgh et al. |
| 2008/0119868 A1 | 5/2008 | Sharp et al. |
| 2008/0161826 A1 | 7/2008 | Guiraudon |
| 2008/0188868 A1 | 8/2008 | Weitzner et al. |
| 2008/0194973 A1 | 8/2008 | Imam |
| 2008/0200767 A1 | 8/2008 | Ewers et al. |
| 2008/0249556 A1 | 10/2008 | Yamatani |
| 2008/0255519 A1 | 10/2008 | Piskun et al. |
| 2008/0319261 A1 | 12/2008 | Lucini et al. |
| 2009/0012477 A1 | 1/2009 | Norton et al. |
| 2009/0036738 A1 | 2/2009 | Cuschieri et al. |
| 2009/0036745 A1 | 2/2009 | Bonadio et al. |
| 2009/0093752 A1 | 4/2009 | Richard et al. |
| 2009/0093850 A1 | 4/2009 | Richard |
| 2009/0105635 A1 | 4/2009 | Bettuchi et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0221968 A1 | 9/2009 | Morrison et al. |
| 2009/0227843 A1 | 9/2009 | Smith et al. |
| 2009/0326330 A1 | 12/2009 | Bonadio et al. |
| 2009/0326332 A1 | 12/2009 | Carter |
| 2010/0063452 A1 | 3/2010 | Edelman et al. |
| 2010/0100043 A1 | 4/2010 | Racenet |
| 2010/0113886 A1 | 5/2010 | Piskun et al. |
| 2010/0228094 A1 | 9/2010 | Ortiz et al. |
| 2010/0240960 A1 | 9/2010 | Richard |
| 2010/0249516 A1 | 9/2010 | Shelton, IV et al. |
| 2010/0249523 A1 | 9/2010 | Spiegal et al. |
| 2010/0249524 A1 | 9/2010 | Ransden et al. |
| 2010/0262080 A1 | 10/2010 | Shelton, IV et al. |
| 2010/0280326 A1 | 11/2010 | Hess et al. |
| 2010/0286484 A1 | 11/2010 | Stellon et al. |
| 2010/0286506 A1 | 11/2010 | Ransden et al. |
| 2010/0298646 A1 | 11/2010 | Stellon et al. |
| 2010/0312063 A1 | 12/2010 | Hess et al. |
| 2011/0009704 A1 | 1/2011 | Marczyk et al. |
| 2011/0021877 A1 | 1/2011 | Fortier et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0087159 A1* | 4/2011 | Parihar ................. A61B 17/34 604/26 |
| 2011/0118553 A1 | 5/2011 | Stopek |
| 2011/0124968 A1 | 5/2011 | Kleyman |
| 2011/0124969 A1 | 5/2011 | Stopek |
| 2011/0124970 A1 | 5/2011 | Kleyman |
| 2011/0125186 A1 | 5/2011 | Fowler et al. |
| 2011/0166423 A1 | 7/2011 | Farascioni et al. |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0313250 A1 | 12/2011 | Kleyman |
| 2012/0059640 A1 | 3/2012 | Roy et al. |
| 2012/0123202 A1* | 5/2012 | Albrecht ............ A61B 17/3417 600/104 |
| 2012/0130177 A1 | 5/2012 | Davis |
| 2012/0130181 A1 | 5/2012 | Davis |
| 2012/0130182 A1 | 5/2012 | Rodrigues, Jr. et al. |
| 2012/0130183 A1 | 5/2012 | Barnes |
| 2012/0130184 A1 | 5/2012 | Richard |
| 2012/0130185 A1 | 5/2012 | Pribanic |
| 2012/0130186 A1 | 5/2012 | Stopek et al. |
| 2012/0130187 A1 | 5/2012 | Okoniewski |
| 2012/0130188 A1 | 5/2012 | Okoniewski |
| 2012/0130190 A1 | 5/2012 | Kasvikis |
| 2012/0130191 A1 | 5/2012 | Pribanic |
| 2012/0149987 A1 | 6/2012 | Richard et al. |
| 2012/0157777 A1 | 6/2012 | Okoniewski |
| 2012/0157779 A1 | 6/2012 | Fischvogt |
| 2012/0157780 A1 | 6/2012 | Okoniewski et al. |
| 2012/0157781 A1 | 6/2012 | Kleyman |
| 2012/0157782 A1 | 6/2012 | Alfieri |
| 2012/0157783 A1 | 6/2012 | Okoniewski et al. |
| 2012/0157784 A1 | 6/2012 | Kleyman et al. |
| 2012/0157785 A1 | 6/2012 | Kleyman |
| 2012/0157786 A1 | 6/2012 | Pribanic |
| 2012/0190931 A1 | 7/2012 | Stopek |
| 2012/0190932 A1 | 7/2012 | Okoniewski |
| 2012/0190933 A1 | 7/2012 | Kleyman |
| 2012/0209077 A1 | 8/2012 | Racenet |
| 2012/0209078 A1 | 8/2012 | Pribanic et al. |
| 2012/0245427 A1 | 9/2012 | Kleyman |
| 2012/0245429 A1 | 9/2012 | Smith |
| 2012/0245430 A1 | 9/2012 | Kleyman et al. |
| 2012/0283520 A1 | 11/2012 | Kleyman |
| 2013/0225930 A1 | 8/2013 | Smith |
| 2013/0225931 A1 | 8/2013 | Cruz et al. |
| 2013/0245373 A1 | 9/2013 | Okoniewski |
| 2013/0274559 A1 | 10/2013 | Fowler et al. |

(56) References Cited

U.S. PATENT DOCUMENTS

| | | |
|---|---|---|
| 2013/0310651 A1 | 11/2013 | Alfieri |
| 2014/0018632 A1 | 1/2014 | Kleyman |
| 2018/0021063 A1* | 1/2018 | Main .................. A61B 17/3498 604/167.01 |

FOREIGN PATENT DOCUMENTS

| | | |
|---|---|---|
| EP | 0226026 A2 | 6/1987 |
| EP | 0538060 A1 | 4/1993 |
| EP | 0577400 A1 | 1/1994 |
| EP | 0630660 A1 | 12/1994 |
| EP | 0807416 A2 | 11/1997 |
| EP | 0950376 A1 | 10/1999 |
| EP | 1188415 A2 | 3/2002 |
| EP | 1312318 A1 | 5/2003 |
| EP | 1774918 A1 | 4/2007 |
| EP | 1932485 A1 | 6/2008 |
| EP | 2044889 A1 | 4/2009 |
| EP | 2044897 A1 | 4/2009 |
| EP | 2080494 A1 | 7/2009 |
| EP | 2095781 A2 | 9/2009 |
| EP | 2098182 A2 | 9/2009 |
| EP | 2138117 A1 | 12/2009 |
| EP | 2138118 A2 | 12/2009 |
| EP | 2181657 A2 | 5/2010 |
| EP | 2226025 A1 | 9/2010 |
| EP | 2229900 A1 | 9/2010 |
| EP | 2238924 A1 | 10/2010 |
| EP | 2238925 A1 | 10/2010 |
| EP | 2238926 A2 | 10/2010 |
| EP | 2238933 A1 | 10/2010 |
| EP | 2248478 A1 | 11/2010 |
| EP | 2248482 A1 | 11/2010 |
| EP | 2253283 A1 | 11/2010 |
| EP | 2272450 A2 | 1/2011 |
| EP | 2277464 A1 | 1/2011 |
| EP | 2289438 A1 | 3/2011 |
| EP | 2292165 | 3/2011 |
| EP | 2343019 | 7/2011 |
| EP | 3360494 A1 | 8/2018 |
| GB | 2469083 | 4/2009 |
| WO | 8401512 | 4/1984 |
| WO | 9314801 | 8/1993 |
| WO | 9404067 | 3/1994 |
| WO | 9601132 A1 | 1/1996 |
| WO | 9610963 | 4/1996 |
| WO | 9636283 | 11/1996 |
| WO | 9733520 | 9/1997 |
| WO | 9742889 | 11/1997 |
| WO | 9916368 | 4/1999 |
| WO | 9922804 | 5/1999 |
| WO | 9929250 | 6/1999 |
| WO | 0032116 | 6/2000 |
| WO | 0032120 | 6/2000 |
| WO | 0054675 | 9/2000 |
| WO | 0108581 | 2/2001 |
| WO | 0149363 | 7/2001 |
| WO | 0207611 | 1/2002 |
| WO | 03034908 A2 | 5/2003 |
| WO | 03071926 | 9/2003 |
| WO | 03077726 | 9/2003 |
| WO | 2004043275 | 5/2004 |
| WO | 2004054456 | 7/2004 |
| WO | 2004075741 | 9/2004 |
| WO | 2004075930 | 9/2004 |
| WO | 2005058409 | 6/2005 |
| WO | 2006019723 | 2/2006 |
| WO | 2006100658 A2 | 9/2006 |
| WO | 2006110733 | 10/2006 |
| WO | 2007018458 | 2/2007 |
| WO | 2007095703 | 8/2007 |
| WO | 2007143200 | 12/2007 |
| WO | 2008015566 A2 | 2/2008 |
| WO | 2008042005 | 4/2008 |
| WO | 2008043100 A2 | 4/2008 |
| WO | 2008077080 | 6/2008 |
| WO | 2008093313 | 8/2008 |
| WO | 2008103151 | 8/2008 |
| WO | 2008121294 A1 | 10/2008 |
| WO | 2008147644 | 12/2008 |
| WO | 2009036343 | 3/2009 |
| WO | 2010000047 | 1/2010 |
| WO | 2010141409 | 12/2010 |
| WO | 2010141673 | 12/2010 |

* cited by examiner

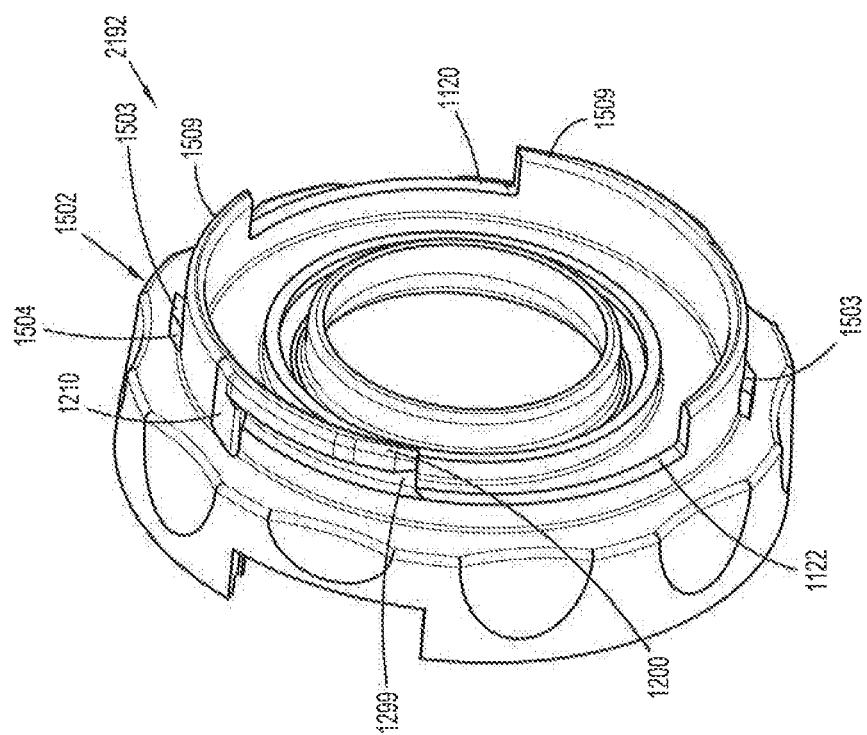
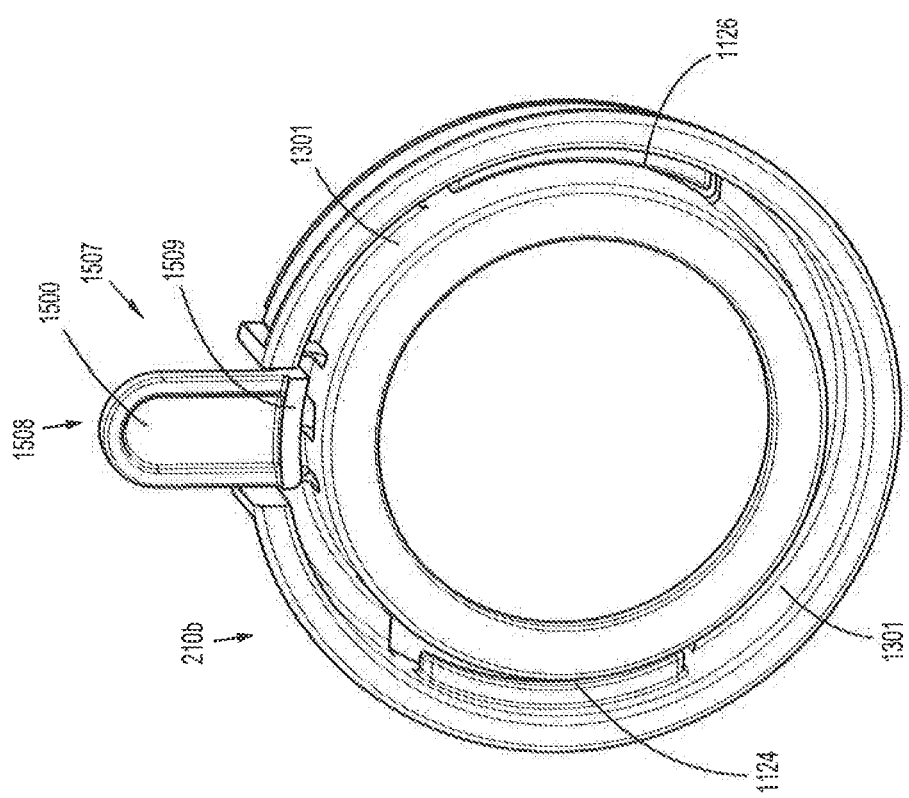

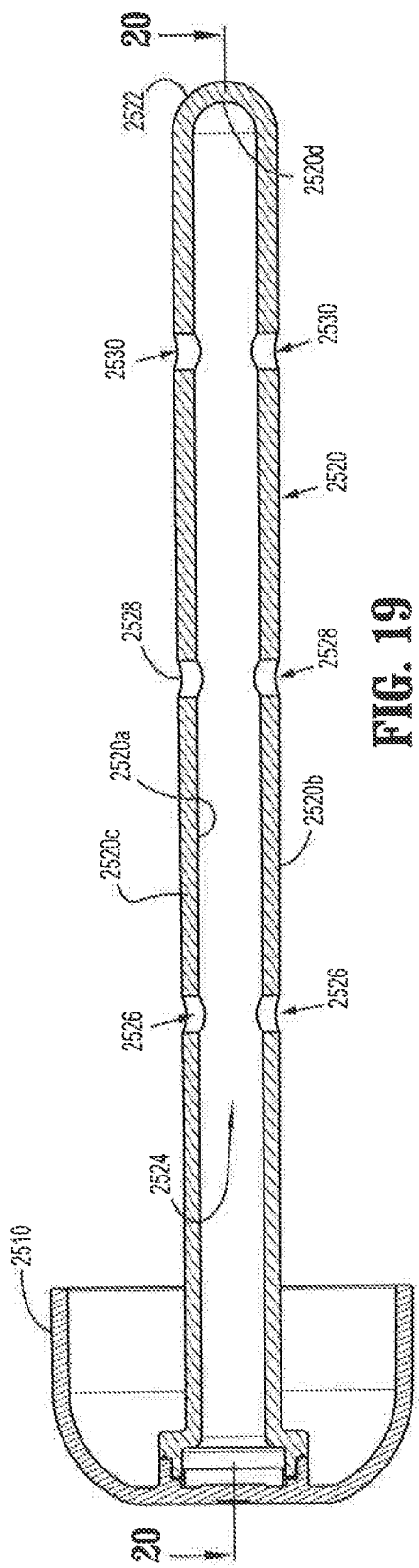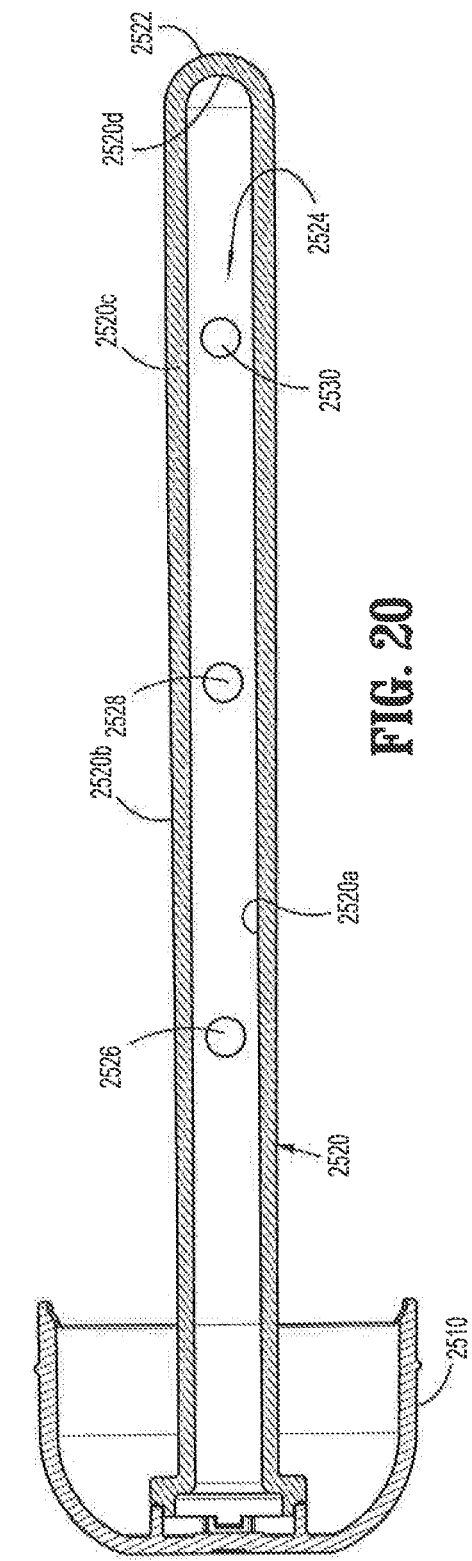

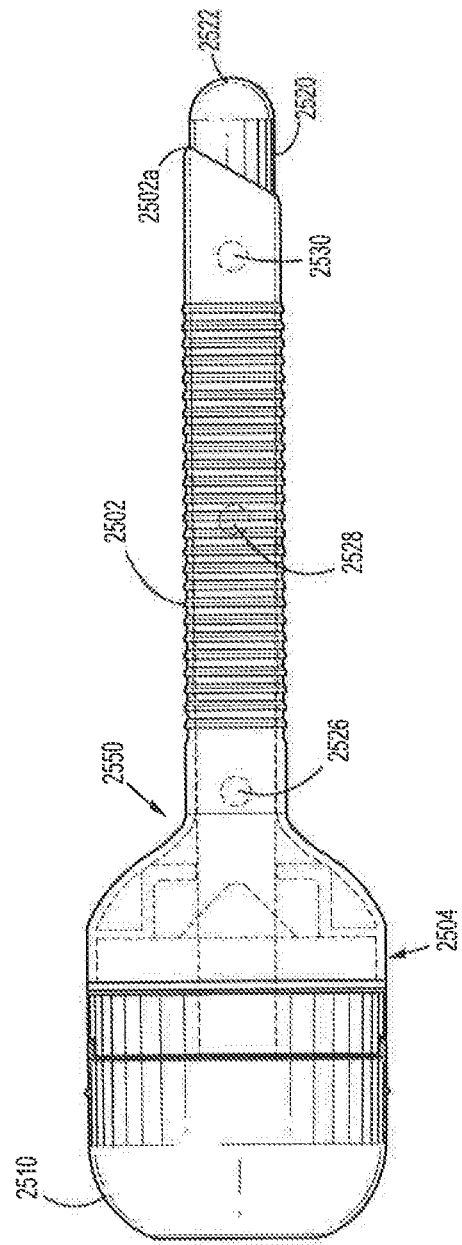

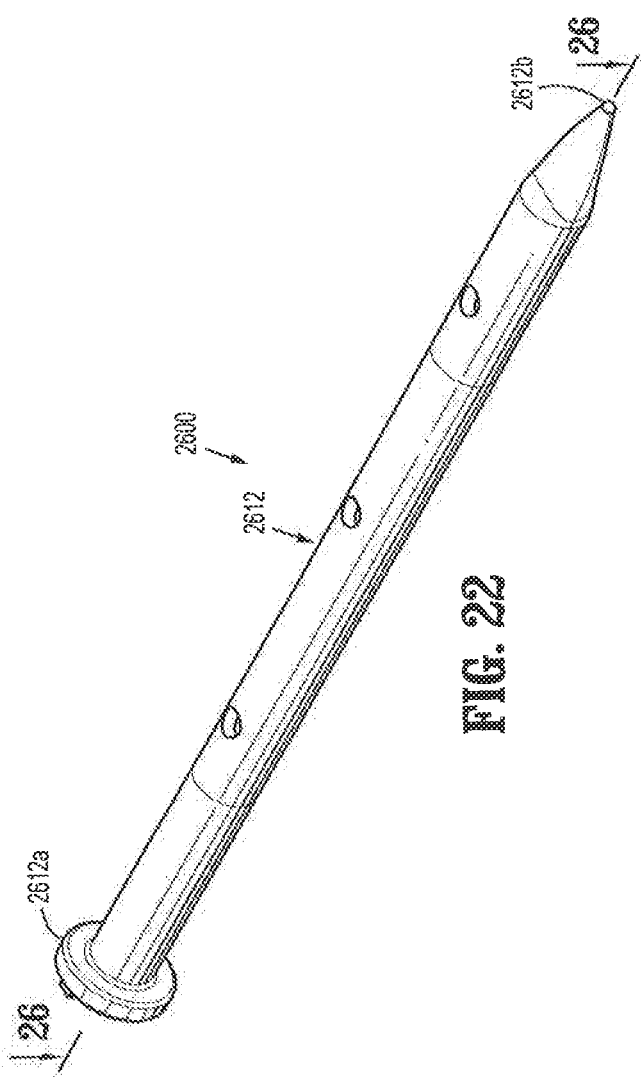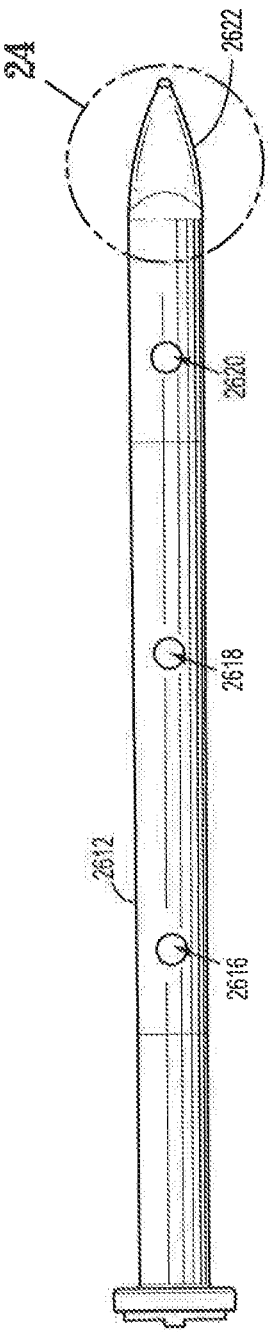

5-5

6-6

7-7

8-8

9-9

10-10

11-11

12-12

13-13

14-14

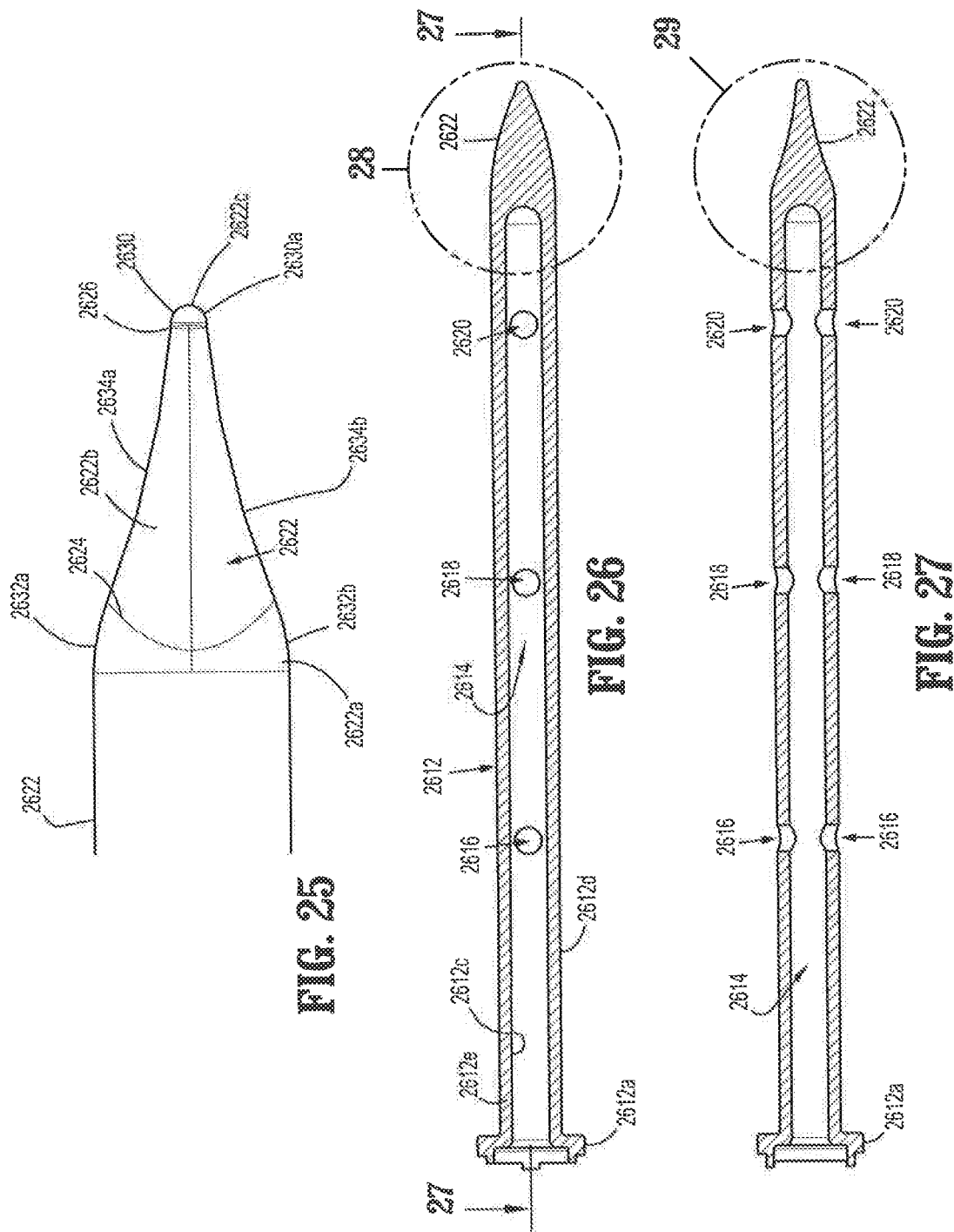

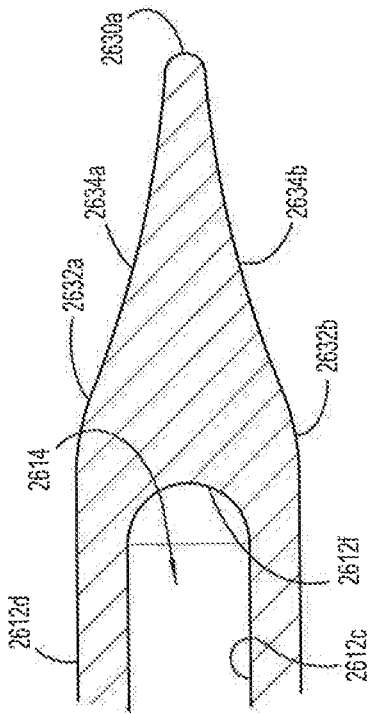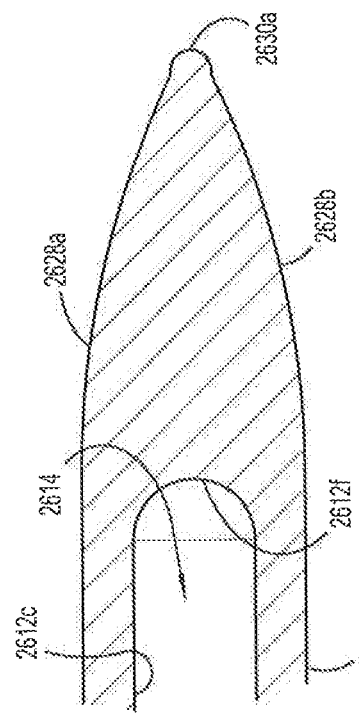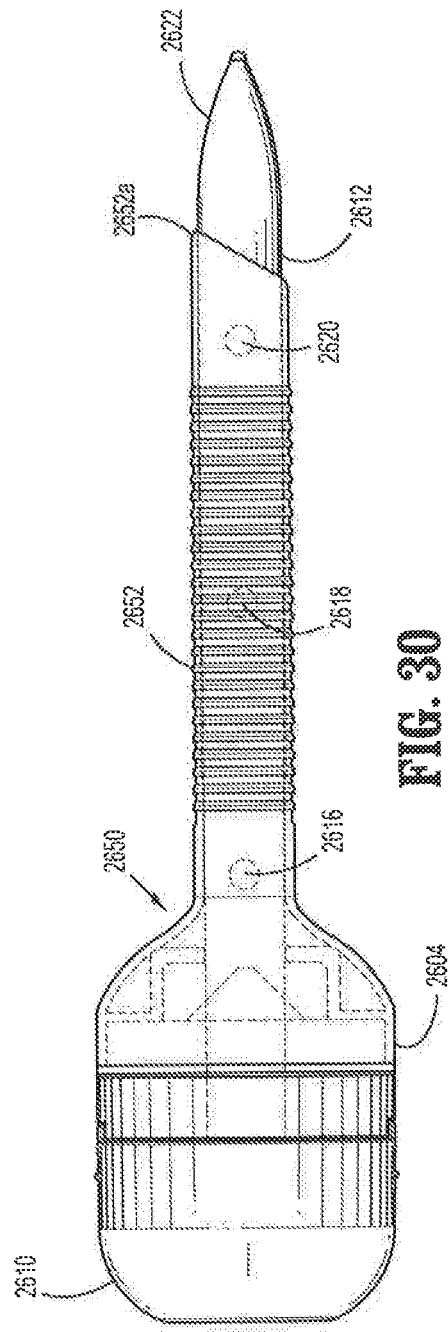

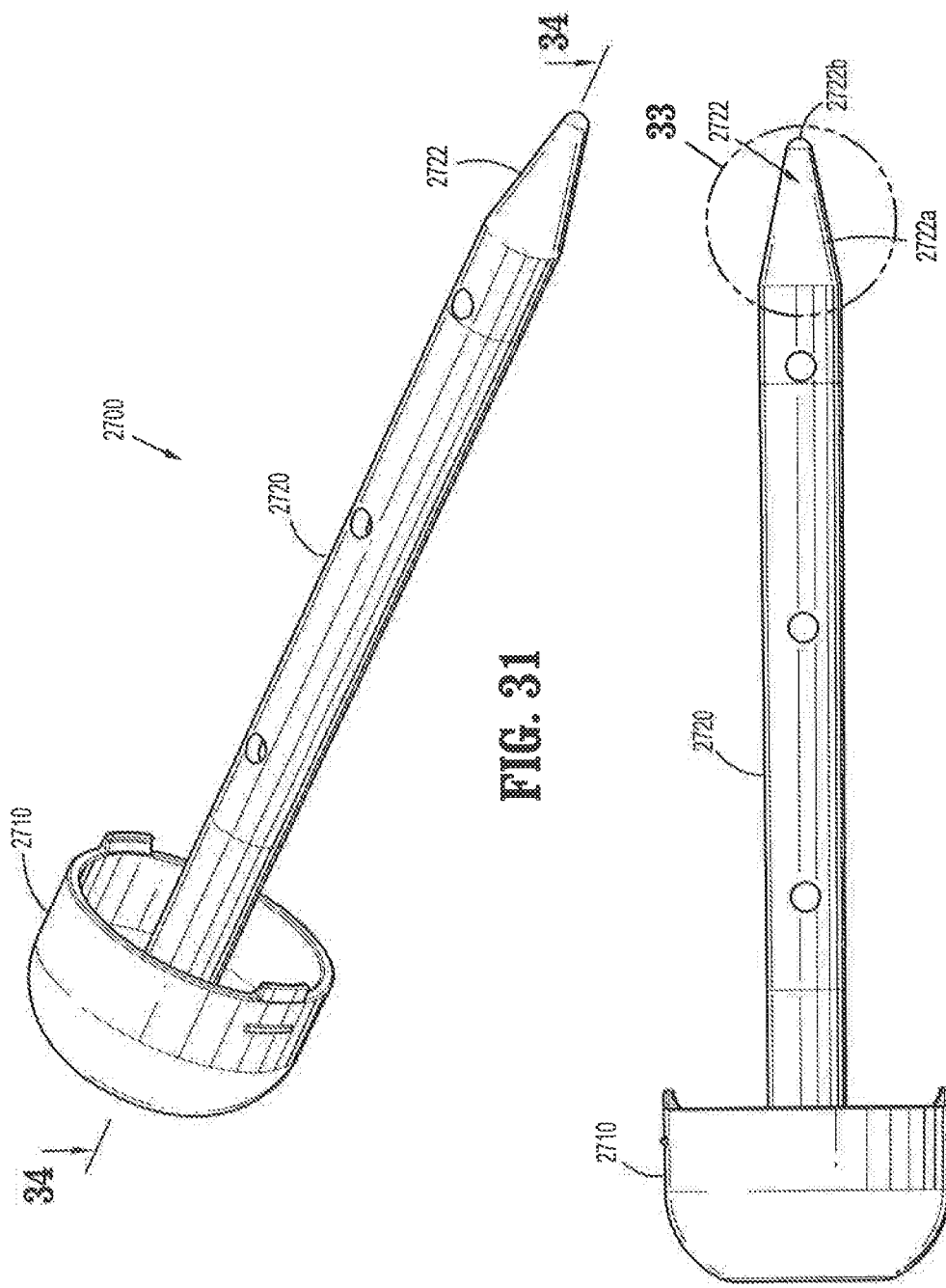

1-1

2-2

3-3

4-4

5-5

6-6

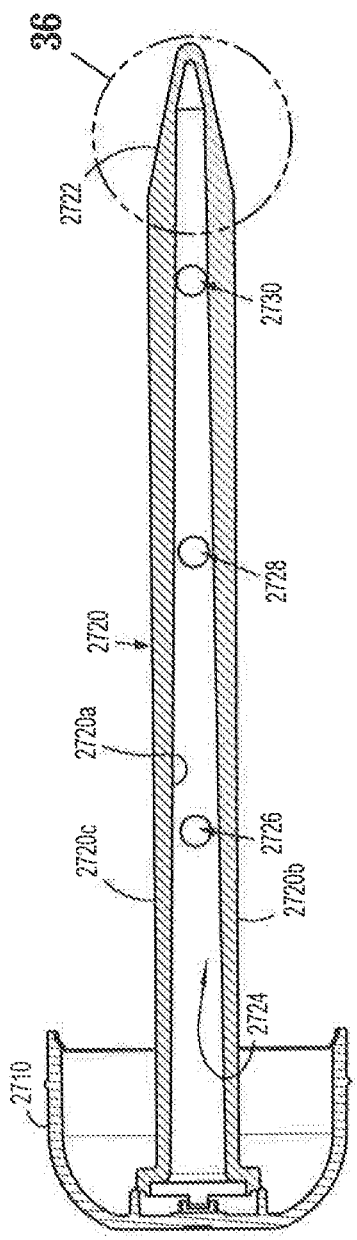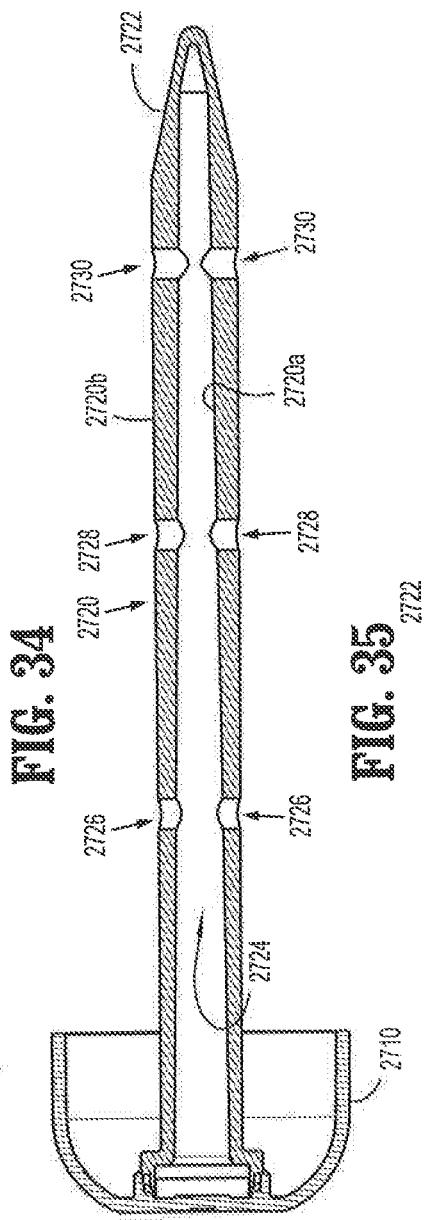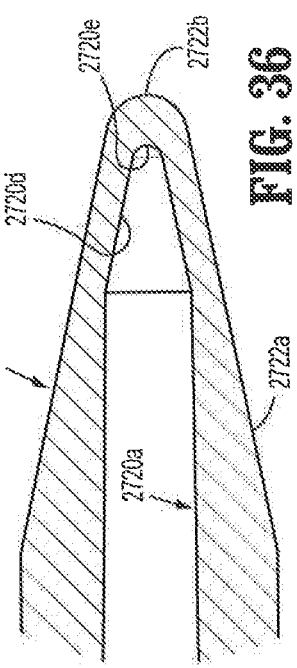

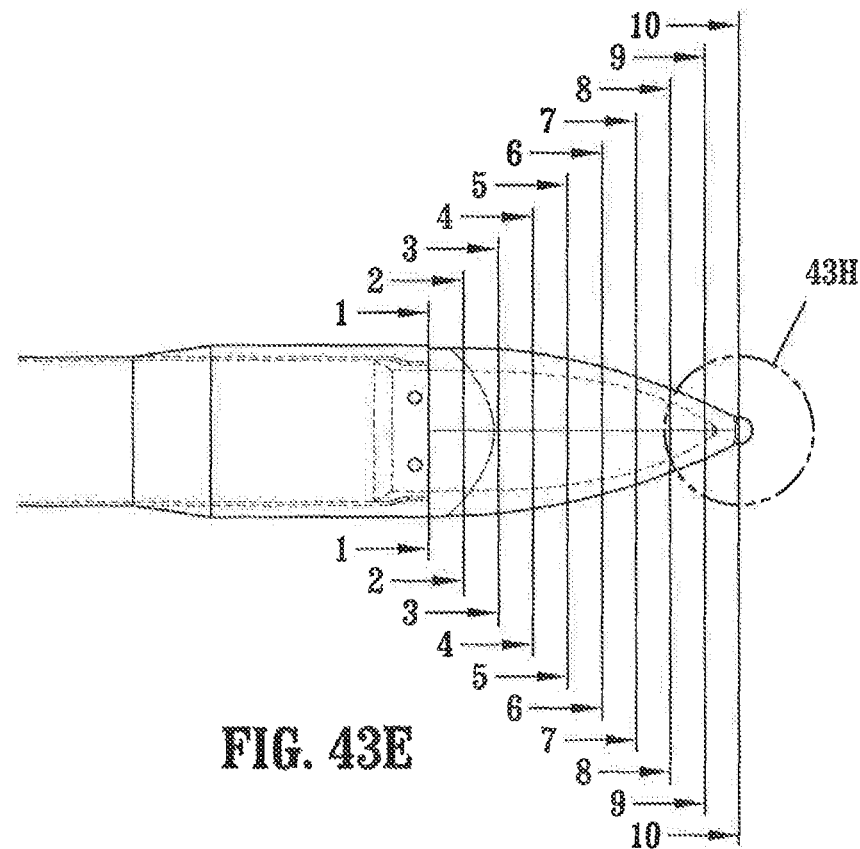
FIG. 43E
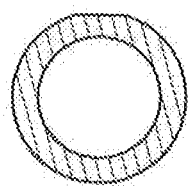
1-1
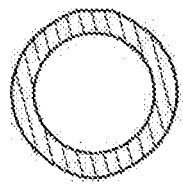
2-2
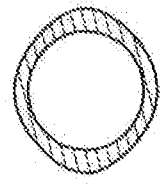
3-3
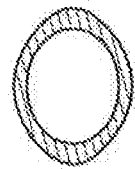
4-4
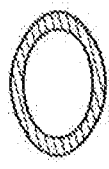
5-5
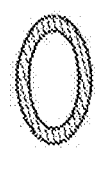
6-6

7-7   8-8   9-9   10-10

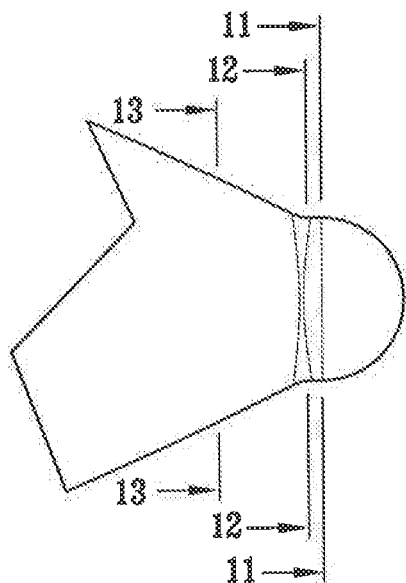
FIG. 43H
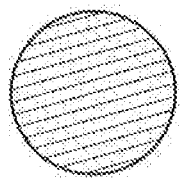
11-11
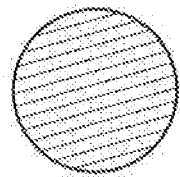
12-12
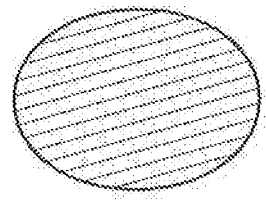
13-13

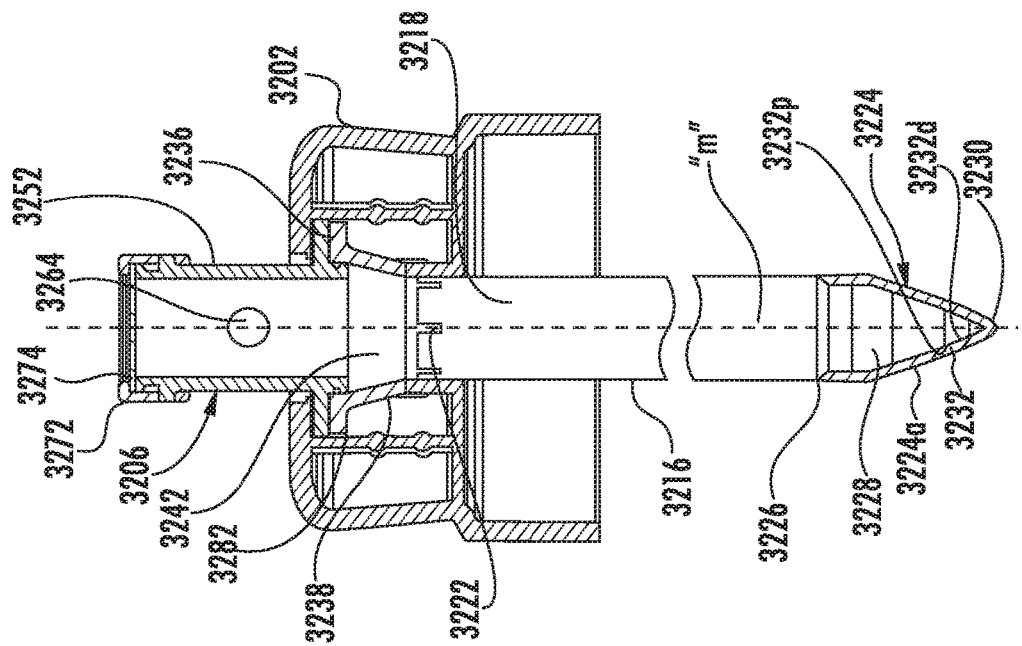
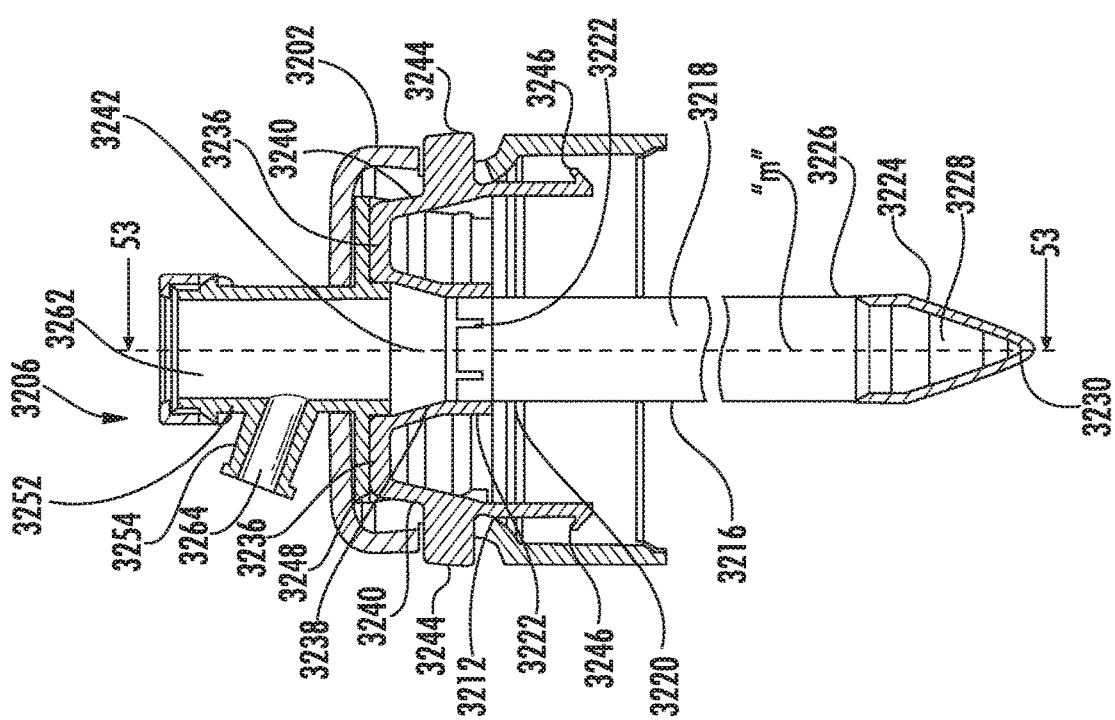

SURGICAL ACCESS SYSTEM

CROSS-REFERENCE TO RELATED APPLICATIONS

This application claims the benefit of and priority to U.S. Provisional Patent Application Ser. No. 62/550,783 filed Aug. 28, 2017, the entire disclosure of which is incorporated by reference herein.

BACKGROUND

1. Technical Field

The present disclosure relates to a surgical access system including a cannula assembly and an obturator assembly. In particular, the present disclosure relates to an obturator assembly having an independent fluid passage isolated from the cannula assembly for direct introduction of insufflation fluids during entry within an underlying body cavity.

2. Discussion of Related Art

Minimally invasive surgical procedures including endoscopic and laparoscopic procedures involve percutaneously accessing an internal surgical site with small-diameter access cannulas. A viewing scope may be introduced through one cannula, and the surgeon may operate using instruments introduced through other appropriately positioned cannulas while viewing the surgical site on a video monitor connected to the viewing scope. The surgeon is thus able to perform a wide variety of surgical procedures requiring only several punctures at the surgical site. As a consequence, patient trauma and recovery time are greatly reduced.

Laparoscopic surgical procedures require introducing insufflation fluids within the abdominal cavity through an insufflation needle to expand the cavity and displace the cavity wall to provide access to the underlying tissue and/or organs. Thereafter, a trocar assembly including a cannula and an obturator, which is positioned within the cannula, is advanced through abdominal tissue to access the abdominal cavity. A viewing device, e.g., a laparoscope, may be positioned within the obturator during insertion to assist and guide the clinician in placement of the cannula. The obturator is removed leaving the cannula in place for reception of surgical instrumentation required to perform a surgical procedure.

Recent efforts have focused on incorporating an insufflation system within a trocar assembly to obviate the necessity of the insufflation needle. In one known system, an insufflating optical trocar includes a cannula, an obturator with an integral tip formed of a transparent material and a laparoscope introducible within the obturator. The cannula and the obturator define an insufflation channel extending between their respective lumens through which insufflation gases pass. The obturator includes a plurality of vents spaced along its shaft and communicating with its lumen to expel the insufflation gases to expand the abdominal cavity.

However, this known insufflating optical trocar has certain drawbacks which not only detract from its usefulness but also present serious medical concerns to the patient. Firstly, the insufflating optical trocar is a complicated design requiring structure to permit passage of insufflation gases from the cannula lumen to the obturator lumen and back to the cannula lumen for eventual release in the abdominal cavity. Secondly, and more significantly, the vents in the shaft of the obturator which expel the insufflation gases are disposed at various locations within the cannula lumen. As a result, during passage of the trocar toward the abdominal cavity, the insufflation gases are released through these vents and enter the interior of the cannula lumen, i.e., between the outer surface of the obturator and the inner wall of the cannula. Unfortunately, these gases within the cannula lumen are prone to flow out the distal end of the cannula and within the abdominal tissue layers surrounding the cavity while the obturator is advancing through the abdominal tissue. This undesired migration of gases into the abdominal tissue layers increases the risk of the formation of a subcutaneous emphysema within the abdominal tissue along with its associated complications including infection, respiratory distress, etc. The presence of gases within the abdominal tissue layers also interferes with establishing a proper insufflated state of the abdominal cavity for performance of the surgical procedure.

SUMMARY

Accordingly, the present disclosure is directed to a surgical access system including a cannula assembly and an obturator assembly positionable within the cannula assembly. The obturator assembly provides an insufflation channel or fluid passage for delivery of insufflation fluids directly to an underlying cavity, e.g., the abdominal cavity. The fluid passage is completely confined within the obturator assembly isolated from the cannula assembly and terminates at a location distal of the cannula assembly such that the insufflation fluids released from the fluid passage are directed toward the abdominal cavity and not within the cannula assembly, thereby minimizing potential of the formation of a subcutaneous emphysema within the abdominal tissue layers.

In one embodiment, the surgical access system includes a cannula assembly and an obturator assembly. The cannula assembly includes a cannula member defining a longitudinal axis, and having a cannula wall with a cannula lumen. The obturator assembly includes an obturator housing and an obturator member extending from the obturator housing and being at least partially positionable within the cannula lumen. The obturator member includes an obturator wall having a penetrating member configured for penetrating tissue, and at least one fluid opening therethrough. A cap is mounted to the obturator housing. The cap and the obturator member define a fluid passage extending along the longitudinal axis to the penetrating member. The fluid passage is isolated from the cannula lumen. An insufflation port is mounted to the cap and defines a port channel in fluid communication with the fluid passage such that insufflation fluids introduced within the port channel are conveyed through the fluid passage and exit the at least one fluid opening independent of the cannula lumen.

In embodiments, the penetrating member includes the at least one fluid opening. In some embodiments, the at least one fluid opening of the penetrating member is disposed beyond the distal end of the cannula member when the obturator member is positioned within the cannula lumen. In other embodiments, at least the penetrating member of the obturator wall includes a transparent material.

In embodiments, the cap includes a cap wall defining a cap lumen, whereby the fluid passage includes the cap lumen. In some embodiments, the obturator wall defines an obturator lumen, whereby the fluid passage includes the obturator lumen. In other embodiments, the cap lumen and the obturator lumen are also configured to receive a surgical instrument. In embodiments, the cap includes an instrument retention member configured for engaging the surgical instrument, to facilitate retention of the instrument at a predetermined position within the obturator member. The instrument retention member may include a friction washer configured to frictionally engage the surgical instrument. The instrument retention member may be configured to engage a laparoscope.

In embodiments, the insufflation port is arranged about a port axis in oblique relation to the longitudinal axis to facilitate directing of the insufflation fluids toward the fluid passage.

In another embodiment, a surgical obturator assembly includes an obturator housing and an elongate obturator member defining a longitudinal obturator axis and distally extending from the obturator housing, and being configured for at least partial introduction within a cannula. The obturator member includes an obturator wall defining an obturator lumen and having a penetrating member configured for penetrating tissue. The penetrating member has at least one fluid opening therethrough. A cap is mounted to the obturator housing, and has a cap lumen in longitudinal alignment with the obturator lumen. The cap lumen and the obturator lumen are configured for reception of a laparoscope, and define an isolated fluid passage extending along the longitudinal axis to the penetrating member. An insufflation port is mounted to the cap proximal of the obturator housing and defines a port channel in fluid communication with the fluid passage such that insufflation fluids introduced within the port channel are conveyed through the fluid passage and exit the at least one fluid opening of the penetrating member.

In embodiments, at least the penetrating member of the obturator wall includes a transparent material. In some embodiments, the cap includes a scope retention member configured for engaging the laparoscope to facilitate retention of the laparoscope at a predetermined position within the obturator member. In other embodiments, the scope retention member is configured to establish a sealing relationship with the laparoscope.

Thus, the present disclosure provides an isolated fluid passage within an obturator assembly, which is independent of the cannula assembly, to ensure insufflation fluids released from the fluid passage enter the underlying body cavity and not within the surrounding tissue. The cap provides the dual function of defining an insufflation port for conveying the insufflation fluids to the fluid passage and providing access for introduction of a viewing scope within the obturator assembly. The dual capability of the cap greatly simplifies the overall design and manufacture of the obturator assembly.

Other advantages of the present disclosure will be appreciated from the following description.

BRIEF DESCRIPTION OF THE DRAWINGS

The above and other aspects, features, and advantages of the present disclosure will become more apparent in light of the following detailed description when taken in conjunction with the accompanying drawings in which:

FIG. 7 is a perspective view of the distal housing component viewed from the proximal side;

FIG. 8 is a perspective view of the proximal housing component;

FIG. 19 is a cross-sectional view of the obturator of FIG. 16, taken along section line 19-19;

FIG. 20 is a cross-sectional view of the obturator of FIG. 19 rotationally offset by 90 degrees, taken along section line 20-20;

FIG. 21 is a side view of the obturator of FIG. 16 inserted through a cannula;

FIG. 22 is a perspective view of a second embodiment of an obturator for separating tissue planes in an endoscopic surgical procedure;

FIG. 23 is a side view of the obturator of FIG. 22;

FIG. 25 is an enlarged top view of the distal portion of the elongate shaft of FIG. 24 rotationally offset by 90 degrees;

FIG. 26 is a cross-sectional view of the obturator of FIG. 22;

FIG. 27 is a cross-sectional view of the obturator of FIG. 26 rotationally offset by 90 degrees, taken along section line 27-27;

FIG. 28 is an enlarged cross-sectional view of the distal portion of the elongate shaft of the obturator of FIG. 22;

FIG. 29 is an enlarged cross-sectional view of the distal portion of the elongate shaft of the obturator of FIG. 27;

FIG. 30 is side view of the obturator of FIG. 22 inserted through a cannula;

FIG. 31 is a perspective view of a third embodiment of an obturator for separating tissue planes in an endoscopic surgical procedure;

FIG. 32 is a side view of the obturator of FIG. 31;

FIG. 34 is a cross-sectional view of the obturator of FIG. 31;

FIG. 35 is a cross-sectional view of the obturator of FIG. 34 rotationally offset by 90 degrees;

FIG. 36 is an enlarged cross-sectional view of the distal portion of the elongate shaft of the obturator of FIG. 31 of the area of detail;

FIG. 43E is a side partial cross-sectional view of the distal end of the surgical access system of FIG. 38, including various cross-sectional views of the distal tip at various longitudinal positions;

FIG. 43F-43H are top views of the distalmost nub of the distal end of the surgical access system of FIG. 38, including various cross-sectional views of the distal tip at various longitudinal positions;

FIG. 52 is a side cross-sectional view of the obturator assembly;

FIG. 53 is a cross-sectional view of the obturator assembly taken along the lines 53-53 of FIG. 52;

DETAILED DESCRIPTION

Figure 1:
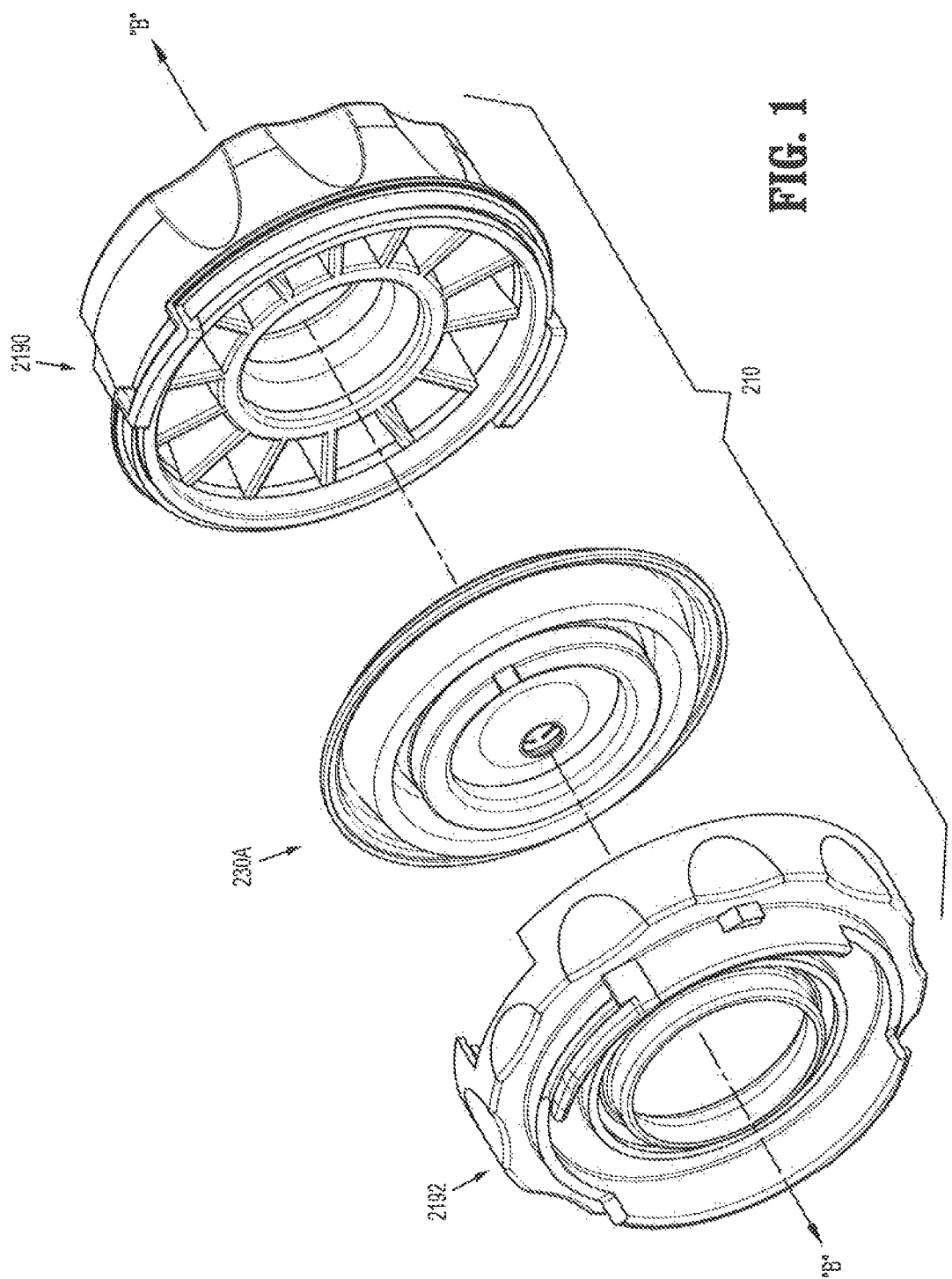
FIG. 1 is a perspective, assembly view of a valve assembly and a portion of a housing.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals refer to similar or identical elements throughout the description of the figures.

As used herein, the term "distal" refers to that portion of the instrument, or component thereof which is farther from the user while the term "proximal" refers to that portion of the instrument or component thereof which is closer to the user.

In various embodiments, the present invention relates to aspects of a trocar assembly. The trocar assembly may be employed during, e.g., laparoscopic surgery and may, in various embodiments, provide for the sealed access of laparoscopic surgical instruments into an insufflated body cavity, such as the abdominal cavity. Generally, and as will be described in additional detail below, the trocar assemblies of the present invention include a trocar cannula (having a valve housing mounted on a cannula tube) and a trocar obturator insertable therethrough. The trocar cannula and obturator are separate components but are capable of being selectively connected together. For example, the obturator may be inserted into and through the trocar cannula until the handle of the obturator engages, e.g., selectively locks into, the proximal valve housing of the trocar cannula. In this initial position, the trocar assembly is employed to tunnel through an anatomical structure, e.g., the abdominal wall, either by making a new passage through the structure or by passing through an existing opening through the structure. Once the trocar assembly has tunneled through the anatomical structure, the trocar obturator is removed, leaving the trocar cannula in place in the structure, e.g., in the incision created by the trocar assembly. The proximal valve housing of the trocar cannula may include valves that prevent the escape of insufflation gases from the body cavity, while also allowing surgical instruments to be inserted into the cavity.

With respect to the trocar obturators, in various embodiments, a bladeless optical obturator—an example of which is set forth in additional detail below—may be provided that permits separation of tissue planes in a surgical procedure and visualization of body tissue fibers as they are being separated, thereby permitting a controlled traversal across a body wall. In other embodiments, the obturator may be bladeless without being optical, e.g., without providing contemporaneous visualization thereof through the distal tip of an obturator. The bladeless obturator may be provided for the blunt dissection of the abdominal lining during a surgical procedure. Various examples of obturator components are disclosed and illustrated herein, e.g., bladed, bladeless, blunt, optical, non-optical, etc. as will be described in additional detail below. However, it should be recognized that various other types of obturators may be employed, e.g., obturators having tip geometries other than those shown.

The proximal valve housing of the trocar cannula may include various arrangements and/or components. In various embodiments, the proximal valve housing includes an instrument valve assembly (having an instrument valve component) that is selectively attachable to, and detachable from, a distal housing component (which may or may not be permanently attached to a cannula tube and which may or may not include additional valves, e.g., a zero seal valve such as a duckbill valve. Example embodiments of such arrangements are set forth in greater detail below.

With reference to FIGS. 1-15, and with particular reference to FIG. 1, instrument valve assembly 210 includes a first housing portion 2190, a second housing portion 2192 and instrument valve component or valve assembly 230A. Instrument valve component 230A is positioned between and maintained within first housing portion 2190 and second housing portion 2192. First housing portion 2190 and second housing portion 2192 of instrument valve assembly 210 may be welded together.

Figure 2:
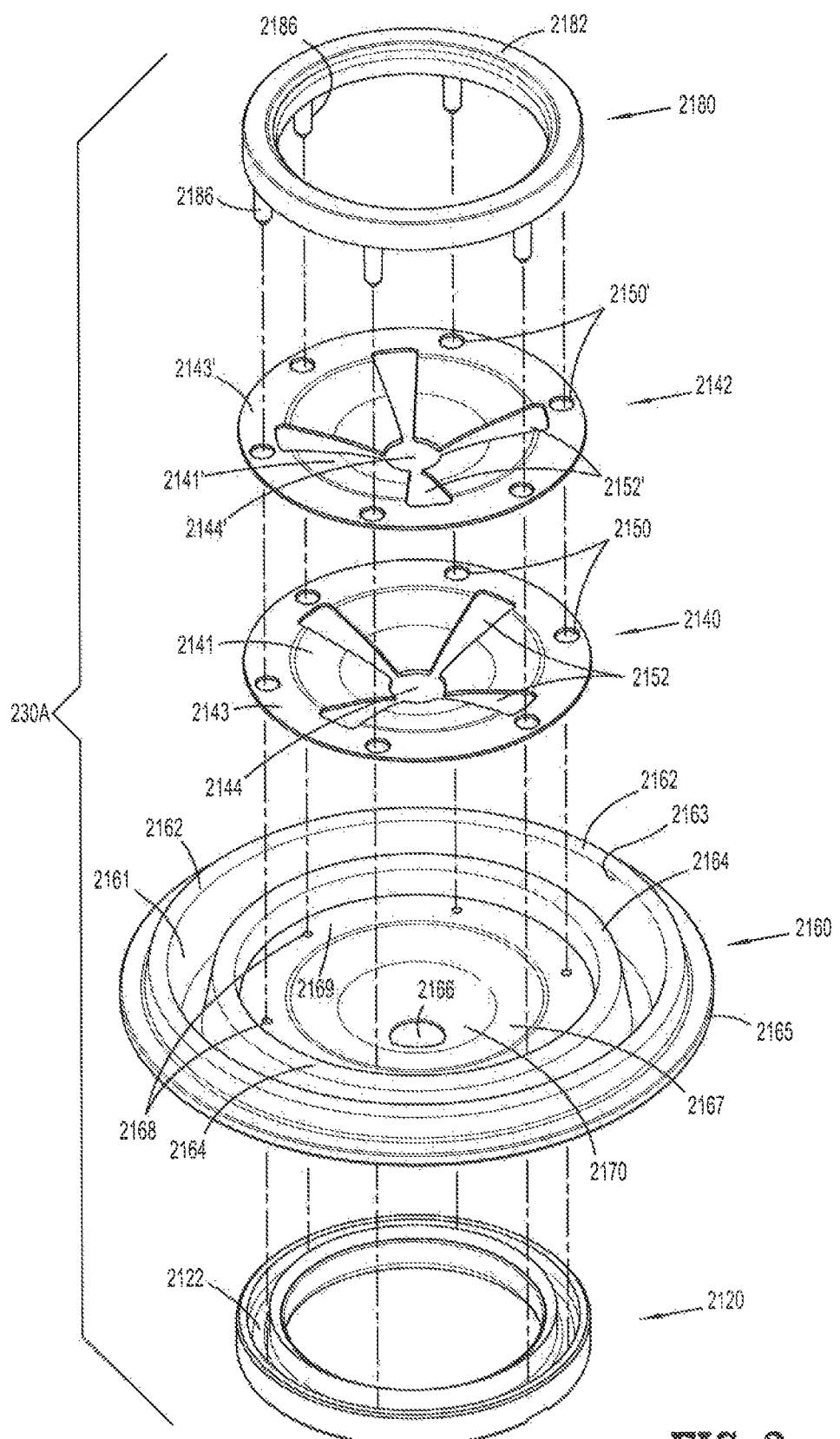
FIG. 2 is a perspective view, with parts separated, of the valve assembly.

With reference to FIG. 2, instrument valve component 230A includes an elastomeric septum seal 2160, a lower seal retainer 2120, and an upper seal retainer 2180. Lower seal retainer 2120 and upper seal retainer 2180 may be referred to as a lower seal support and an upper seal support, respectively. Instrument valve component 230A further includes first and second guard members 2140, 2142. In alternate embodiments, fewer or more guard members (see FIGS. 5A-5D) than the two guard members shown herein may be employed.

With reference to FIG. 2, septum seal 2160 is configured to provide a seal around an outer surface of an instrument passing therethrough. Septum seal 2160 includes a bellowed outer seal portion 2163, an intermediate flat guard portion 2169, and a curved inner seal portion 2167 (or first sloped portion). The bellowed outer seal portion 2163 includes an inner bellows 2164, an outer bellows 2162 and a radially outermost lip 2165. Flat guard portion 2169 includes a plurality of apertures 2168 annularly disposed therethrough. Inner seal portion 2167 has an orifice 2166 at its radial center. It should be noted that, while the bellowed outer seal portion 2163 is shown and described herein as having an inner and outer bellows, in alternate embodiments, fewer or more bellows may be employed.

Curved inner seal portion 2167 (or first sloped portion) is disposed between flat guard portion 2169 and second sloped portion 2170 (FIG. 2). Curved inner seal portion 2167 may be sloped at a first angle, whereas second sloped portion 2170 may be sloped at a second angle, where the first and second angles are different. In particular, the angle of second sloped portion 2170 may be greater than the angle of curved inner seal portion 2167. Second sloped portion 2170 is configured to accommodate orifice 2166 of septum seal 2160. The varying angles of curved portions 2167, 2170 of septum seal 2160 may facilitate guiding instrument 211 (FIG. 15) toward orifice 2166. In addition, varying the angles of curved portions 2167, 2170 of septum seal 2160 may help prevent the septum seal 2160 from inverting when an instrument is withdrawn.

Upper seal retainer 2180 includes a ring 2182 and a plurality of fingers or pins 2186 extending downwardly from ring 2182. Lower seal retainer 2120 is a ring that includes an annular channel 2122. It should be recognized that, although the plurality of fingers or pins 2186 is shown as extending downwardly from upper seal retainer 2180 for engagement with the lower seal retainer 2120, in other embodiments, the plurality of fingers or pins 2186 may instead extend upwardly from lower seal retainer 2120 for engagement with the upper seal retainer 2180, or the pins and fingers may be located on both the upper and lower seal retainers 2120, 2180 and extend both upwardly and downwardly. In addition, it should also be recognized that, while the lower seal retainer 2120 is shown and described herein as including an annular channel 2122, the lower seal retainer 2120 may instead include one or more discrete openings for receiving the corresponding fingers or pins, which may improve the engagement of the pins/fingers with the lower seal ring and increase the retention therebetween once connected to each other. An advantage of employing a channel, however, is that circumferential alignment of the upper and lower rings prior to connecting them may be avoided.

First guard member 2140 includes a plurality of curved guard portions 2141 and a flat guard portion 2143. Flat guard portion 2143 includes a plurality of apertures 2150 annularly disposed therethrough. The plurality of curved guard portions 2141 collectively define an orifice 2144 at their radial center. First guard member 2140 further defines a plurality of slits 2152 between the plurality of curved guard portions 2141 and extending from orifice 2144 toward flat guard portion 2143. Slits 2152 include four slits that define a substantially "cross" configuration.

Second guard member 2142 includes a plurality of curved guard portions 2141' and a flat guard portion 2143'. Flat guard portion 2143' includes a plurality of apertures 2150' annularly disposed therethrough. The plurality of curved guard portions 2141' collectively define an orifice 2144' at their radial center. Second guard member 2142 further defines a plurality of slits 2152' between the plurality of curved guard portions 2141' and extending from orifice 2144' toward flat guard portion 2143'. Slits 2152' include four slits that define a substantially "cross" configuration.

While first and second guard members 2140, 2142 are shown and described herein as each having four slits 2152, 2152', respectively, it should be recognized that a greater number or a lesser number of slits for each guard member 2140, 2142 may be employed. Likewise, while first and second guard members 2140, 2142 are shown and described herein as each having four guard portions 2141, 2141', respectively, it should be recognized that a greater number or a lesser number of guard portions for each guard member 2140, 2142 may also be employed. For example, slits and/or guard portions numbering between 2 and 10 for each guard member 2140, 2142 are contemplated.

Additionally, while each slit 2152, 2152' and each guard portion 2141, 2141' is shown to be substantially triangular in shape, it should be recognized that other geometrical shapes for each of slits 2152, 2152' and guard portions 2141, 2141' of the first and second guard members 2140, 2142, respectively, may be employed. Still further, while the guard portions 2141, 2141' are shown and described herein as being curved, such guard portions could instead be straight or may each have multiple curved portions. In an embodiment, each of the guard portions 2141, 2141' may have a curvature that match the curvature of the curved inner seal portion 2167 of the septum seal 2160. Additionally or alternatively, each of the guard portions 2141, 2141' may have a curvature that exceeds, e.g., that is more curved than, the curvature of the curved inner seal portion 2167 of the septum seal 2160—such an arrangement may help prevent the curved inner seal portion 2167 of the septum seal 2160 and the guard portions 2141, 2141' from being inverted, e.g., bent proximally, when an instrument is withdrawn therethrough.

Figure 3:
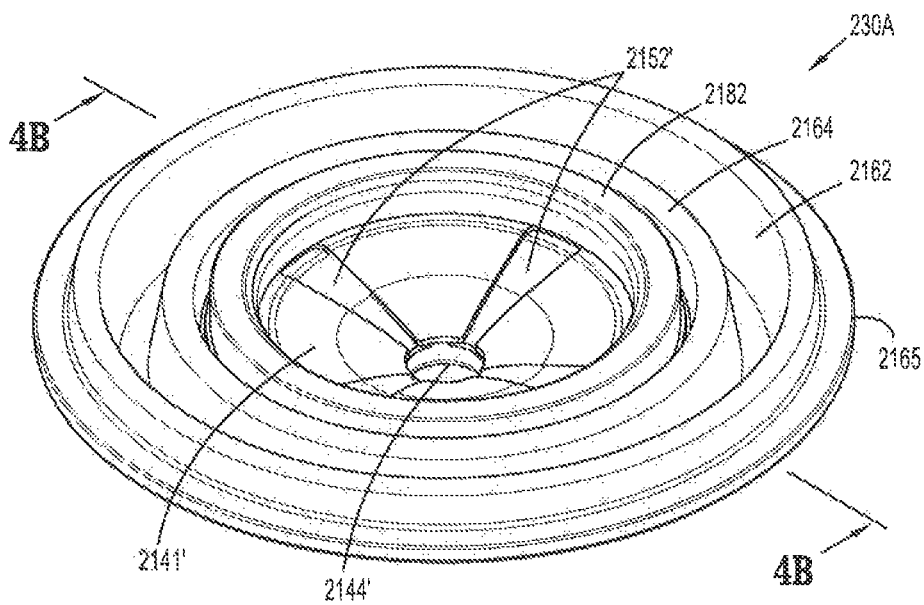
FIG. 3 is a perspective view of the valve assembly.
Figure 4A:
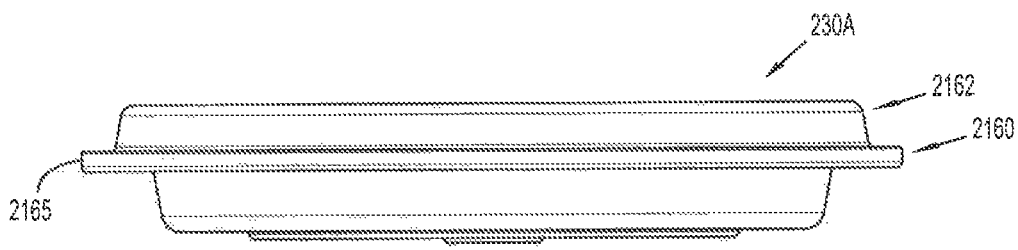
FIG. 4A is a side view of the valve assembly.
Figure 4B:
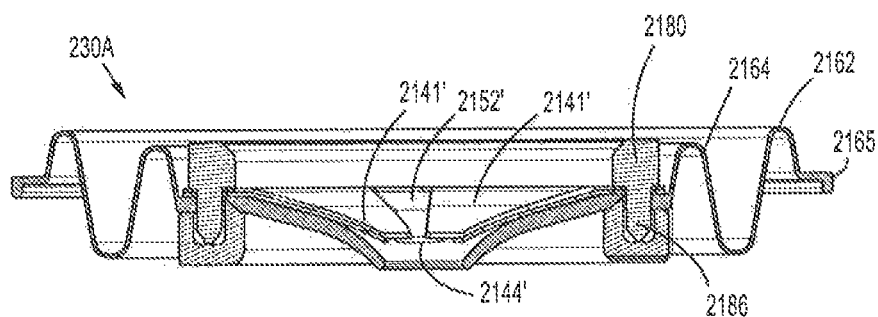
FIG. 4B is a cross-sectional view of the valve assembly taken along line 4B-4B in FIG. 3.

FIG. 3 is an assembled view of instrument valve assembly 210, while FIGS. 4A and 4B are a side view and a side cross-sectional view, respectively, of instrument valve component 230A. When instrument valve component 230A is assembled, pins 2186 of upper seal retainer 2180, apertures 2150, 2150' of first and second guard members 2140, 2142, and apertures 2168 of septum seal 2160 are longitudinally aligned, such that each one of pins 2186 extend through respective ones of apertures 2150, 2150' of first and second guard members 2140, 2142 and through respective ones of apertures 2168 of septum seal 2160. The distalmost ends of pins 2186 engage annular channel 2122 of lower seal retainer 2120 and are retained therein by any suitable technique, such as by snap-fit, friction-fit, welding, etc., such that septum seal 2160 and first and second guard members 2140, 2142 are secured between upper seal retainer 2180 and lower seal retainer 2120.

As shown in FIGS. 3-4B, when instrument valve component 230A is assembled, first and second guard members 2140, 2142 are rotationally offset with respect to each other by 90 degrees (relative to the longitudinal axis), such that slits 2152 of first guard member 2140 and slits 2152' of second guard member 2142 are also rotationally offset from each other by 90 degrees (relative to the longitudinal axis). The rotational offset of first and second guard members 2140, 2142 with respect to each other provides for the plurality of curved guard portions 2141 of first guard member 2140 to span the width of slits 2152' of second guard member 2142, and for the plurality of curved guard portions 2141' of second guard member 2142 to span the width of slits 2152 of first guard member 2140.

The rotational offset of first and second guard members 2140, 2142 with respect to each other facilitates the protection of septum seal 2160 when instrument valve component 230A is disposed within the housing of a cannula assembly 200 (FIG. 6) and an instrument is inserted through orifices 2144, 2144'. It should be recognized that the first and second guard members 2140, 2142 may instead be aligned with each other, depending on the shape and number of the guard portions. Additionally, it should be recognized that the first and second guard members 2140, 2142 may be misaligned by more or less than 90 degrees with respect to each other, depending on the shape and number of the guard portions.

In the embodiment shown in, e.g., FIG. 4B, the height of outer bellows 2162 is greater than the height of inner bellows 2164. Inner and outer bellows 2164, 2162 extend generally perpendicular to flat guard portion 2169. Inner and outer bellows 2164, 2162 extend generally radially on septum seal 2160. In other embodiments, the height of inner and outer bellows 2164, 2162 may be substantially equal, or the height of inner bellows 2164 may be greater than the height of outer bellows 2162. Additionally, the width of inner bellows 2164 may be substantially equal to the width of outer bellows 2162. The width of inner bellows 2164 may be greater than or less than the width of outer bellows 2162. For example, outer bellows 2162 may be twice the width of inner bellows 2164, or vice versa.

In the embodiment shown, each one of the slits 2152 of the first guard member 2140 has an equal width and length with respect to the other slits 2152. For example, as shown, the width of each one of the slits 2152 progressively increases as slits 2152 extend from the orifice 2144 to the flat guard portion 2143 so as to define a substantially triangular configuration. Therefore, the narrowest part of slits 2152 is near orifice 2144 and the width of each slit 2152 increases from a distal end 2147 to a proximal end 2149 of each slit 2152. Moreover, in the embodiment shown, the width of curved guard portions 2141 is greater at a given radial location than the width of slits 2152. For example, the width of a curved guard portion 2141, at a given radial location, may be more than twice the width of a slit 2152. The width of slits 2152 may be selected such that the guard portions 2141 experience adequate flexibility when surgical instrument 211 (FIG. 15) is inserted through orifice 2144 while still providing adequate protection to the septum seal 2160 upon insertion and withdrawal of an instrument.

In various embodiments, the slits 2152 may extend beyond curved guard portion 2141 and into flat guard portion 2143. Slits 2152 may or may not extend to the outer radial edge of flat guard portion 2143, although having slits 2152 not extend to the outer radial edge of flat guard portion 2143 may provide the advantage of the first guard member 2140 being a single component that is more easily handled during manufacture. Slits 2152 may extend less than half the length of flat guard portion 2143. This extension of slits 2152 beyond curved guard portion 2141 may provide for additional flexibility of the curved guard portions 2141, as well as first guard member 2140, when a surgical instrument 211 is inserted through orifice 2144.

Advantageously, the slits 2152' and curved guard portions 2141' of second guard member 2142 may exhibit the same geometries as described above with regard to slits 2152 and curved guard portions 2141, respectively, of first guard member 2140. Curved guard portion 2141 may have a first curvature or angle, and curved guard portion 2141' may have a second curvature or angle, where the first and second angles/curvatures are equal to each other. When second guard member 2141 is positioned adjacent to or in abutting relationship with first guard member 2140, the matching angles/curvatures of curved guard portions 2141, 2141' may allow for a relatively smooth surface with minimal voids therebetween, reducing the likelihood of an instrument or feature of an instrument sliding between or getting trapped between the respective guard members. It should also be recognized that, if the slits 2152' and curved guard portions 2141' of second guard member 2142 have the same geometries as slits 2152 and curved guard portions 2141 of first guard member 2140, the first and second guard members 2140, 2142 may also have the same overall geometries, enabling them to be formed on the same tools/molds so as to achieve manufacturing and assembly efficiencies.

In the embodiment shown, the diameter of first guard member 2140 is substantially equal to the diameter of second guard member 2142. The diameter of septum seal 2160 may be greater than the diameter of first and second guard members 2140, 2142. First and second guard members 2140, 2142 are adapted and dimensioned to be accommodated within the inner boundaries of inner bellows 2164 of septum seal 2160 such that the outer peripheral edge of first and second guard members 2140, 2142 contacts the inner bellows 2164. Manipulation of surgical instrument 211, while in orifice 2166 of septum seal 2160, causes the inner and outer bellows 2164, 2162 to move. The flexibility provided by bellows 2164, 2162 helps to minimize the likelihood that an instrument positioned within the aperture 2166 of the septum seal 2160 will cause the orifice to cat-eye and thereby leak insufflation gas. In addition, the bellows 2164, 2162 function to move the aperture 2166 of the septum seal 2160 back to the central longitudinal axis B of the device when no instrument is positioned therein, which also increases the likelihood that a subsequently inserted instrument will travel through the aperture 2166, and minimizes the likelihood that such a subsequently inserted instrument will contact the radially outer portions of the septum seal and thereby tear it.

Once instrument valve component 230A has been assembled as shown in FIGS. 3-4B, it is incorporated into instrument valve assembly 210 as shown in FIG. 1. Specifically, instrument valve component 230A is maintained in position within instrument valve assembly 210 by positioning radially outermost lip 2165 of valve component 230A between first and second housing portions 2190, 2192 of proximal housing component 210a (FIGS. 9-12) and then connecting, e.g., by snap-fit, welding, etc., first and second housing portions 2190, 2192 together.

Assembled instrument valve assembly 210 is selectively attachable to, and detachable from, various types of distal cannula assemblies (shown and described in further detail below) in order to collectively provide various types of cannula assemblies.

Figure 5A:
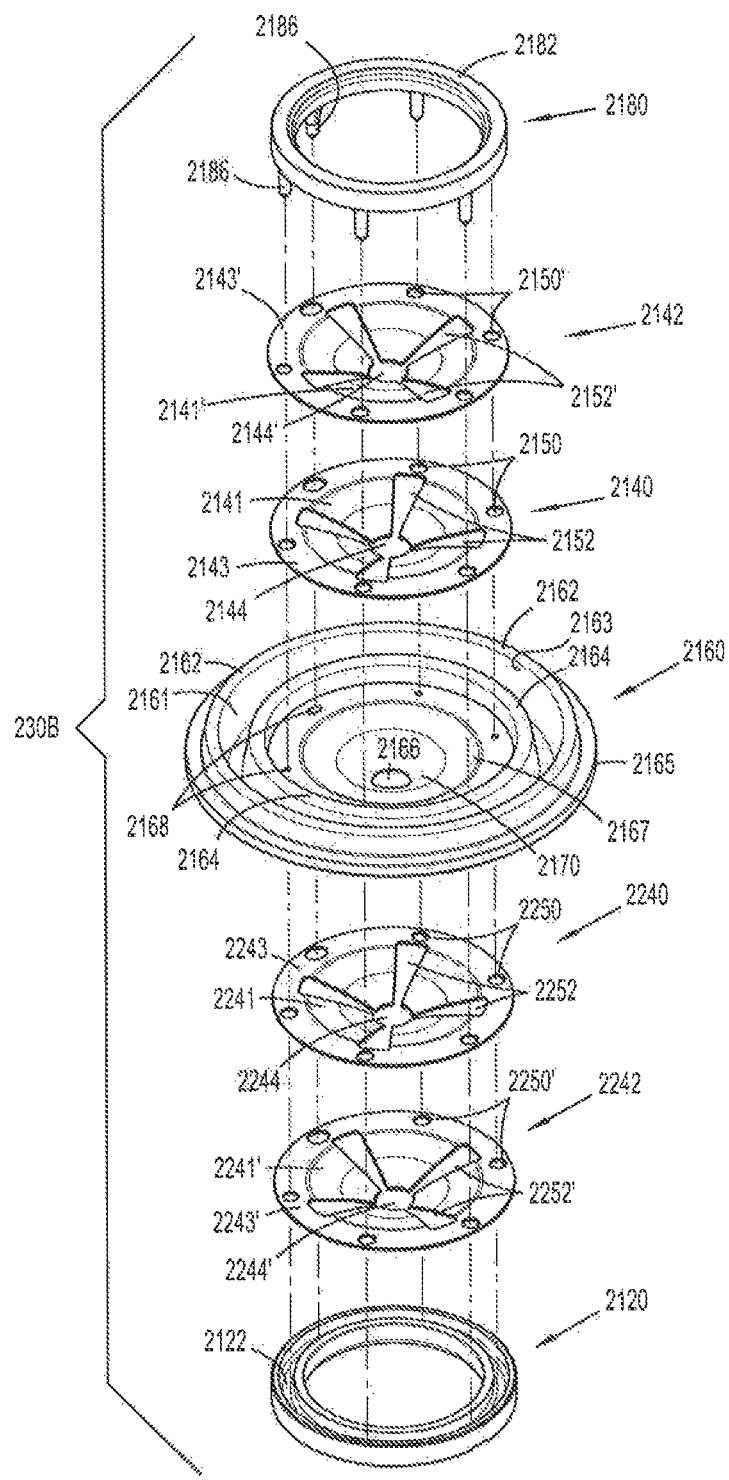
FIG. 5A is a perspective view, with parts separated, of another embodiment of a valve assembly.

FIGS. 5A-5D illustrate another embodiment of an instrument valve component or valve assembly 230B. With reference to FIG. 5A, instrument valve component 230B includes an elastomeric septum seal 2160, a lower seal retainer 2120, and an upper seal retainer 2180. Lower seal retainer 2120 and upper seal retainer 2180 may be referred to as a lower seal support and an upper seal support, respectively. Instrument valve component 230B further includes first and second guard members 2140, 2142. All these elements have been described above with reference to FIGS. 2-4B and their description will be omitted for sake of clarity. In contrast to FIGS. 2-4B, FIGS. 5A-5D illustrate a third guard member 2240 and a fourth guard member 2242 directly beneath or at a distal end of the septum seal 2160.

Third guard member 2240 includes a plurality of curved guard portions 2241 and a flat guard portion 2243. Flat guard portion 2243 includes a plurality of apertures 2250 annularly disposed therethrough. The plurality of curved guard portions 2241 collectively define an orifice 2244 at their radial center. Third guard member 2240 further defines a plurality of slits 2252 between the plurality of curved guard portions 2241 and extending from orifice 2244 toward flat guard portion 2243. Slits 2252 include four slits that define a substantially "cross" configuration.

Fourth guard member 2242 includes a plurality of curved guard portions 2241' and a flat guard portion 2243'. Flat guard portion 2243' includes a plurality of apertures 2250' annularly disposed therethrough. The plurality of curved guard portions 2241' collectively define an orifice 2244' at their radial center. Fourth guard member 2242 further defines a plurality of slits 2252' between the plurality of curved guard portions 2241' and extending from orifice 2244' toward flat guard portion 2243'. Slits 2252' include four slits that define a substantially "cross" configuration.

While third and fourth guard members 2240, 2242 are shown and described herein as each having four slits 2252, 2252', respectively, it should be recognized that a greater number or a lesser number of slits for each guard member 2240, 2242 may be employed. Likewise, while third and fourth guard members 2240, 2242 are shown and described herein as each having four guard portions 2241, 2241', respectively, it should be recognized that a greater number or a lesser number of guard portions for each guard member 2240, 2242 may also be employed. For example, slits and/or guard portions numbering between two and ten for each guard member 2240, 2242 are contemplated.

Additionally, while each slit 2252, 2252' and each guard portion 2241, 2241' is shown to be substantially triangular in shape, it should be recognized that other geometrical shapes for each of slits 2252, 2252' and guard portions 2241, 2241' of the third and fourth guard members 2240, 2242, respectively, may be employed. Still further, while the guard portions 2241, 2241' are shown and described herein as being curved, such guard portions could instead be straight or may each have multiple curved portions. In an embodiment, each of the guard portions 2241, 2241' may have a curvature that is similar to or matches the curvature of the curved inner seal portion 2167 of the septum seal 2160. Additionally or alternatively, each of the guard portions 2241, 2241' may have a curvature that is less than or exceeds the curvature of the curved inner seal portion 2167 of the septum seal 2160.

Figure 5B:
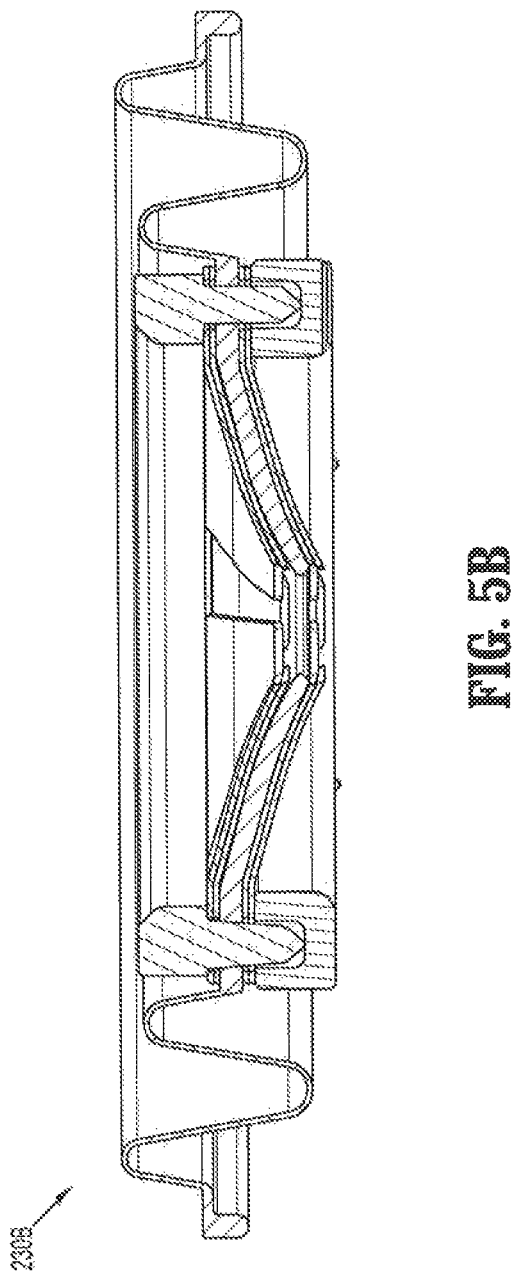
FIG. 5B is a cross-sectional view of the valve assembly of FIG. 5A as assembled.
Figure 5C:
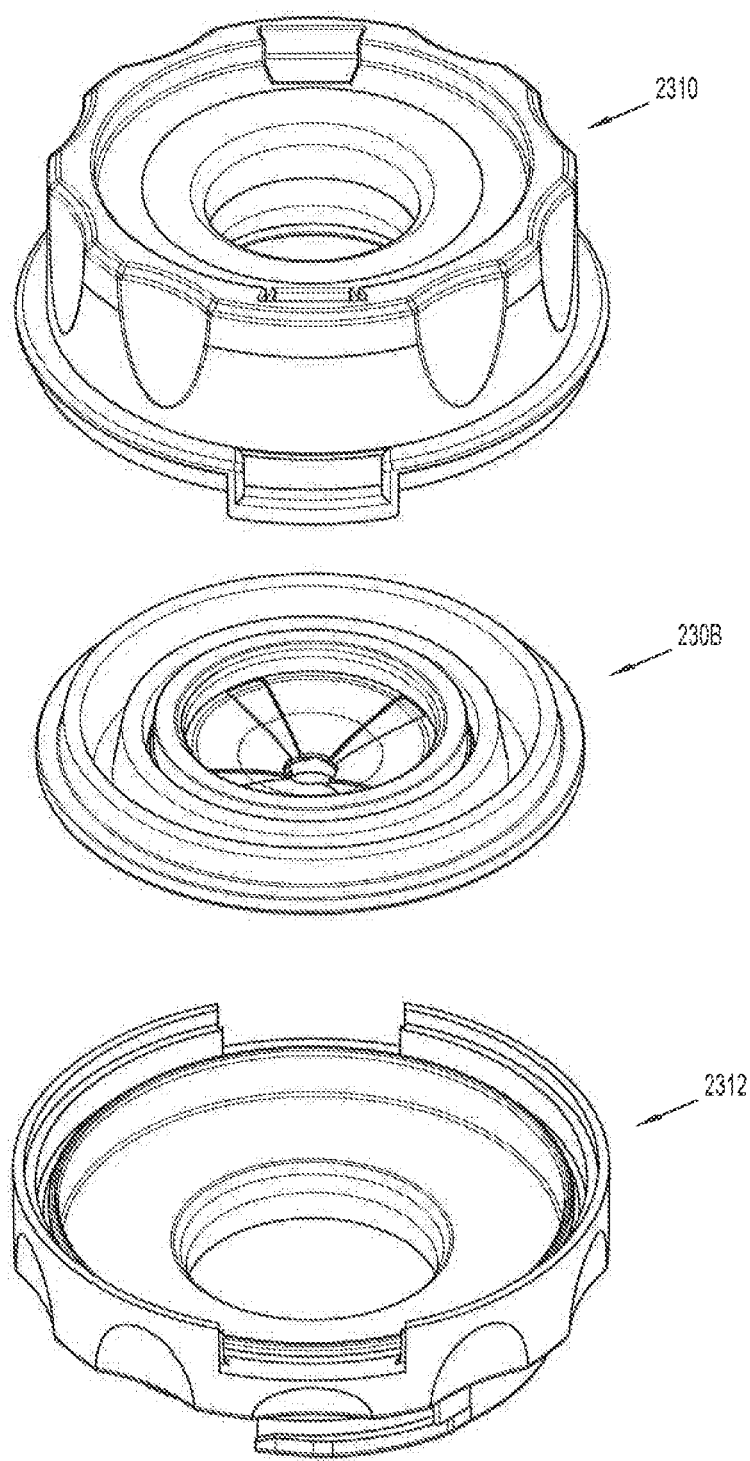
FIG. 5C is a perspective, assembly view of the valve assembly of FIG. 5A and a portion of the housing.
Figure 5D:
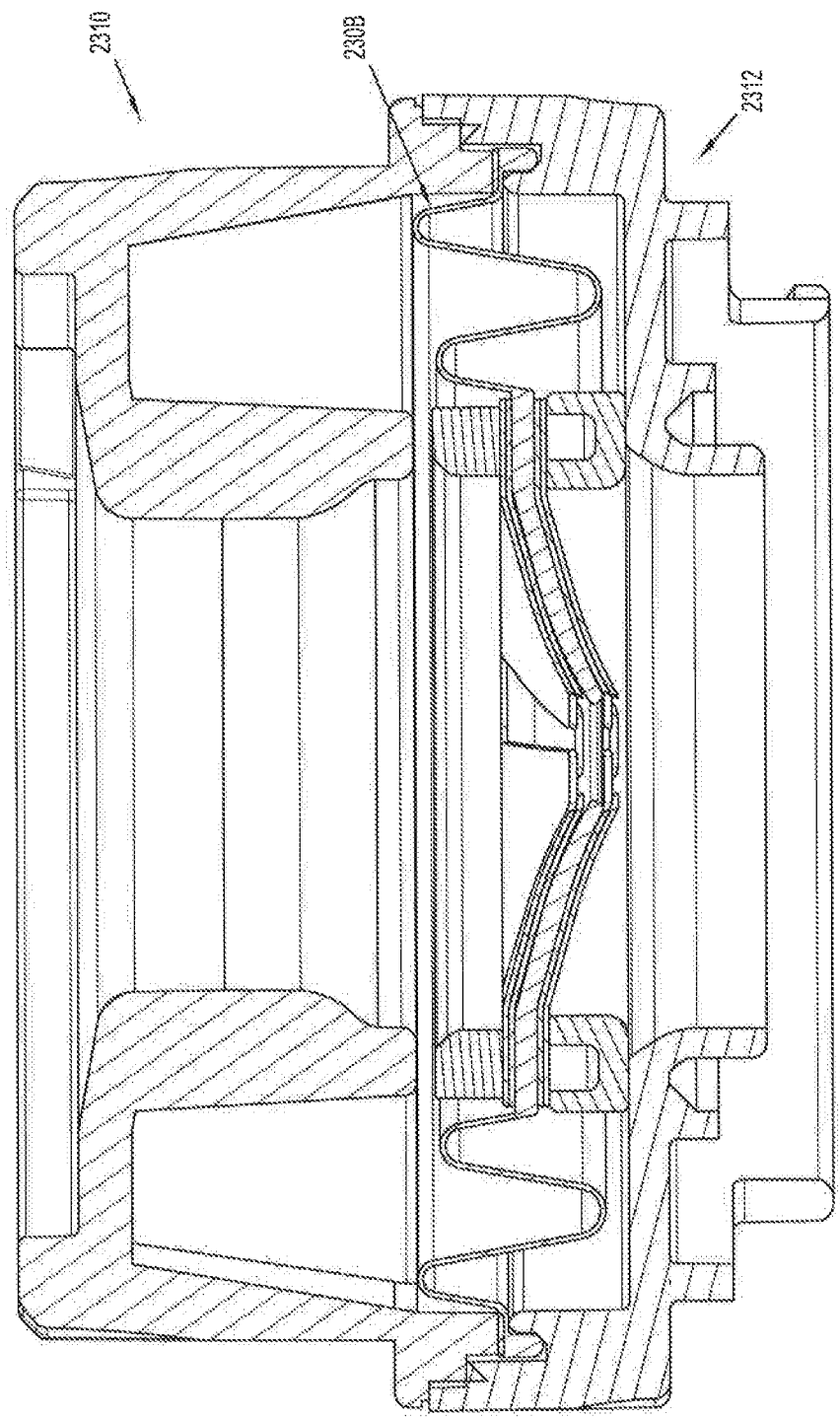
FIG. 5D is a cross-sectional view of the valve assembly of FIG. 5A assembled within the housing.

As shown in FIGS. 5B-5D, when instrument valve component 230B is assembled, first and second guard members 2140, 2142 are rotationally offset with respect to each other by 45 degrees (relative to the longitudinal axis), such that slits 2152 of first guard member 2140 and slits 2152' of second guard member 2142 are also rotationally offset from each other by 45 degrees (relative to the longitudinal axis). The rotational offset of first and second guard members 2140, 2142 with respect to each other provides for the plurality of curved guard portions 2141 of first guard member 2140 to span the width of slits 2152' of second guard member 2142, and for the plurality of curved guard portions 2141' of second guard member 2142 to span the width of slits 2152 of first guard member 2140.

Additionally, third and fourth guard members 2240, 2242 are rotationally offset with respect to each other by 45 degrees (relative to the longitudinal axis), such that slits 2252 of third guard member 2240 and slits 2252' of fourth guard member 2242 are also rotationally offset from each other by 45 degrees (relative to the longitudinal axis). The rotational offset of third and fourth guard members 2240, 2242 with respect to each other provides for the plurality of curved guard portions 2241 of third guard member 2240 to span the width of slits 2252' of fourth guard member 2242, and for the plurality of curved guard portions 2241' of fourth guard member 2242 to span the width of slits 2252 of third guard member 2240.

The rotational offset of first and second guard members 2140, 2142, as well as of third and fourth guard members 2240, 2242, with respect to each other discourages unwanted contact between, and thereby facilitates the protection of, septum seal 2160 when instrument valve component 230B is disposed within the housing of a cannula assembly 200 (FIG. 6) and an instrument is inserted and/or withdrawn through orifices 2166, 2144, 2144', 2244, 2244'.

Figure 6:
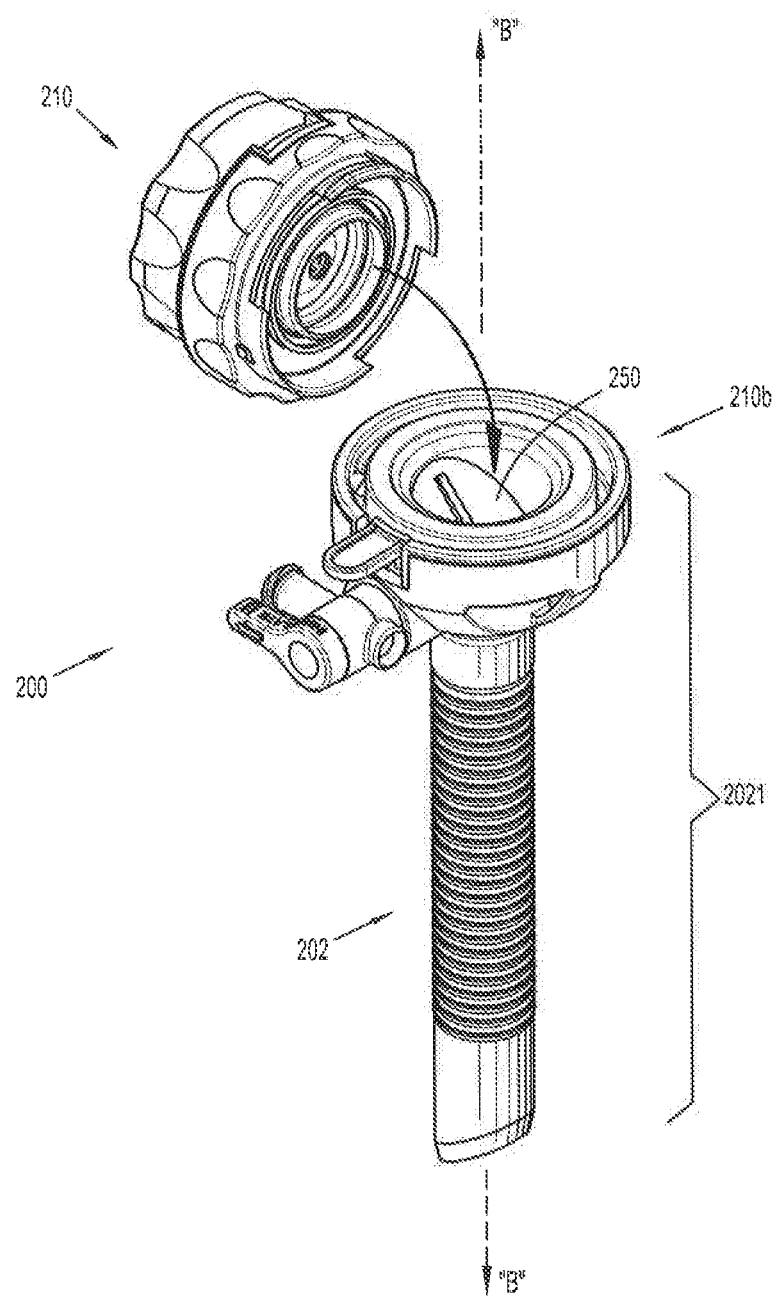
FIG. 6 is a perspective view of a cannula assembly showing a proximal housing component separated from a distal housing component.

Cannula assembly 200 will now be discussed in detail with reference to FIGS. 6-13. FIG. 6 illustrates instrument valve assembly 210 prior to its attachment to a representative distal cannula assembly, e.g., distal cannula assembly 2021. Distal cannula assembly 2021 includes an elongate tubular portion 202, defining a longitudinal axis "B-B" and a distal housing component 210b. Distal housing component 210b includes a zero-closure seal 250 that prevents the escape of insufflation gas when no instrument is present through the valve housing.

As previously mentioned, the instrument valve assembly 210 may be selectively attachable to, and detachable from, distal housing component 210b. Various different types of connection mechanisms can be employed in this regard, e.g., snap-fit, latches, bayonet coupling, threaded couplings, etc. FIGS. 7-8 illustrate one such connection mechanism, and specifically illustrate additional features, according to an embodiment of the present invention, by which instrument valve assembly 210 is selectively attachable to, and detachable from, distal housing component 210b.

Referring to FIG. 7, distal housing component 210b defines annular lips 1124, 1126 located on an inner surface of an obturator wall. Located circumferentially between lips 1124, 1126 is an annular channel 1301. In addition, distal housing component 210b also includes a radially outward user-actuatable portion 1508 of a rotation prevention mechanism 1500 (which will be described in greater detail below). Radially outward user-actuatable portion 1508 of rotation prevention mechanism 1500 is a tab 1507 that is integrally formed with an outer circumferential edge of distal housing component 210b. Tab 1507 further includes a radially-inward locking portion 1509. Tab 1507 is configured for resilient movement relative to distal housing component 210b about its point of attachment thereto, such that its user-actuatable portion 1508 is moveable distally relative to the circumferential edge of distal housing component 210b.

Referring to FIG. 8, second housing portion 2192 of instrument valve assembly 210 defines first and second annular recesses 1120, 1122 adjacent its distal end. Recesses 1120, 1122 are sized and shaped to receive annular lips 1124, 1126 of distal housing component 210b when distal housing component 210b and instrument valve assembly 210 are initially brought together in the axial direction. Located circumferentially between recesses 1120, 1122 of instrument valve assembly 210 are a pair of distal projections 1509. Likewise, distal projections 1509 are sized and shaped to be received by annular channel 1301 of distal housing component 210b when distal housing component 210b and instrument valve assembly 210 are initially brought together in the axial direction.

Second housing portion 2192 of instrument valve assembly 210 also has additional structures that engage with distal housing component 210b. For example, second housing portion 2192 of instrument valve assembly 210 also has structures that comprise a first component 1502 of rotation prevention mechanism 1500. These structures of instrument valve assembly 210 (e.g., the structures of first component 1502 of rotation prevention mechanism 1500) engage with the above-described structures of distal housing component 210b (e.g., the structures of radially outward user-actuatable portion 1508 of rotation prevention mechanism 1500), and enable distal housing component 210b and proximal housing component 210a, once initially brought together in the axial direction, to selectively attach and detach from each other via relative rotation of distal housing component 210b and proximal housing component 210a. For example, and referring to FIGS. 8 and 11, distal projections 1509 of instrument valve assembly 210 each include a rib 1200. Each distal projection 1509 also includes a groove 1299 located adjacent and proximal to its respective rib 1200. Additionally, each distal projection 1509 includes a stop 1210 (FIG. 8) adjacent each rib 1200. Also, distal projections 1509 include a first component 1502 of the above-referenced rotation prevention mechanism 1500. First component 1502 includes a protuberance 1503, having a ramped surface 1504 that is integrally formed on an outer circumferential surface of distal projection 1509.

Figure 9:
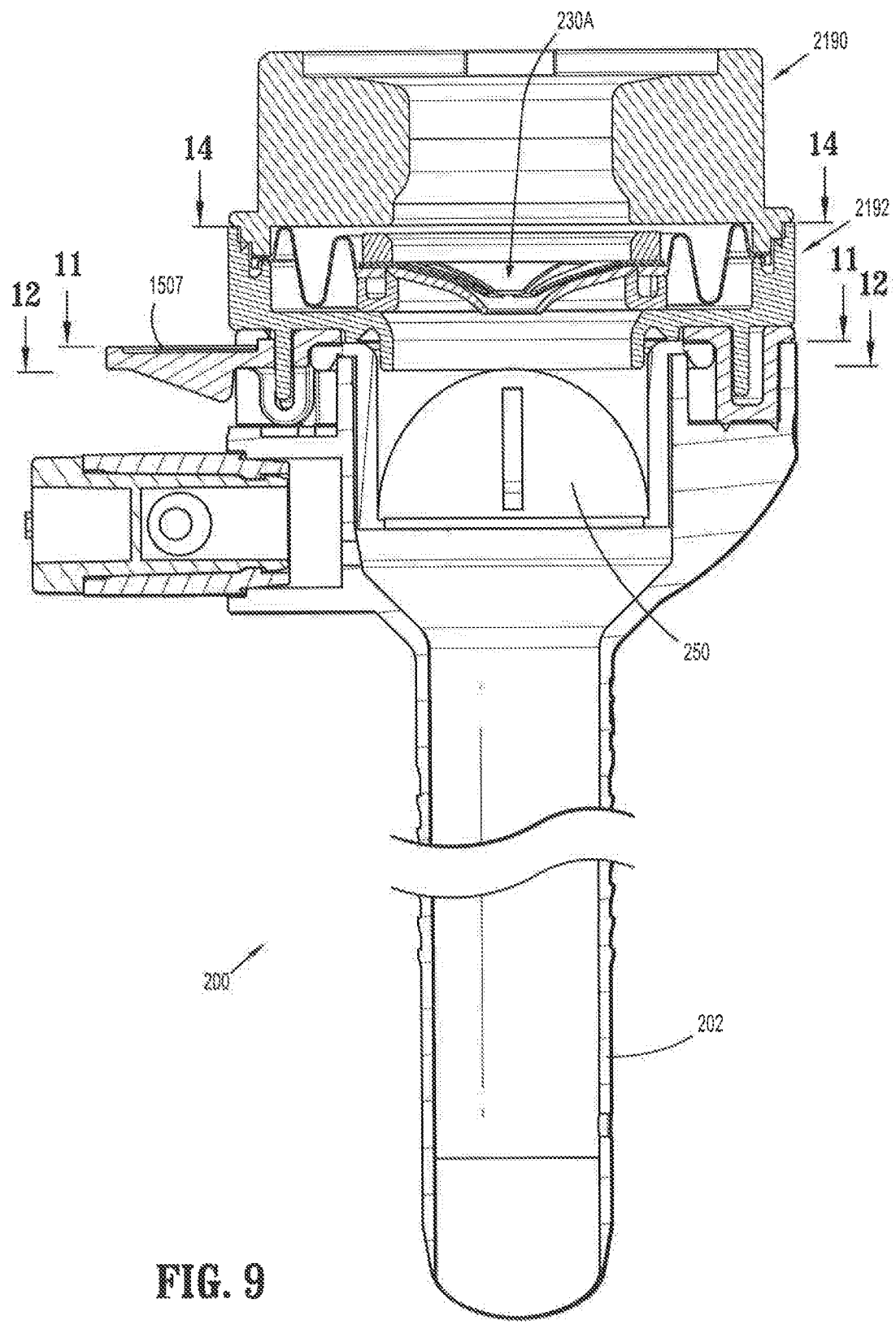
FIG. 9 is a cross-sectional view of the cannula assembly and the valve assembly of FIG. 3 illustrating the tab in a first position.
Figure 9A:
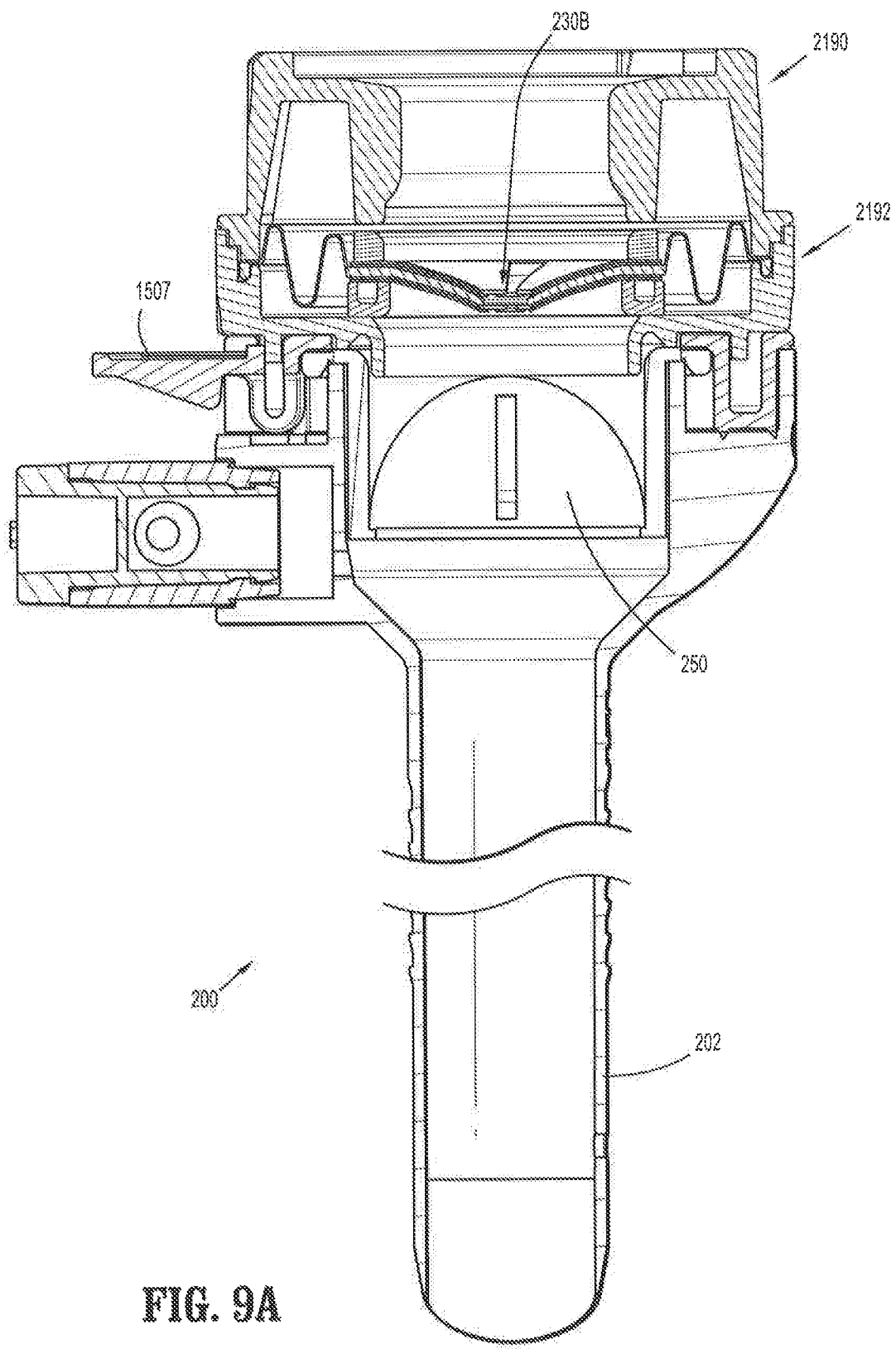
FIG. 9A is a cross-sectional view of the cannula assembly and the valve assembly of FIG. 5A illustrating the tab in a first position.
Figure 10:
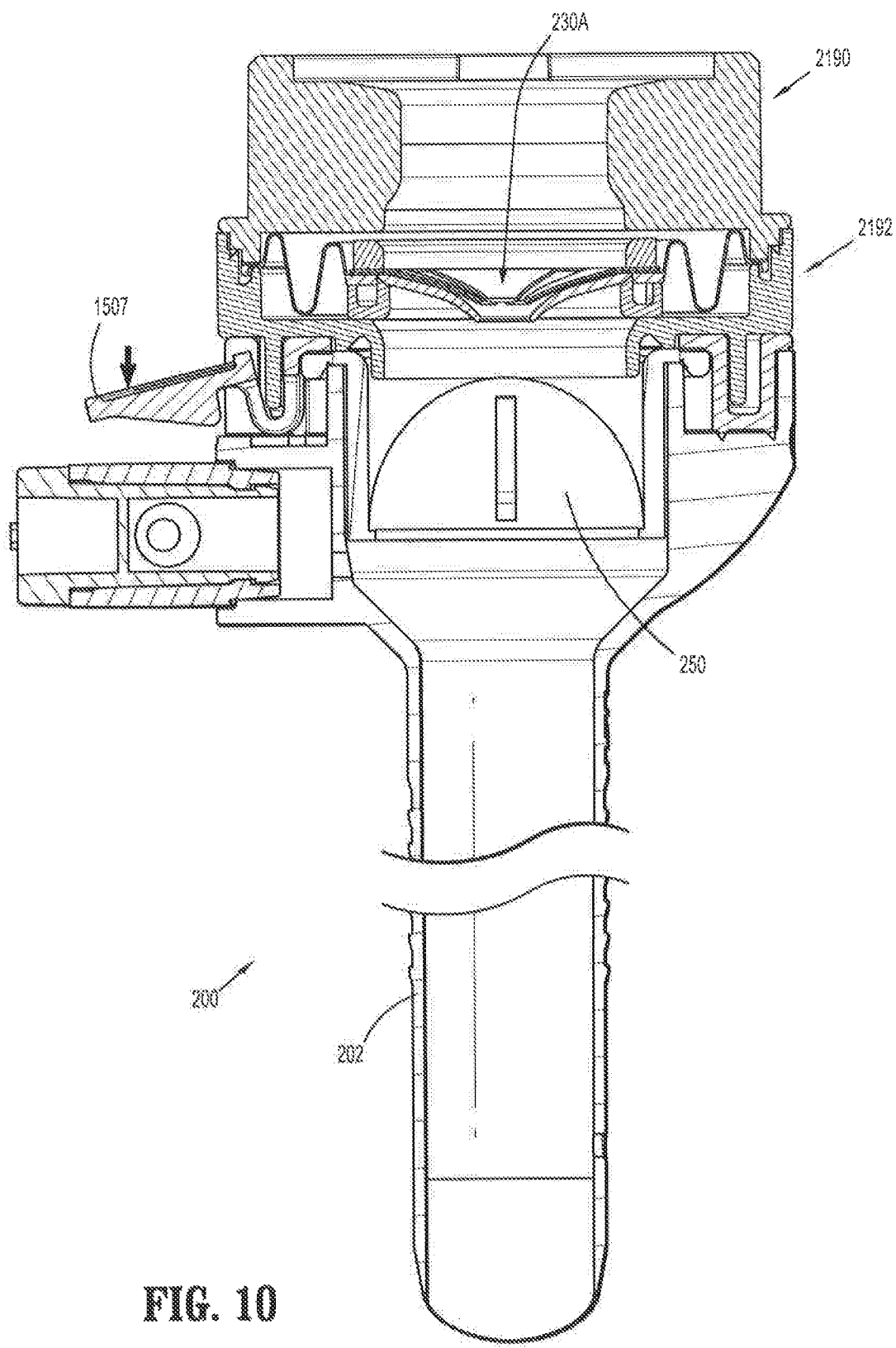
FIG. 10 is a cross-sectional view of the cannula assembly and the valve assembly of FIG. 3 illustrating the tab in a second position.

FIGS. 9 and 10 illustrate instrument valve assembly 210 (including first and second housing portions 2190, 2192, with instrument valve component 230A maintained therebetween) mounted on distal housing component 210b. It is noted that instrument valve component 230A may be replaced by instrument valve component 230B, as shown in FIG. 9A. In fact, instrument valve components 230A and 230B may be interchangeable throughout the exemplary embodiments described herein. In FIG. 9, tab 1507 is in a first, rest position. In this first position, relative rotation of instrument valve assembly 210 and distal housing component 210b (and thus decoupling of instrument valve assembly 210 and the distal housing component 210b) is prevented, as will be described in further detail below. In FIG. 10, tab 1507 is deflected, as by a user, into a second, actuated position. In this second position, relative rotation of instrument valve assembly 210 and distal housing component 210b (and thus decoupling of instrument valve assembly 210 and distal housing component 210b) is possible.

Figure 12:
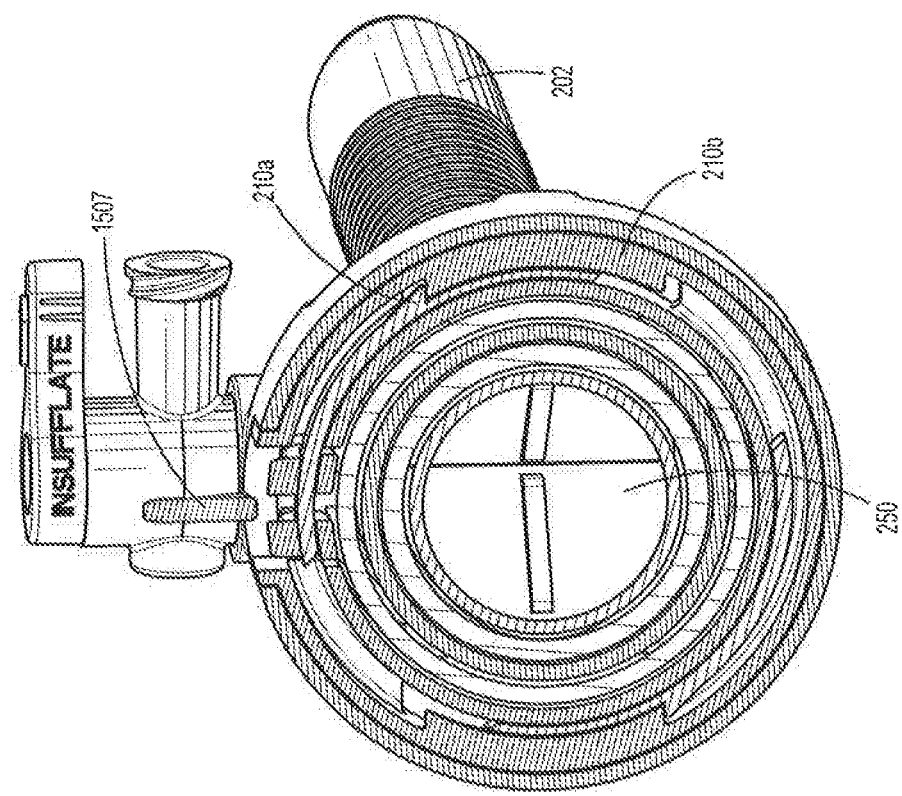
FIG. 12 is a cut-away perspective view taken along line 12-12 in FIG. 9.
Figure 11:
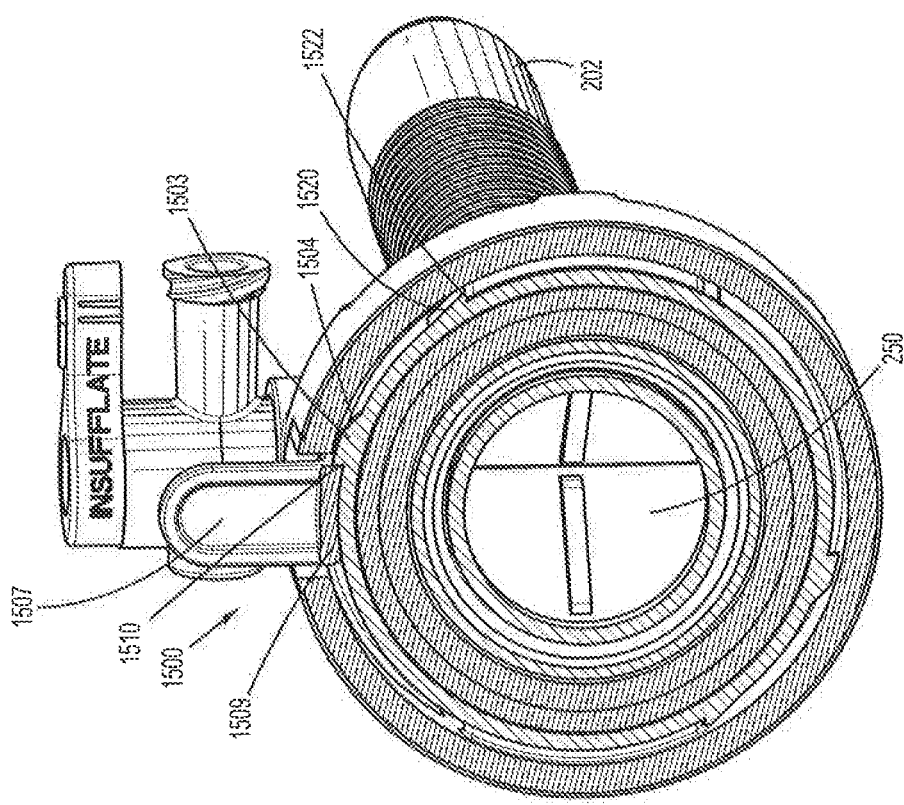
FIG. 11 is a cut-away perspective view taken along line 11-11 in FIG. 9.
Figure 13:
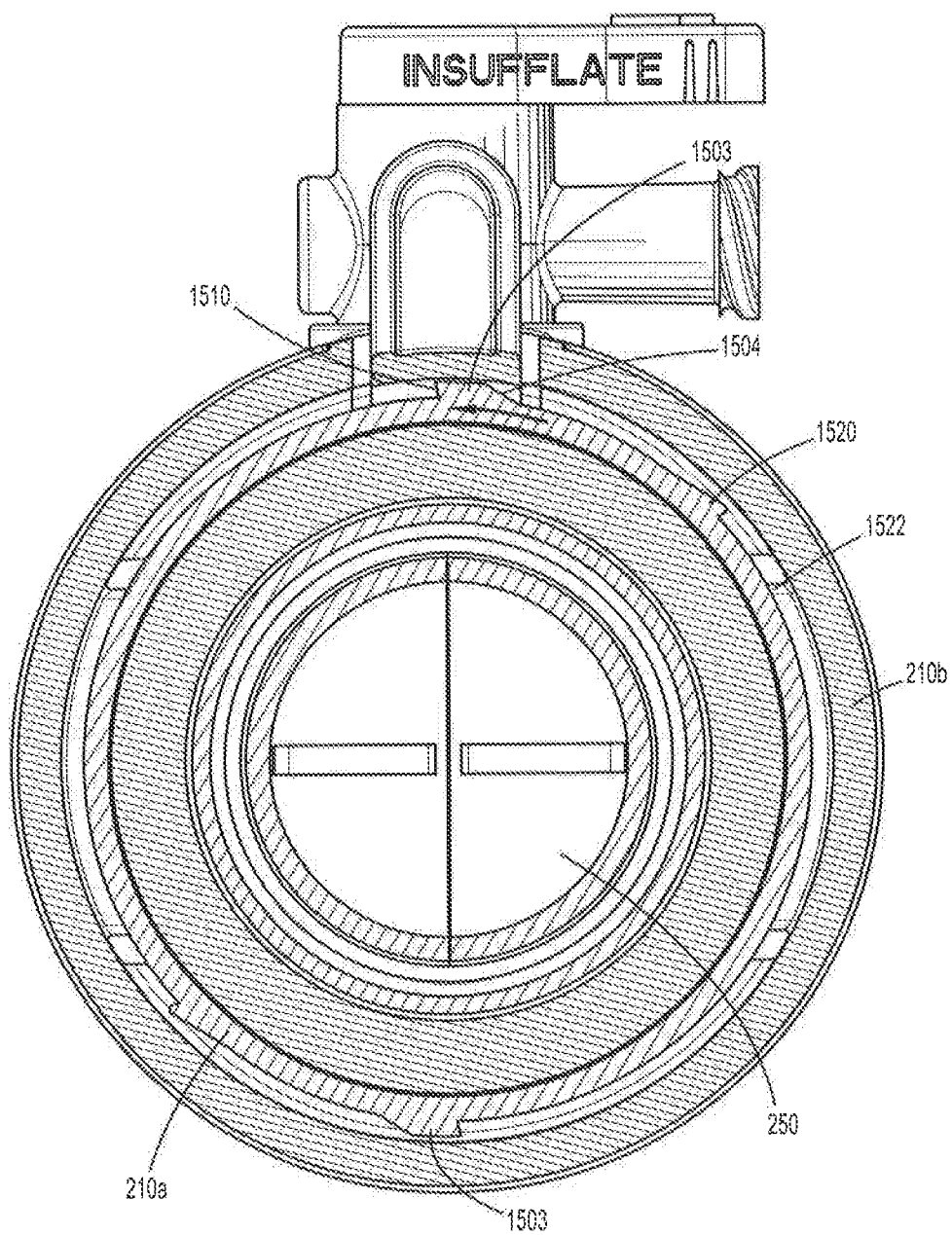
FIG. 13 is a cross-sectional view of a portion of the cannula assembly illustrating a portion of the proximal housing component engaging a portion of the distal housing component.

FIGS. 11 and 12 are cross-sectional views, taken along the lines 11-11 and 12-12, respectively, of FIG. 9, and illustrate the mating features of instrument valve assembly 210 and distal housing component 210b.

Rotation prevention mechanism 1500 prevents inadvertent relative rotation and thus potential decoupling of instrument valve assembly 210 and distal housing component 210b. Once instrument valve assembly 210 and distal housing component 210b are brought together axially, instrument valve assembly 210 may be rotated in a first direction (e.g., clockwise in the views of FIGS. 11-13), such that ramped surface 1504 of protuberance 1503 engages the locking portion 1509 of tab 1507. Continued rotation of instrument valve assembly 210 causes protuberance 1503 to exert a force directed in the radially outward direction on locking portion 1509 of tab 1507. The radially outward force is sufficient to cause tab 1507 to move radially outward relative to the circumferential edge of distal housing component 210b about its point of attachment thereto, from its first position towards its second position. Additionally, the radially outward force causes the user actuatable portion 1508 of tab 1507 to move distally. After a predetermined amount of rotation of proximal housing component 210a, protuberance 1503 passes tab 1507, and causes locking portion 1509 of tab 1507 to move back to its first position and adjacent to a perpendicular surface 1510 (FIGS. 11 and 13) of protuberance 1503. In this position, instrument valve assembly 210 is effectively prevented from counter-clockwise rotation with respect to distal housing component 210b.

Additionally, when sufficient rotation of instrument valve assembly 210 causes protuberance 1503 to pass tab 1507, protrusion 1520 (FIGS. 11 and 13) of instrument valve assembly 210 contacts a stop 1522 (FIGS. 11 and 13) of distal housing component 210b, thus effectively preventing additional clockwise rotation between instrument valve assembly 210 and distal housing component 210b. Accordingly, in the relative position of instrument valve assembly 210 and distal housing component 210b illustrated in FIG. 11, both directions of rotation of instrument valve assembly 210 are effectively prevented, and thus instrument valve assembly 210 is rotationally fixed with respect to distal housing component 210b. Annular lips 1124, 1126 of distal housing component 210b are positioned within the respective grooves 1299 of the distal projections of instrument valve assembly 210, and are maintained in the grooves by ribs 1200, thereby also preventing instrument valve assembly 210 and distal housing component 210b from moving axially relative to each other. In this manner, rotation prevention mechanism 1500 prevents instrument valve assembly 210 from inadvertently rotating relative to, and thus inadvertently becoming disconnected from distal housing component 210b once instrument valve assembly 210 reaches this locked position.

To remove instrument valve assembly 210 from distal housing component 210b, a user exerts a force on tab 1507 directed in the distal direction, as shown in FIG. 10. A sufficient amount of distally-directed force causes the user actuatable portion 1508 of tab 1507 to move distally relative to the circumferential edge of distal housing component 210b about its point of attachment thereto until locking portion 1509 of tab 1507 is located radially outward of protuberance 1503. In this position, instrument valve assembly 210 is no longer prevented from rotating, but rather is free to rotate, in a second direction (e.g., counter-clockwise as shown by the arrow in FIG. 13) relative to distal housing component 210b. In this manner, rotation prevention mechanism 1500 provides a selectively actuatable mechanism that, when actuated, enables a user to rotate and thereby disconnect instrument valve assembly 210 from distal housing component 210b.

Figure 14:
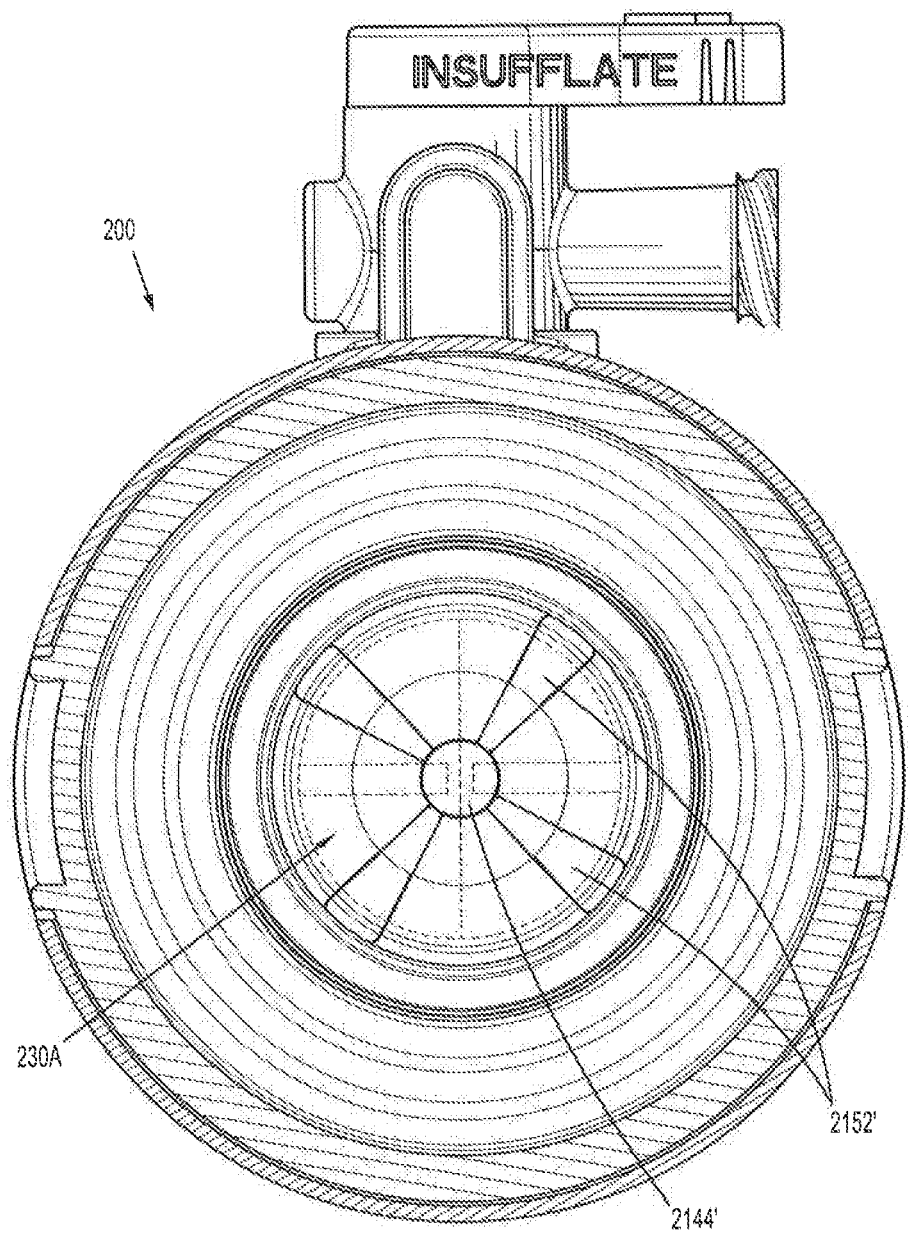
FIG. 14 is a cross-sectional view of a portion of the cannula assembly illustrating the valve assembly radially centered within the housing taken along line 14-14 in FIG. 9.
Figure 15:
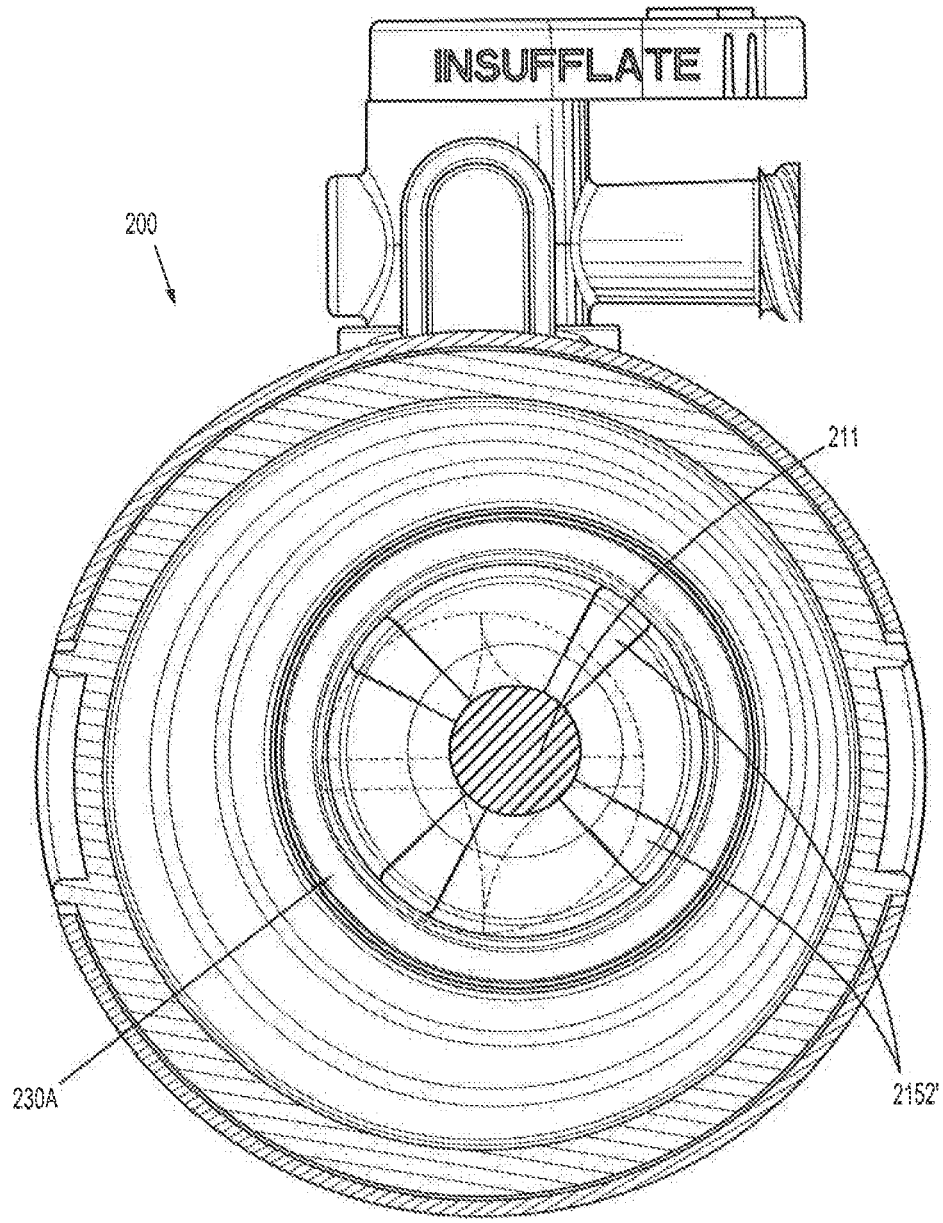
FIG. 15 is a cross-sectional view of a portion of the cannula assembly illustrating an instrument inserted through the valve assembly, and the valve assembly being rotationally offset within the housing.

FIGS. 14 and 15 illustrate the operation of the instrument valve assembly 210 in use during surgery. FIG. 14 illustrates instrument valve assembly 210 in a rest position, while FIG. 15 illustrates instrument valve assembly 210 having a surgical instrument 211 inserted therethrough in an off-axis position. As shown in FIG. 15, when an instrument is moved through instrument valve assembly 210, the elastomeric material of septum seal 2160 is protected by the first and second guard members 2140, 2142. For example, because the width of each one of the plurality of curved guard portions 2141 of first guard member 2140 is wider than slits 2152' of second guard member 2142 when instrument valve component 230A is in the rest position, movement of instrument 211 through orifice 2166 of septum seal 2160 insures that at least one of the plurality of curved guard portions 2141 of first guard member 2140 prevents instrument 211 from tearing seal 2160 directly beneath slits 2152'. As noted above, instrument valve component 230B may be substituted for instrument valve component 230A. In fact, instrument valve components 230A and 230B may be interchangeable throughout the exemplary embodiments described herein.

Likewise, because the width of each one of the plurality of curved guard portions 2141' of second guard member 2142 is wider than slits 2152 of first guard member 2140 when instrument valve component 230A is in the rest position, movement of instrument 211 through orifice 2166 of septum seal 2160 insures that the instrument contacts at least one of the plurality of curved guard portions 2141' of second guard member 2142 rather than directly contacting, and potentially tearing, the elastomeric material of septum seal 2160 directly beneath the slits 2152. Still further, the width of each one of the plurality of curved guard portions 2141, 2141' is sufficiently greater than the respective slits 2152, 2152' which they span, such that as the curved guard portions 2141, 2141' spread apart as an instrument is inserted therethrough, thereby widening the slits 2152, 2152', as well as still cover their respective slits 2152, 2152'. This reduces the likelihood that an inserted instrument will inadvertently contact and tear the elastomeric material of the seal and allows the arrangement to accommodate a variety of different sized instruments.

In addition, by virtue of the bellows arrangement, orifice 2166 of septum seal 2160 may be moved to an off-center location (FIG. 15) with minimal force, thereby reducing the likelihood that the elastomeric material of septum seal 2160 directly around orifice 2166 is caused to cat-eye and leak by such off-axis movement. In addition, upon removal of the instrument, the bellowed arrangement helps to urge orifice 2166 back towards the radial center of instrument valve component 230A, such that orifice 2166 is in a centered location for reception of a subsequently-inserted surgical instrument. Urging orifice 2166 back towards the radial center of instrument valve component 230A prior to reception of a subsequently-inserted surgical instrument increases the likelihood that the subsequently-inserted surgical instrument is received by orifice 2166 and reduces the likelihood that the subsequently-inserted surgical instrument tears the elastomeric material of septum seal 2160.

As set forth above, various different types of obturators, e.g., bladed, bladeless, blunt, optical, non-optical, etc. may be employed in the trocar assemblies of the present invention. Several of these types are described in additional detail hereinbelow, although it should be recognized that various other types of obturators may be employed, e.g., obturators having structure, e.g., tip geometries, other than those shown.

Figure 16:
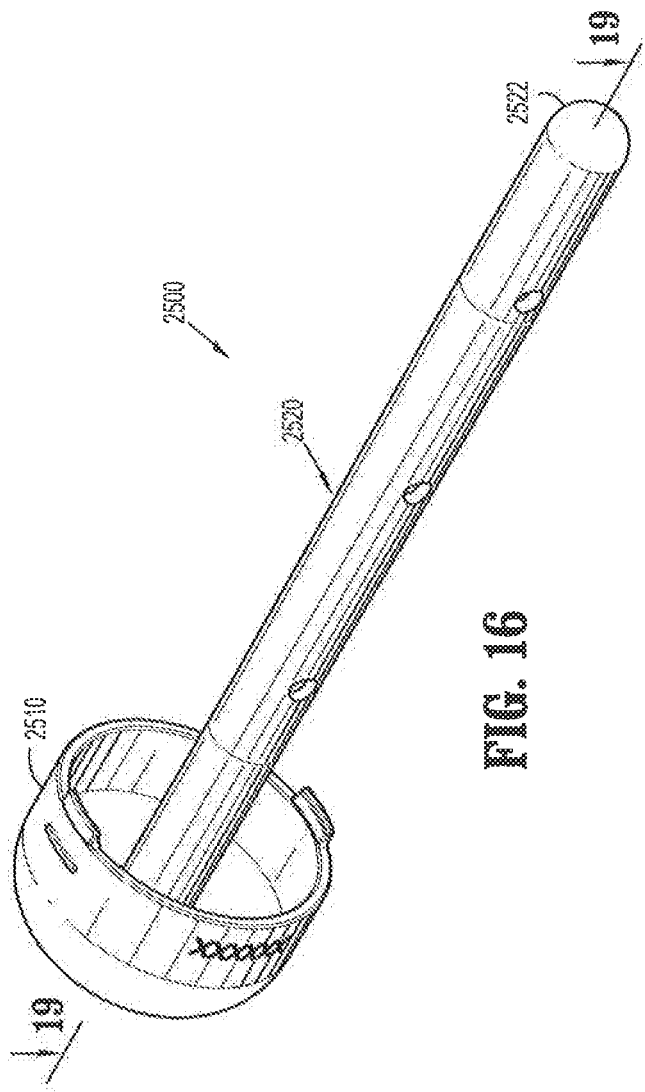
FIG. 16 is a perspective view of a first embodiment of an obturator for separating tissue planes in an endoscopic surgical procedure.
Figure 17:
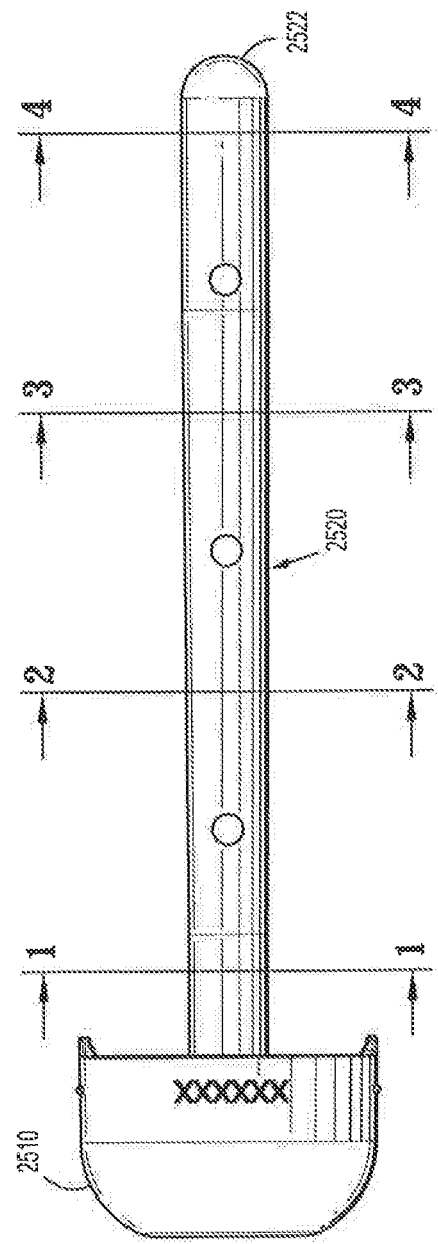
FIG. 17 is a side view of the obturator of FIG. 16.

Referring to FIGS. 16-21, a first example embodiment of a blunt obturator for separating tissue planes in an endoscopic surgical procedure is shown and described. With reference to FIGS. 16 and 17, obturator 2500 includes an obturator housing 2510 and an elongate shaft 2520. Elongate shaft 2520 includes a proximal end, a distal end, and a tubular member therebetween. Proximal end of elongate shaft 2520 may be connected, e.g., snap-fit, welded, etc., to obturator housing 2510 and extends proximally out of the proximal end of a cannula housing 2504 (FIG. 21) when obturator 2500 is fully positioned therewithin. The distal end of elongate shaft 2520 extends distally out of a distal end 2502a of a cannula tube 2502 (FIG. 21) when obturator 2500 is positioned therewithin. The distal end of elongate shaft 2520 includes a member 2522 that closes the distal end of elongate shaft 2520. Member 2522 is adapted for blunt tissue dissection and includes a hemispherical outer surface that functions to help separate tissue along natural tissue planes. The hemispherical outer surface of the distal end defines a radius of curvature dimensioned to be atraumatic to tissue. Elongate shaft 2520 and member 2522 are monolithically fabricated from any suitable material such as an acrylonitrile butadiene styrene plastic material ("ABS") that may be opaque. Obturator housing 2510 and/or member 2522 may additionally or alternatively be fabricated from a material that is transparent or translucent.

FIGS. 17A-17D delineate cross-sections of elongate shaft 2520 as taken through the plurality of corresponding section lines. FIGS. 17A-17D illustrate the cross-sections taken along lines 1-1, 2-2, 3-3, and 4-4 through elongate shaft 2520 are circular.

Figure 18:
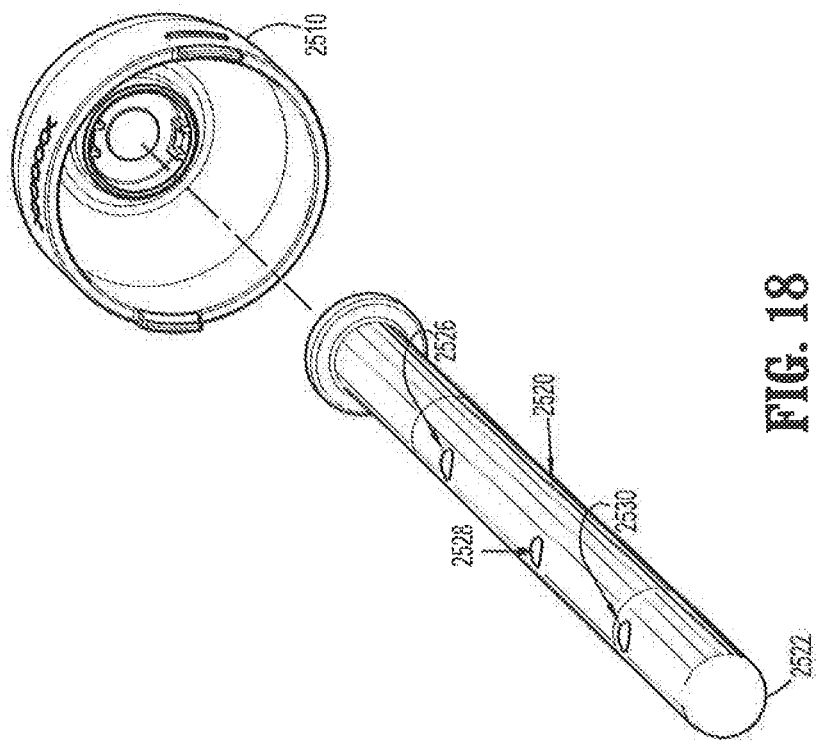
FIG. 18 is a perspective view of the obturator with parts separated.
Figure 17B:
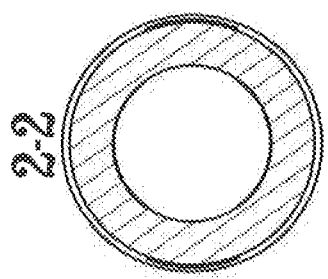
FIGS. 17A-17D show cross-sections of the elongate shaft taken along lines 1-1, 2-2, 3-3, and 4-4 of the obturator of FIG. 16.
Figure 17D:
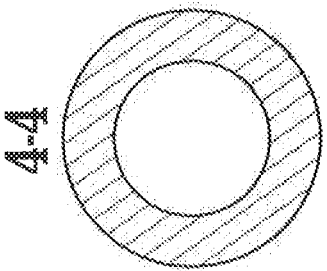
Figure 17A:
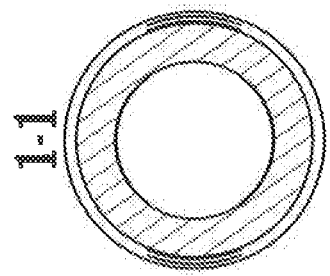
Figure 17C:
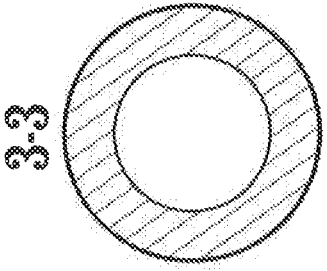

With reference to FIGS. 18-20, elongate shaft 2520 has an inner surface 2520a and an outer surface 2520b that define an obturator wall 2520c. Inner surface 2520a defines a central bore 2524 that extends through the tubular member from the proximal end of elongate shaft 2520 to an arcuate surface 2520d at a distal end of inner surface 2520a.

The tubular portion of elongate shaft 2520 includes a pair of proximal apertures 2526, a pair of intermediate apertures 2528, and a pair of distal apertures 2530. Each aperture 2526, 2528, and 2530 extends through inner and outer surfaces 2520a, 2520b of elongate shaft 2520. When obturator 2500 is fully positioned within cannula 2550, apertures 2526, 2528, and 2530 are all positioned within, and covered by, cannula tube 2502 of cannula 2550 (FIG. 21).

In operation, member 2522 enables initial insertion of obturator 2500 within an opening in tissue, e.g., a pre-cut scalpel incision. Member 2522 facilitates advancement of obturator 2500 between tissue layers to gently dissect tissue and enlarge the opening without any cutting or incising of the tissue.

As illustrated above in FIG. 21, obturator 2500 is disposed within a cannula 2550. Cannula 2550 includes cannula tube 2502 extending distally from cannula housing 2504. Obturator housing 2510 is releasably coupled to cannula housing 2504. When obturator 2500 is coupled to cannula 2550, a portion of elongate shaft 2520 and member 2522 extend distally beyond distal end 2502a of cannula tube 2502. Each of the apertures (2526, 2528, and 2530) is positioned within cannula tube 2502 and proximal of distal end 2502a of cannula tube 2502.

Referring to FIGS. 22-30, a second embodiment of an obturator for separating tissue planes in an endoscopic surgical procedure is presented.

With reference to FIG. 22, obturator 2600 includes an elongate shaft 2612 having a proximal end 2612a, a distal end 2612b, and a tubular member extending therebetween. Although not shown in these figures, the obturator 2600 may also include a handle or housing, e.g., like the housing of 2510 of the obturator 2500. Referring additionally to FIG. 26, elongate shaft 2612 includes an inner surface 2612c and an outer surface 2612d that define an obturator wall 2612e. With reference also to FIGS. 28 and 29, a bore 2614 originates at proximal end 2612a and extends into elongate shaft 2612 to an arcuate surface 2612f (FIG. 28) at a distal end of inner surface 2612c.

With reference again to FIGS. 26 and 27, the tubular portion of elongate shaft 2612 includes a pair of proximal apertures 2616, a pair of intermediate apertures 2618, and a pair of distal apertures 2620. Each aperture 2616, 2618, and 2620 extends through inner and outer surfaces 2612c, 2612d of elongate shaft 2612. When obturator 2600 is fully positioned within cannula 2650, apertures 2616, 2618, and 2620 are all positioned within, and covered by, cannula tube 2602 of cannula 2650 (FIG. 30).

Referring again to FIG. 23, a distal portion of elongate shaft 2612 includes a member 2622. Elongate shaft 2612 and member 2622 may be monolithically fabricated from any suitable material such as an acrylonitrile butadiene styrene plastic material ("ABS") that may be opaque. Elongate shaft 2612 and/or member 2622 may additionally or alternatively be fabricated from a material that is transparent or translucent.

Figure 24:
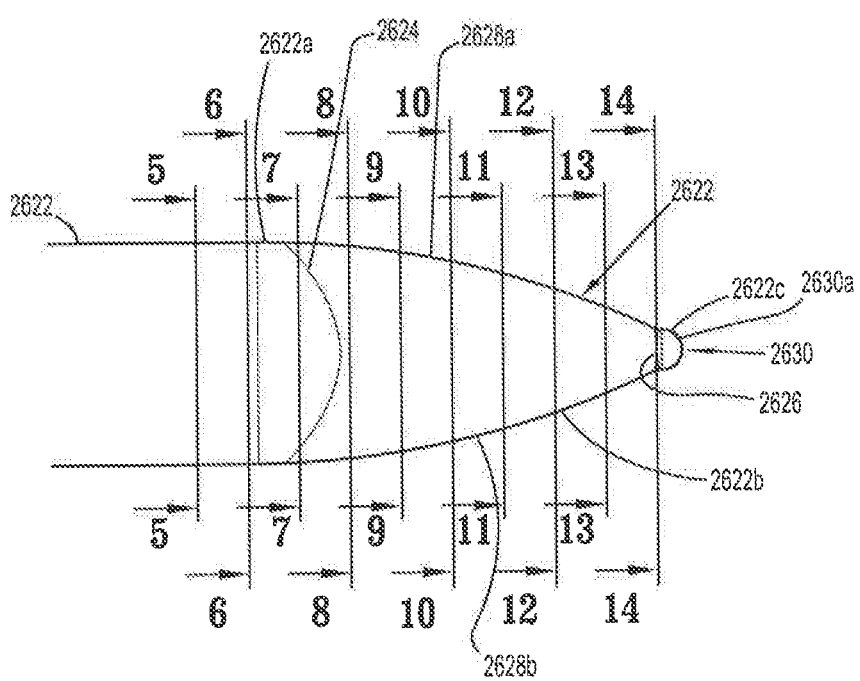
FIG. 24 is an enlarged top view of the distal portion of the elongate shaft of FIG. 23.
Figure 24A:
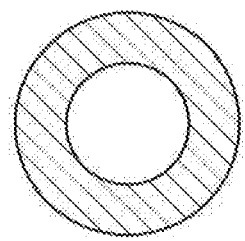
FIGS. 24A-24J show cross-sections of the distal portion taken along lines 5-5, 6-6, 7-7, 8-8, 9-9, 10-10, 11-11, 12-12, 13-13, and 14-14.
Figure 24B:
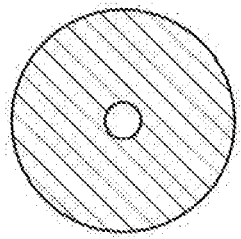
Figure 24C:
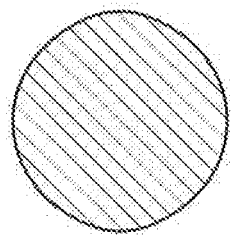
Figure 24D:
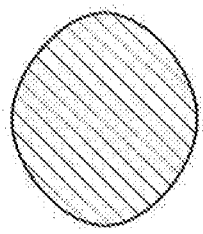
Figure 24E:
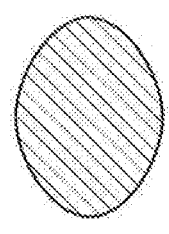
Figure 24F:
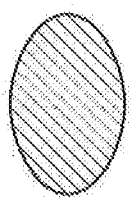
Figure 24G:
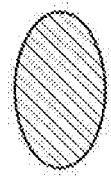
Figure 24H:
Figure 24I:
Figure 24J:

Referring to FIG. 24, an enlarged top view of the distal portion of elongate shaft 2612 is illustrated. This top view is rotationally offset 90 degrees relative to an enlarged side view of a distal portion of elongate shaft 2612 depicted in FIG. 25. As seen in FIGS. 24 and 25, member 2622 includes a proximal section 2622a, a central section 2622b, and an atraumatic guiding nub 2622c. An imaginary line 2624 (shown to illustrate curvature) separates proximal section 2622a and central section 2622b. Similarly, an imaginary line 2626 (shown to illustrate curvature) separates central section 2622b and atraumatic guiding nub 2622c.

Central section 2622b extends distally from proximal section 2622a such that, together, proximal and central section's 2622a, 2622b include a pair of diametrically opposed outer surfaces 2628a, 2628b. Each of opposed outer surfaces 2628a, 2628b is generally convex. Atraumatic guiding nub 2622c extends distally from central section 2622b and includes a rounded end 2630. Rounded end 2630 defines a radius of curvature dimensioned to be atraumatic to tissue. More specifically, rounded end 2630 includes rounded outer surfaces 2630a that function to help separate tissue along natural tissue planes. Proximal section 2622a includes a pair of diametrically opposed outer surfaces 2632a, 2632b. Each of opposed outer surfaces 2632a, 2632b is generally convex. Central section 2622b includes a pair of diametrically opposed concave outer surfaces 2634a, 2634b that are positioned between the pair of diametrically opposed outer surfaces 2632a, 2632b of proximal section 2622a and rounded outer surfaces 2630a of rounded end 2630.

FIGS. 24A-24J delineate a plurality of lines of cross-section. FIGS. 24A-24J show the cross-sections taken along lines 5-5 and 6-6 of distal portions of elongate shaft 2612, which are circular, the cross-sections taken along lines 7-7 of proximal section 2622a and 8-8 of central section 2622b, which are generally circular or irregular shape, the cross-sections taken along lines 9-9, 10-10, 11-11, 12-12, and 13-13 of central section 2622b, which are oval or generally oval shapes, and the cross-section taken along line 14-14 through atraumatic guiding nub 2622c, which is circular. The length from cross-section 9-9 through cross-section 13-13 is less than one-half of the overall length of the member 2622. Thus, the majority of the length of member 2622 is either circular or irregularly shaped.

In operation, atraumatic guiding nub 2622c enables initial insertion of obturator 2600 within an opening in tissue, e.g., a pre-cut scalpel incision, and facilitates advancement of member 2622 between tissue layers to gently dissect tissue without any cutting or incising of the tissue. After initial insertion and continued distal insertion, central section 2622b and proximal section 2622a continue to gently enlarge the opening in tissue.

As illustrated above in FIG. 30, obturator 2600 is disposed within a cannula 2650. Cannula 2650 includes cannula tube 2652 extending distally from cannula housing 2604. Obturator housing 2610 is releasably coupled to cannula housing 2604. When obturator 2600 is coupled to cannula 2650, a portion of elongate shaft 2612 and member 2622 extend distally beyond distal end 2652a of cannula tube 2652. Each of the apertures (2616, 2618, and 2620) is positioned within cannula tube 2652 and proximal of distal end 2652a of cannula tube 2652. Obturator housing 2610 may be made from any suitable material such as ABS and may be opaque and may be welded to elongate shaft 2612.

Referring to FIGS. 31-37, a third embodiment of an obturator for separating tissue planes in an endoscopic surgical procedure is presented.

With reference to FIGS. 31 and 32, obturator 2700 includes an obturator housing 2710 and an elongate shaft 2720. Elongate shaft 2720 includes a proximal end, a distal end, and a tubular member extending therebetween. The proximal end of elongate shaft 2720 may be welded or otherwise fixedly attached to obturator housing 2710 and extends proximally out of the proximal end of a cannula housing 2704 (FIG. 37) when the obturator is fully positioned therewithin. The distal end of elongate shaft 2720 extends distally out of a distal end 2752a of a cannula tube 2752 (FIG. 37) when the obturator is positioned therewithin. The distal end of elongate shaft 2720 includes a member 2722 that closes the distal end of elongate shaft 2720. Member 2722 is adapted for blunt tissue dissection. Elongate member 2720 and member 2722 may be monolithically fabricated from any suitable material such as acrylonitrile butadiene styrene plastic material ("ABS") that may be opaque. Obturator housing 2710 may be fabricated from any suitable material such as ABS that may be opaque. Member 2722 includes a proximal section 2722a and a rounded tip 2722b that extends distally from proximal section 2722a. Proximal section 2722a has a frustoconical shape. Rounded tip 2722b includes rounded outer surfaces that function to help separate tissue along natural tissue planes and define a radius of curvature dimensioned to be atraumatic to tissue.

Figure 33:
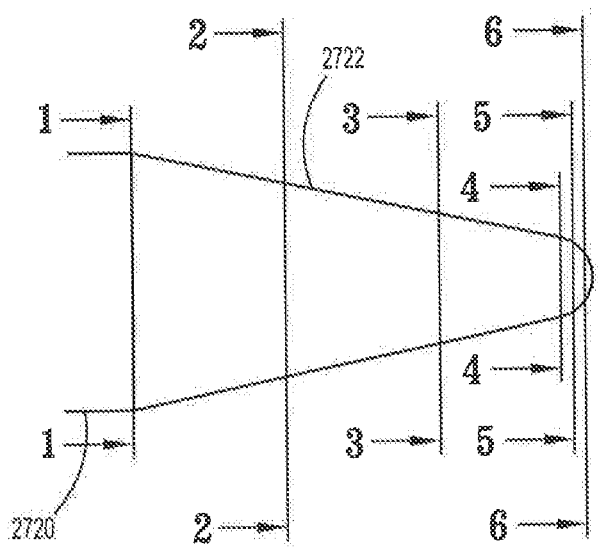
FIG. 33 is an enlarged top view of the distal portion of the elongate shaft of the obturator of FIG. 31.
Figure 33A:
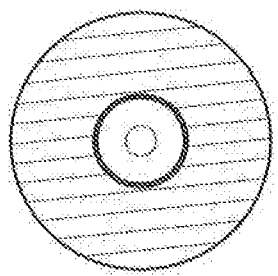
FIGS. 33A-33F show cross-sections of the distal portion taken along lines 1-1, 2-2, 3-3, 4-4, 5-5, and 6-6.
Figure 33B:
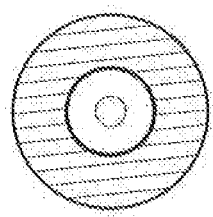
Figure 33C:
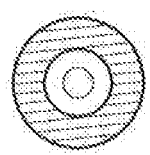
Figure 33D:
Figure 33E:
Figure 33F:

FIG. 33 is an enlarged side view illustrating a distal end portion of elongate shaft 2720 including member 2722. FIGS. 33A-33F illustrate cross-sections of elongate shaft 2720 as taken through the plurality of corresponding section lines. In particular, the cross-sections taken along lines 1-1, 2-2, 3-3, 4-4, 5-5, and 6-6 through member 2722 of elongate shaft 2720 are circular.

With reference to FIGS. 34-36, elongate shaft 2720 has an inner surface 2720a and an outer surface 2720b that define and obturator wall 2720c. Inner surface 2720a defines a central bore 2724 that extends through the tubular member from the proximal end of elongate shaft 2720 to a frustoconcial surface 2720d having an arcuate end surface 2720e at a distal end of inner surface 2720a.

Figure 37:
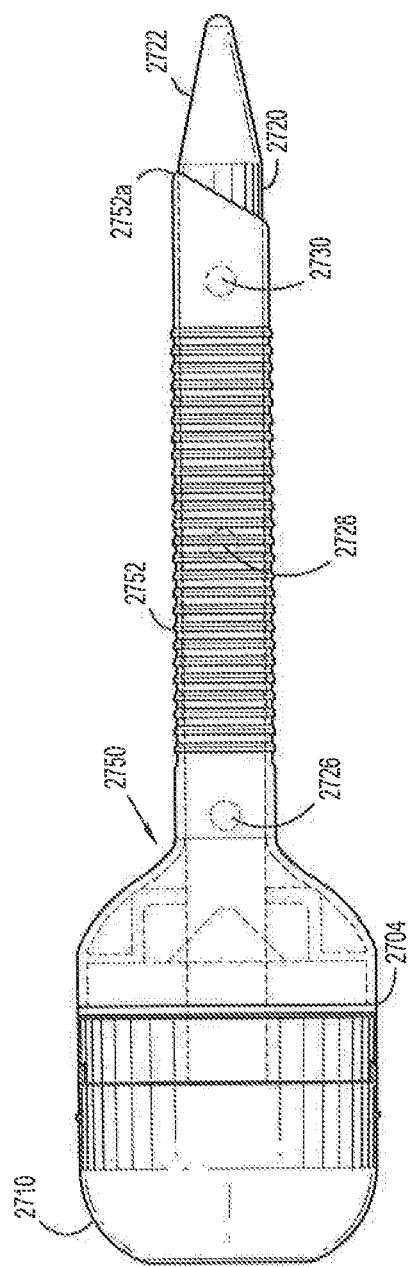
FIG. 37 is side view of the obturator of FIG. 31 inserted through a cannula.

The tubular portion of elongate shaft 2720 includes a pair of proximal apertures 2726, a pair of intermediate apertures 2728, and a pair of distal apertures 2730. Each aperture 2726, 2728, and 2730 extends through inner and outer surfaces 2720a, 2720b of elongate shaft 2720. When obturator 2700 is fully positioned within cannula 2750, apertures 2726, 2728, and 2730 are all positioned within, and covered by, cannula tube 2752 of cannula 2750 (FIG. 37).

In operation, rounded tip 2722b enables initial insertion of obturator 2700 within an opening in tissue, e.g., a pre-cut scalpel incision, and facilitates advancement of member 2722 between tissue layers to gently dissect tissue without any cutting or incising of the tissue. After initial insertion and continued distal insertion, proximal section 2722a continues to gently enlarge the opening in tissue.

As illustrated below in FIG. 37, obturator 2700 is disposed within a cannula 2750. Cannula 2750 includes cannula tube 2752 extending distally from cannula housing 2754. Obturator housing 2710 is releasably coupled to cannula housing 2704. When obturator 2700 is coupled to cannula 2750, a portion of elongate shaft 2720 and member 2722 extend distally beyond distal end 2752a of cannula tube 2752. Each of the apertures (2726, 2728, and 2730) is positioned within cannula tube 2752 and proximal of distal end 2752a of cannula tube 2752.

Figure 38A:
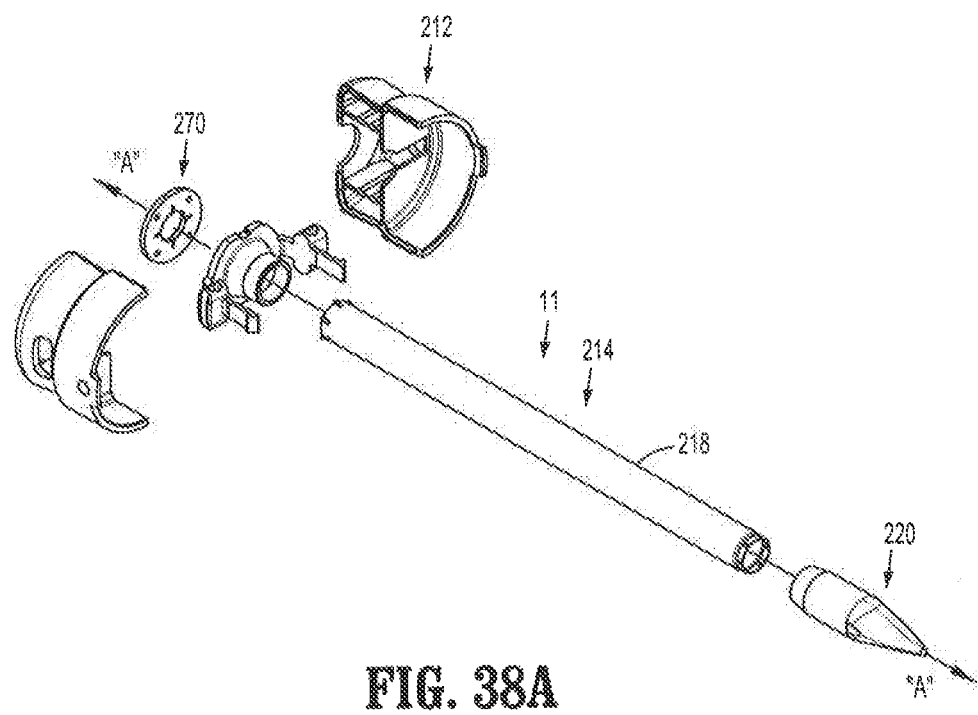
FIG. 38A is an exploded view of an obturator assembly, in accordance with an example embodiment of the present invention.
Figure 38B:
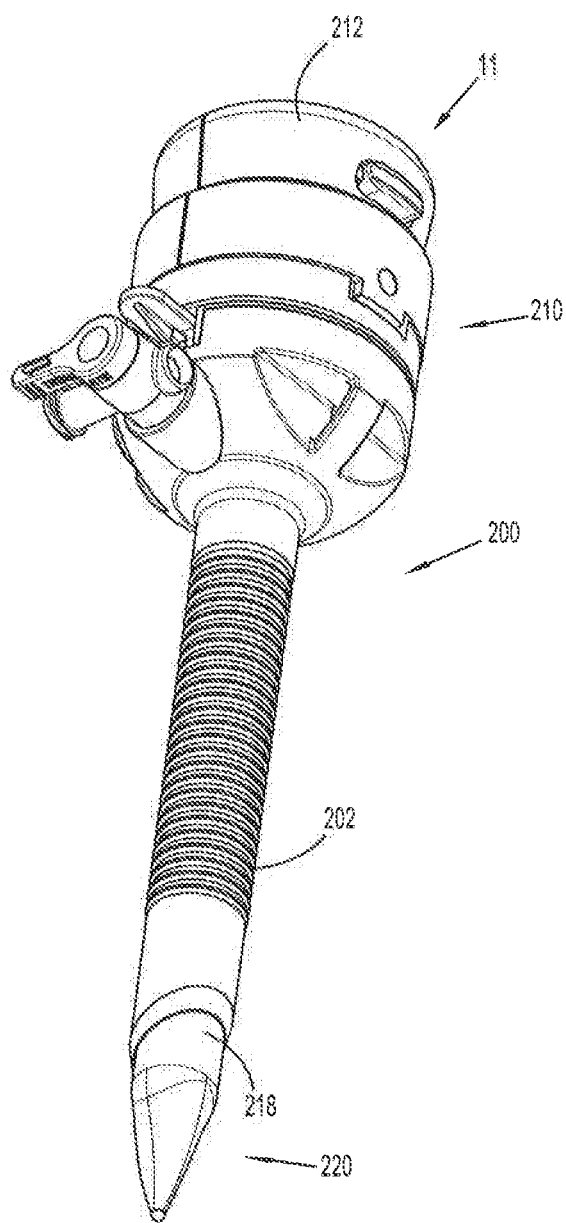
FIG. 38B is a perspective view of a surgical access system, with the obturator of FIG. 38A shown inserted therein, in accordance with an embodiment of the present invention.
Figure 39:
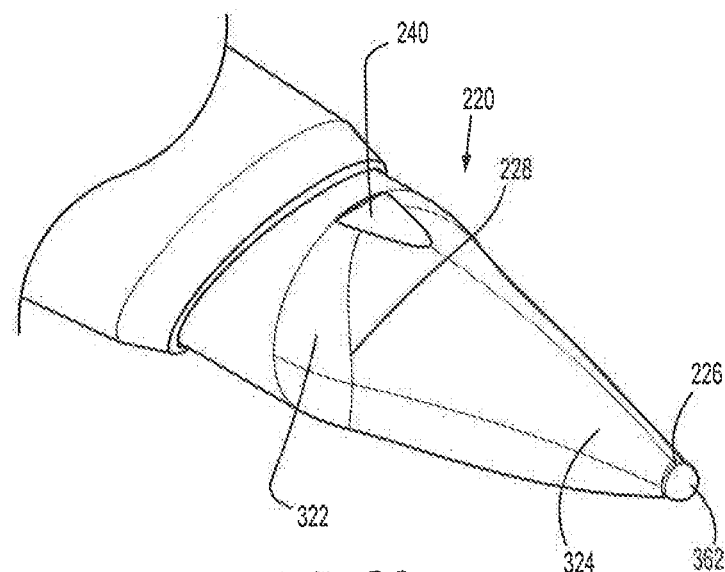
FIG. 39 is a perspective view of a distal end of the surgical access system of FIG. 38B.

FIGS. 38A-45 illustrate still another embodiment of the present invention. FIG. 38A is an exploded view of an obturator assembly 11, in accordance with an example embodiment of the present invention. FIG. 38B is a perspective view of a surgical access system 10 in which such an obturator is employed. In this embodiment, the obturator is an example of a bladeless optical obturator, which allows visualization during entry via an endoscope inserted into the obturator.

In this embodiment, the system 10 includes an obturator assembly 11 and a cannula assembly 200 which at least partially receives the obturator assembly 11. The obturator assembly 11 includes an obturator housing 212 disposed in mechanical cooperation with an elongated obturator member 214, and defines a longitudinal axis "A-A." The elongated obturator member 214 extends distally from the obturator housing 212.

The obturator member 214 includes an obturator shaft 218 mechanically coupled to the obturator housing 212, and an optical member 220 at the distal end of the obturator shaft 218. The obturator shaft 218 is made from either steel or a polymeric material. The optical member 220, which includes a hollow interior, includes a proximal section 322, a central section 324, and an atraumatic guiding nub 226. In use, a distal viewing tip of an endoscope is brought into engagement with a sloped surface 301 (FIGS. 43B and 43C) within the optical member 220, as will be described hereinbelow. An imaginary line 228 (shown to illustrate curvature) delineates the boundary between the proximal section 322 and the central section 324.

Figure 40:
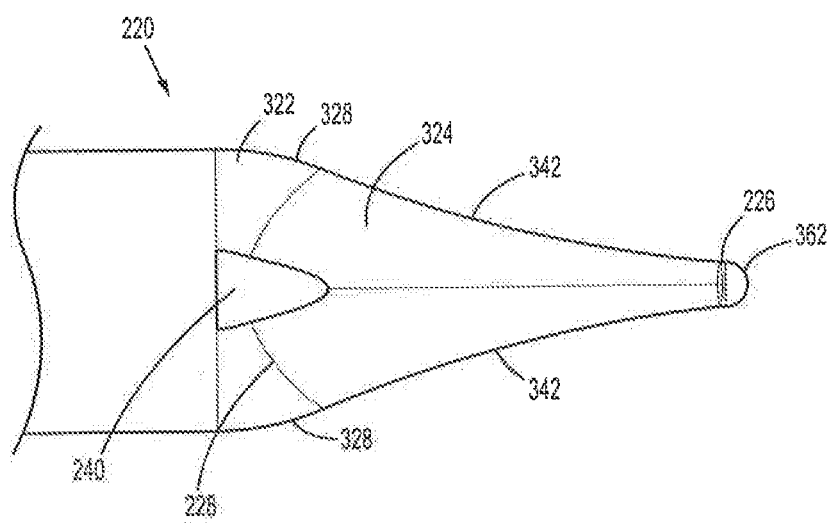
FIG. 40 is a top view of a distal end of the obturator of FIG. 38B.

With reference to FIG. 40, a top view of the optical member 220 is illustrated. As depicted, the proximal section 322 includes a pair of diametrically opposed convex surfaces 328, and the central section 324 includes a pair of diametrically opposed concave surfaces 342. The atraumatic guiding nub 226 extends distally from the central section 324 and includes a rounded end 362. The rounded end 362 defines a radius of curvature dimensioned to be atraumatic to tissue. The guiding nub 226 and the rounded end 362 are discussed in further detail hereinafter.

Figure 41:
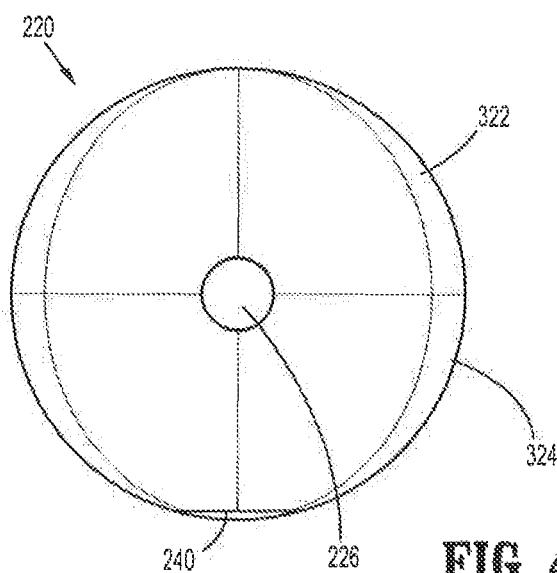
FIG. 41 is a front view of the distal end of the obturator of FIG. 38B.

With reference to FIG. 41, an end or axial view of the optical member 220 illustrates the circular profile of the rounded end 362, the reduced profile of the central section 324, and the circular profile of the proximal section 322.

Figure 42:
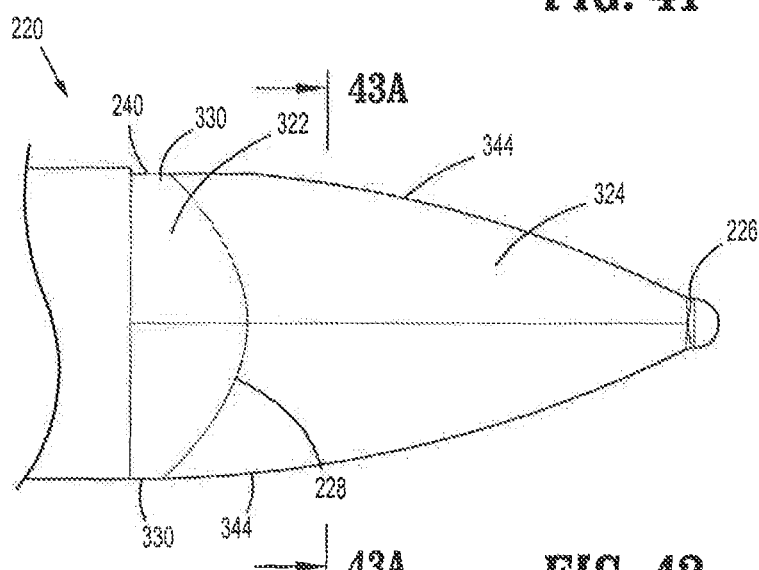
FIG. 42 is a side view of the distal end of the obturator of FIG. 38B.

With reference to FIG. 42, a side view of the optical member 220 is illustrated. This side view is radially offset 90° relative to the top view of FIG. 41. As shown, the proximal section 322 of the optical member 220 further includes a pair of diametrically opposed outer surfaces 330 which are generally linear and/or convex. The central section 324 also includes a pair of opposed outer surfaces 344 which are convex. Thus, the central section 324 of the optical member 220 is inclusive of both concave surfaces 342 (FIG. 40) and convex surfaces 344 (FIG. 42).

Figure 43A:
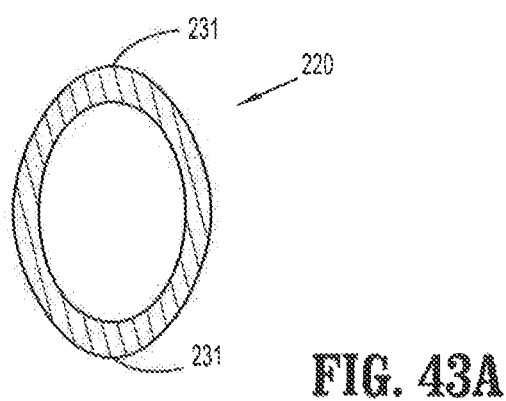
FIG. 43A is a cross-sectional view of the distal end of the obturator of FIG. 38B, taken at approximately the longitudinal midpoint thereof.

FIG. 43A is a cross-sectional view of the optical member 220 taken at approximately the longitudinal midpoint thereof. The figure illustrates that the optical member 220 includes rounded outer surfaces 231 that function to help separate tissue along the natural tissue planes.

The atraumatic guiding nub 226 permits initial insertion within an opening, e.g., a pre-cut scalpel incision, in the tissue and facilitates the advancement of the optical member 220 between the tissue layers to gently dissect tissue, without any cutting or incising of the tissue. After initial insertion and continued distal insertion, the central section 324 and the proximal portion 322 continue to gently enlarge the opening in tissue.

Figure 43B:
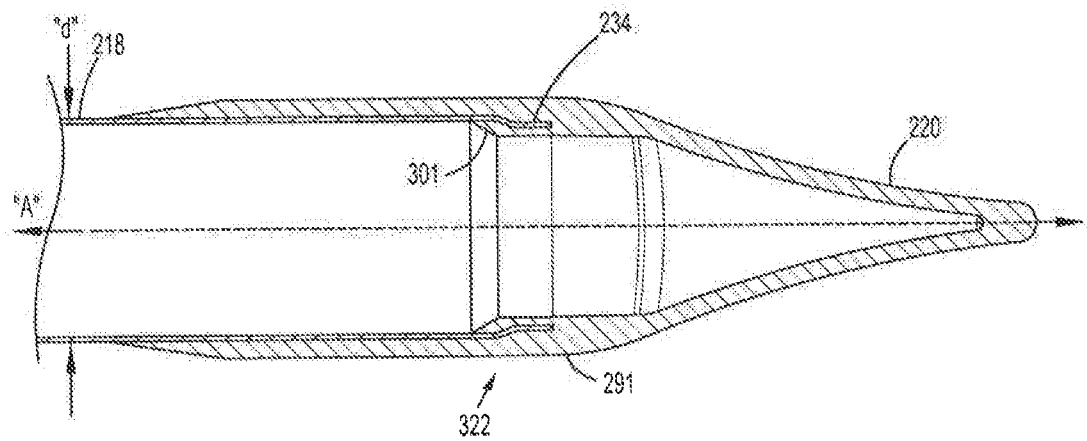
FIG. 43B is a top cross-sectional view of the distal end of the obturator of FIG. 38B.
Figure 43C:
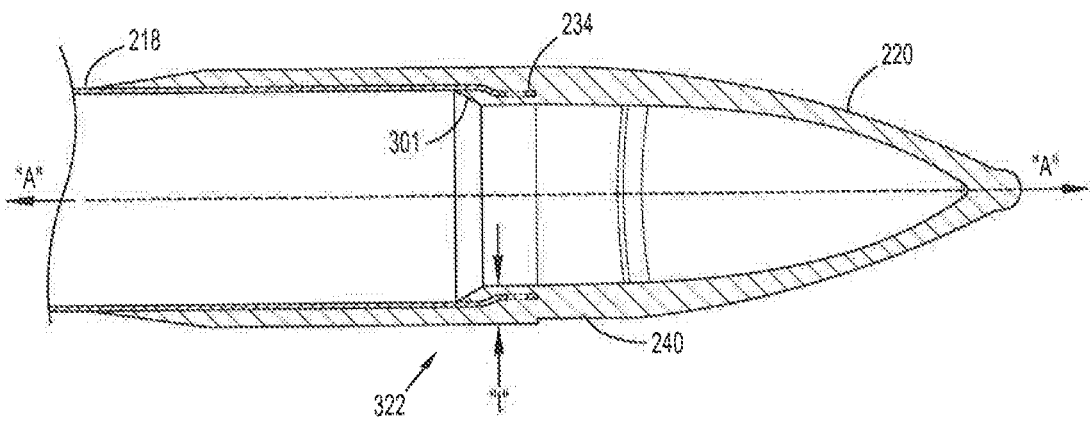
FIG. 43C is a side cross-sectional view of the distal end of the obturator of FIG. 38B.
Figure 43D:
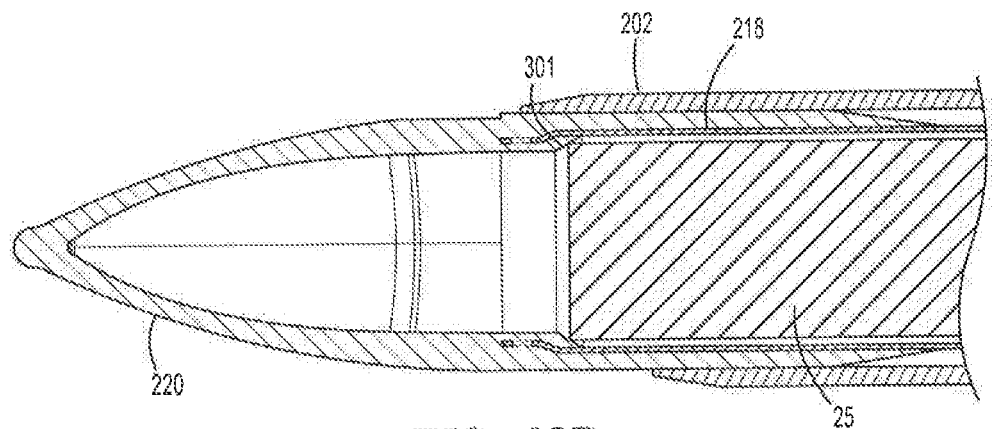
FIG. 43D is a side cross-sectional view of the distal end of the surgical access system of FIG. 38.

With reference to FIGS. 43B and 43C, the optical member 220 may be fabricated from a polymeric or thermoplastic material, and may be transparent or translucent to permit passage of light rays. During assembly, the optical member 220 is overmolded onto a radially outward flared portion 234 of the obturator shaft 218 to connect the components. The overmolded optical member 220 encapsulates flared portion 234.

The optical member 220 defines an internal chamfered or sloped surface 301 which is obliquely arranged relative to the longitudinal axis "A-A." The chamfered surface 301 is directly engaged by the outermost periphery of the distal end of the endoscope 25 (see FIG. 43D) such that light is transmitted radially within the outer periphery of the endoscope 25 and travels across an air gap prior to being received by the chamfered or sloped surface 301. The optical member 220 permits the passage of light rays to enable viewing, with the endoscope 25, of tissue adjacent the optical member 220 during the insertion and/or advancement of the trocar assembly.

As shown above in FIG. 43D, the distal end of the endoscope 25 engages the tapered surface 301 between the proximal and distal ends of the tapered surface 301. The obturator shaft 218 is positioned in a lumen of the elongated portion 202 of the cannula assembly 200. When the distal end of the endoscope 25 is engaged with the tapered surface 301 and the obturator shaft 218 is seated in the elongated portion 202, the distal end of the endoscope 25 is positioned proximally of the distalmost end of the elongated portion 202 of cannula assembly 200 such that the distalmost end of the elongated portion 202 extends beyond the distal end of the endoscope 25.

Figure 43F:
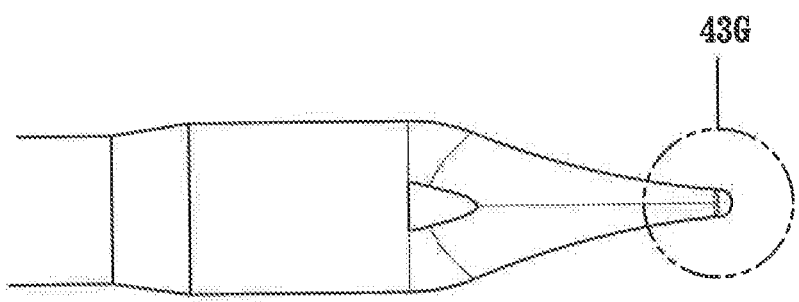

Referring to FIGS. 43E and 43F, a distal portion of the obturator assembly 11 including the optical member 220 is illustrated. The cross-sections taken along lines 1-1 and 2-2 through the proximal section 322 and flat surface 240 are substantially circular. The cross-sections taken along lines 3-3 and 4-4 through the central section 324 have a generally circular or irregular shape with pairs of diametrically opposed rounded outer surfaces 231. Cross-sections taken along lines 5-5, 6-6, 7-7, 8-8, and 9-9, through the central section 324 have a generally oval configuration. The cross-section taken along line 10-10 through the atraumatic guiding nub 226 of the optical member 220 is circular.

Figure 43G:
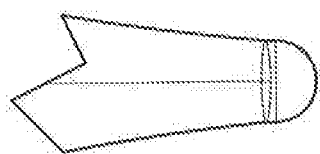
Figure 44:
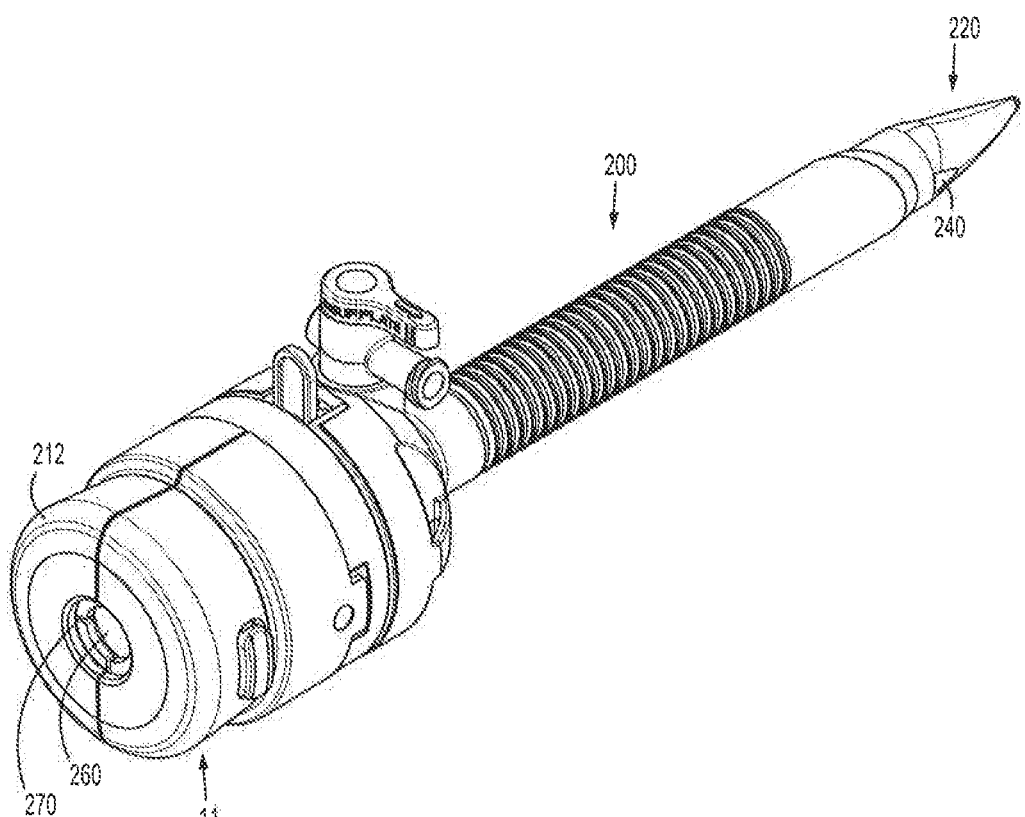
FIG. 44 is a rear perspective view of a surgical access system of FIG. 38B.
Figure 45A:
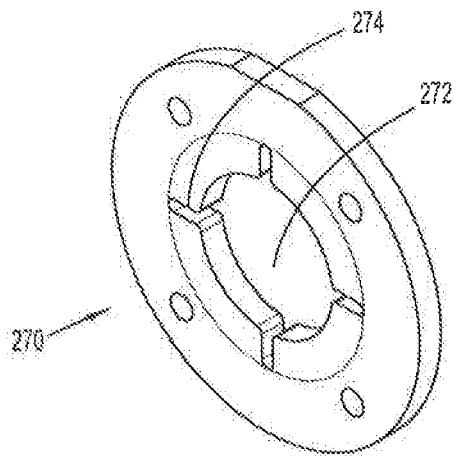
FIG. 45A is a perspective view of a flat elastomeric scope retention mechanism that may be fixed within the proximal housing of the obturator of FIG. 38, the scope retention mechanism depicted in a first configuration with slits.
Figure 45B:
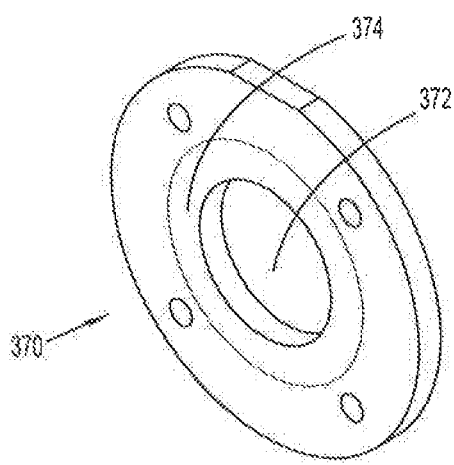
FIG. 45B is a perspective view of a flat elastomeric scope retention mechanism that may be fixed within the proximal housing of the obturator of FIG. 38, the scope retention mechanism depicted in a second configuration without slits.

Referring to FIGS. 43G and 43H, detailed views of the atraumatic guiding nub 226 are illustrated. As shown in FIG. 43H, the cross-sections taken along lines 11-11 and 12-12 through the atraumatic guiding nub 226 are circular with a constant diameter. The cross-section taken along line 13-13 through the central section 324 has a generally oval configuration.

The obturator member 214 is configured for insertion through the cannula assembly 200, as discussed above. The optical member 220 of the obturator assembly 11 is dimensioned such that an outer surface 291 of its proximal portion 322 provides a desired fit within the elongated portion 202 of the cannula assembly 200.

The obturator housing 212 of the obturator assembly 11 includes an opening 260 (FIG. 44) and a scope retention member 270 (FIG. 45A) adjacent the opening 260. The scope retention member 270 may be fabricated from an elastomeric material, and defines a central opening 272 for receiving the endoscope and four radial slits 274 extending outwardly from the central opening 272. The radial slits 274 permit flexure of the scope retention member 270 and enlargement of the central opening 272 upon insertion of the endoscope. The scope retention member 270 is adapted to engage the outer surface of the endoscope in frictional engagement therewith to assist in retaining the relative positioning of the endoscope within the obturator assembly 11 without locking the endoscope in position relative thereto.

In an alternative embodiment, a scope retention member 370 (FIG. 45B) is positioned adjacent the opening 260 of the obturator housing 212 of the obturator assembly 11. The scope retention member 370 may also be fabricated from an elastomeric material, and may define a central opening 372 for receiving the endoscope without any radial slits extending outwardly from the central opening 372. Instead, the central opening 372 is surrounded by a smooth surface 374 having an uninterrupted configuration (i.e., no slits or indentations). The scope retention member 370 is adapted to engage the outer surface of the endoscope in frictional engagement therewith to assist in retaining the relative positioning of the endoscope within the obturator assembly 11 without locking the endoscope in position relative thereto. The scope retention member 370 is capable of functioning as an instrument seal for a wider range of endoscopes or other instrumentation inserted through the central opening 372 (e.g., smaller scope or instrument sizes will also be sealed).

The use and function of system 10 will now be discussed in relation to FIG. 46. In embodiments, in laparoscopic surgery, the abdominal cavity is insufflated with a suitable biocompatible gas such as, e.g., $CO_2$ gas, to insufflate the body cavity and lift the body cavity wall away from the internal organs therein. The insufflation may be performed with an insufflation needle or similar device as is conventional in the art and/or the insufflation gas may be provided through the trocar assembly. In alternative embodiments, system 10 may also be utilized in a space that has not been insufflated.

In use, an initial incision "I" is made in tissue "T" (e.g., skin) by a surgical instrument (e.g., a scalpel). The incision "I" is preferably small, for example, within a range from about 2 mm to about 7 mm. Obturator assembly 11 of surgical access system 10 is at least partially introduced within cannula assembly 100 with obturator member extending through aperture 2166 of septum seal 2160 and through zero-closure seal 250 (see FIG. 6). The assembled unit is positioned within the initial incision and against the target tissue, e.g., the abdominal lining. An endoscope 411 may be inserted through obturator assembly 11 such that the distal viewing end of endoscope 411 is positioned against the chamfered surface of optical member 20. Endoscope 411 may be retained at this relative position within obturator assembly 11 by scope retention member 170.

During insertion, the tissue adjacent optical member 20 is viewed with endoscope 411. During advancement of system 10, endoscope 411 is utilized to view the path along which the system is advanced to ensure that any underlying tissue or organ site is prevented from contact with obturator assembly 11 and also to confirm entry within the body cavity.

Figure 46:
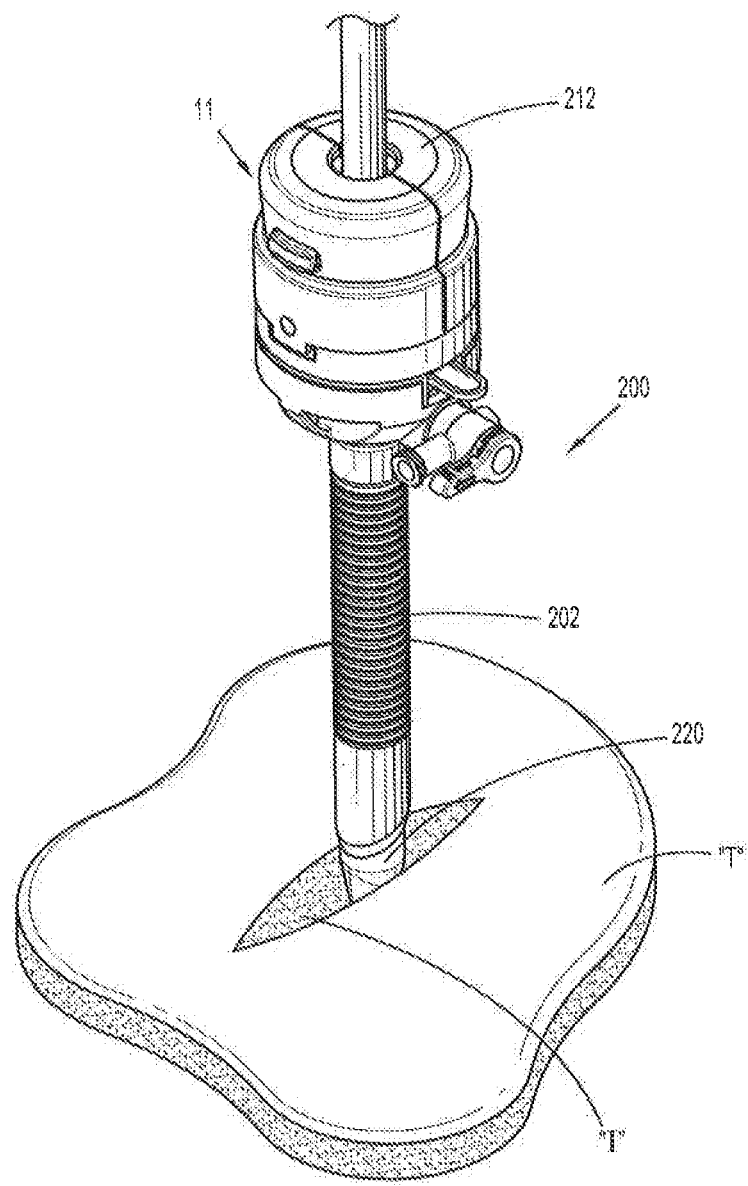
FIG. 46 is a perspective view of the surgical access system in use within an incision and having an endoscope inserted therein, in accordance with an embodiment of the present invention.

Once system 10 is positioned at the desired location, as shown in FIG. 46, endoscope 411 may be used to monitor the desired surgical procedure being performed within the cavity. Obturator assembly 11 may then be removed from cannula assembly 100. Instruments, such the same endoscope of various other types of instruments, may be introduced within cannula assembly 100 to perform a surgical procedure.

Figure 48:
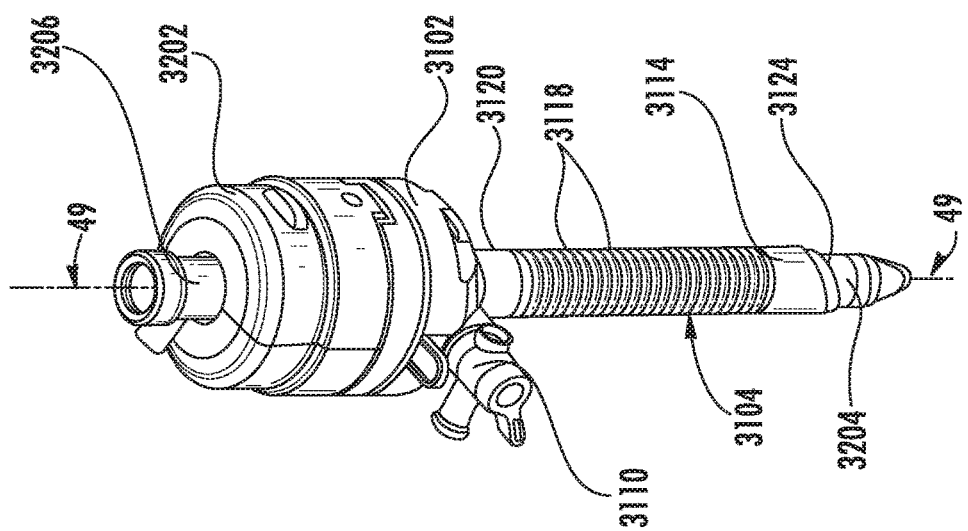
FIG. 48 is a perspective view of the surgical access system of FIG. 47 with the obturator assembly mounted to the cannula assembly.
Figure 47:
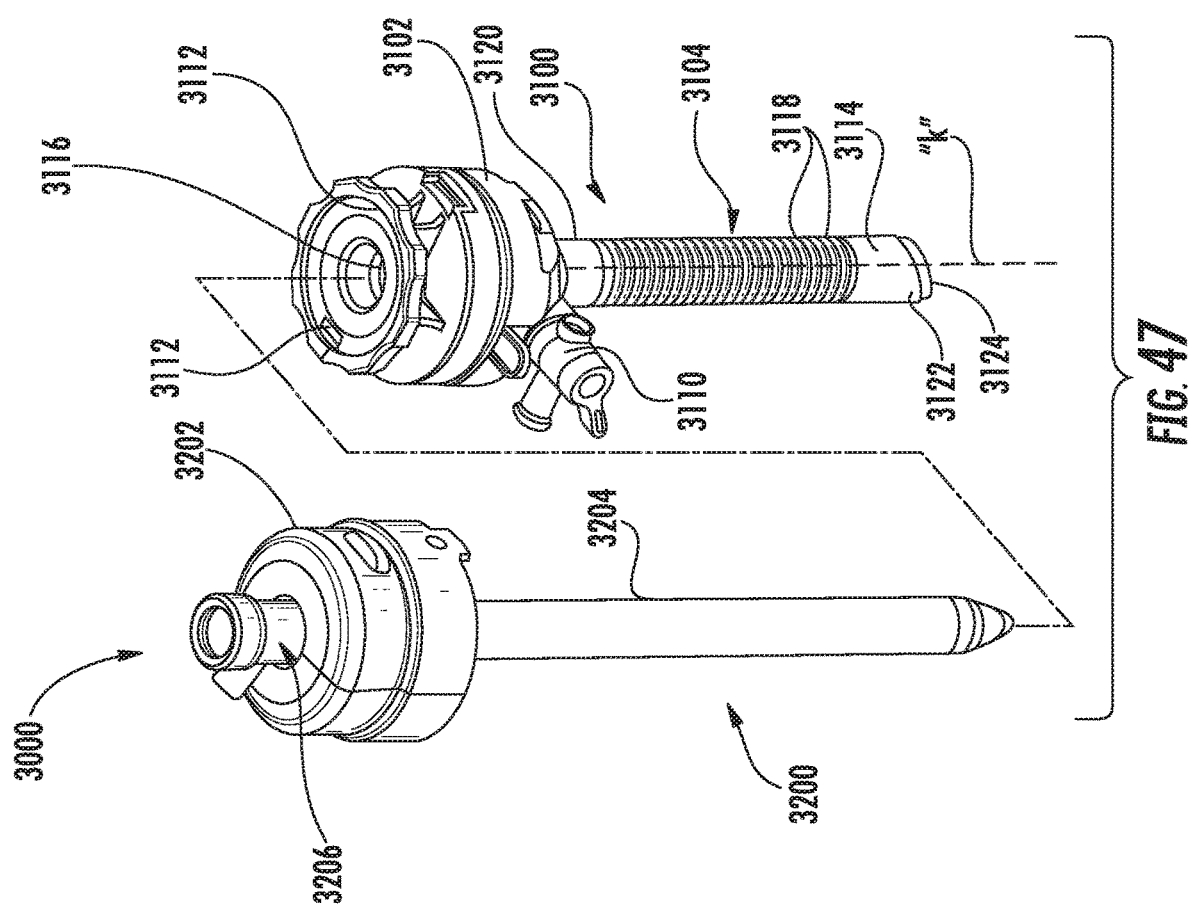
FIG. 47 is an perspective view of a surgical access system in accordance with another embodiment of the present disclosure illustrating the cannula assembly and the obturator assembly.
Figure 49:
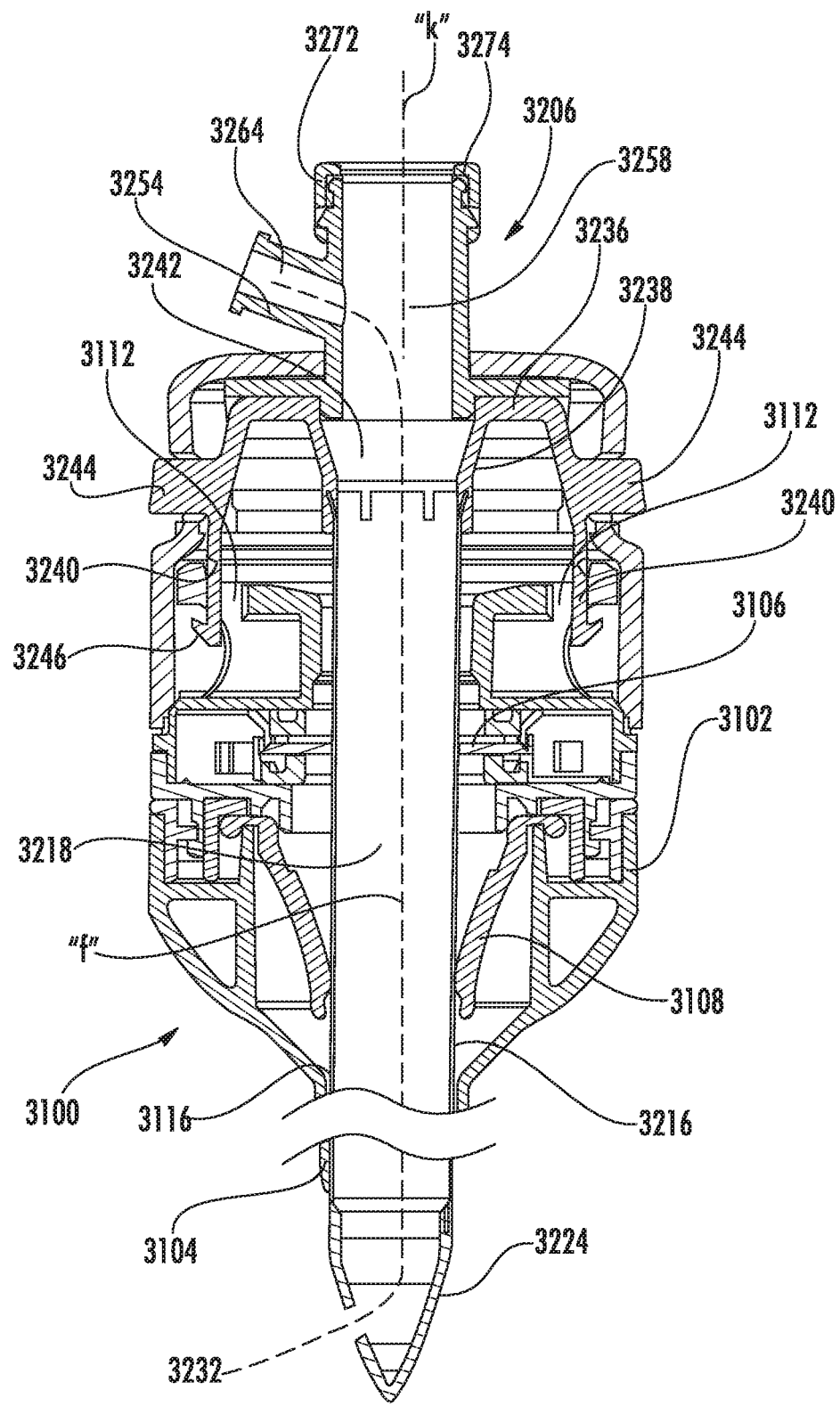
FIG. 49 is a side cross-sectional view of the access system.
Figure 50:
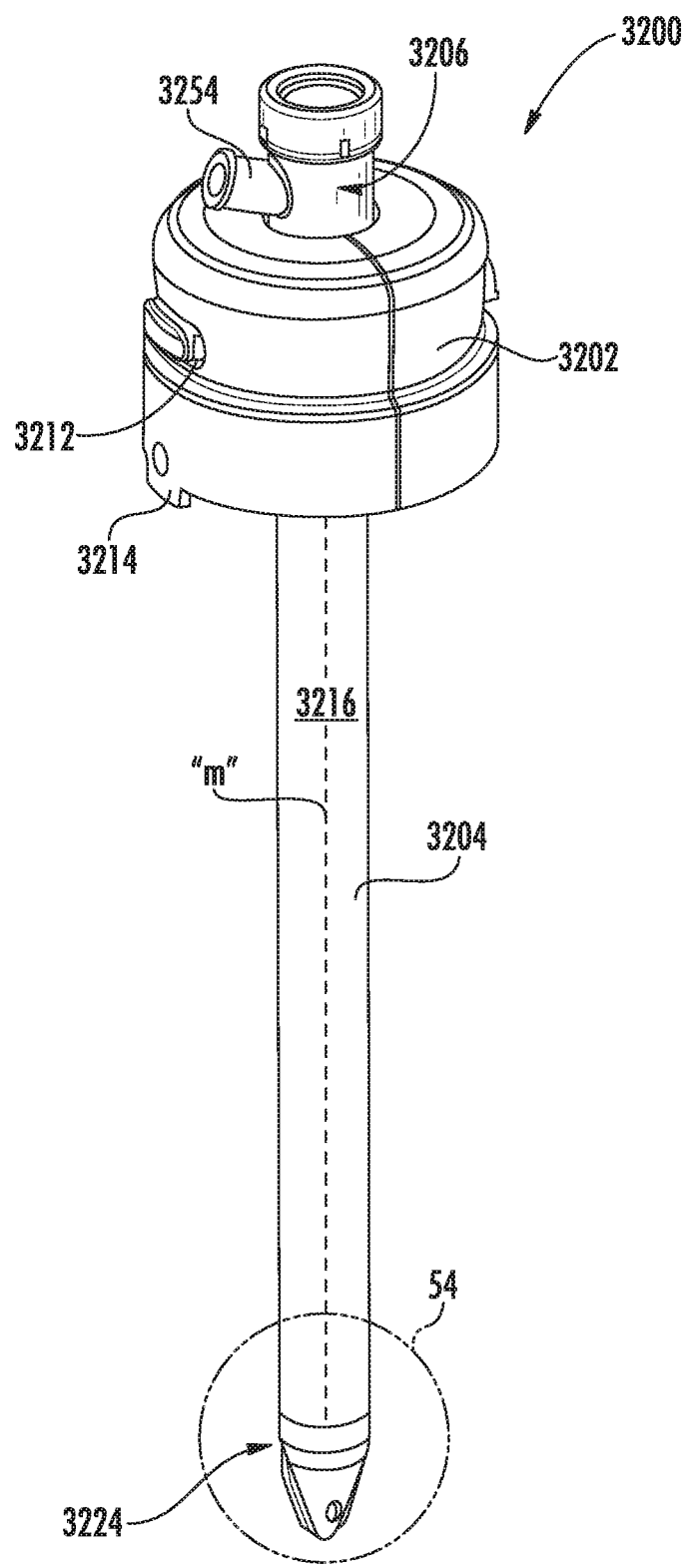
FIG. 50 is a perspective view of the obturator assembly of the access system.

Referring now to FIGS. 47-49, another embodiment of the access system is illustrated. The access system 3000 includes a cannula assembly 3100 and an obturator assembly 3200 which is at least partially positionable within the cannula assembly 3100. The cannula assembly 3100 includes a cannula housing 3102 and a cannula member 3104 extending from the cannula housing 3102. As best depicted in FIG. 49, the cannula housing 3102 may include at least one internal seal 3106 for establishing a sealing relationship about a surgical object introduced therein, and may further include a zero closure valve 3108 adapted to close in the absence of the surgical object and/or in response to an underlying pressurized environment, e.g., an insufflated abdominal cavity, to prevent exit of insufflation fluids through the cannula assembly 3100. The cannula housing 3102 may further include a stopcock valve 3110 for coupling to a source of insufflation fluids for passage through the cannula member 3104 and into the underlying tissue to maintain/establish the insufflated state of the abdominal cavity. The cannula housing 3102 includes a pair of diametrically opposed openings 3112 which assists in mounting the obturator assembly 3200 relative to the cannula assembly 3100.

The cannula member 3104 of the cannula assembly 3100 includes a cannula wall 3114 extending along a longitudinal cannula axis "k" and defining a cannula lumen 3116 for at least partial reception of the obturator assembly 3200. The cannula wall 3114 may include a plurality of ribs 3118 to facilitate engagement with tissue to secure the cannula assembly 3100 relative to the underlying tissue site. The cannula member 3104 included a proximal end segment 3120 coupled to the cannula housing 3102 through conventional methodologies and a distal end segment 3122 which may define an entry end 3124 obliquely arranged relative to the longitudinal axis "k" to facilitate entry of the cannula member 3104 within the tissue site.

Referring now to FIGS. 49-53, the obturator assembly 3200 will be discussed. The obturator assembly 3200 includes an obturator housing 3202, an obturator member 3204 mounted to the obturator housing 3202 and extending distally therefrom, and a cap 3206 which is coupled to the obturator housing 3202. The obturator assembly 3200 may further include a connector 3208 (FIG. 51) to assist in securing the cap 3206 relative to the obturator housing 3202 and to the obturator member 3204. The obturator housing 3202 includes housing half sections 3210 secured to each other through conventional methodologies. The housing half sections 3210 each define an aperture 3212 extending through its respective walls with the apertures 3212 being arranged in diametrical opposed relation. The obturator housing 3202 may further include a pair of detents 3214 extending distally in a longitudinal direction adjacent the obturator member 3204. The detents 3214 rotatably fix the obturator assembly 3200 relative to the cannula assembly 3100 when in the assembled condition of the components.

Figure 51:
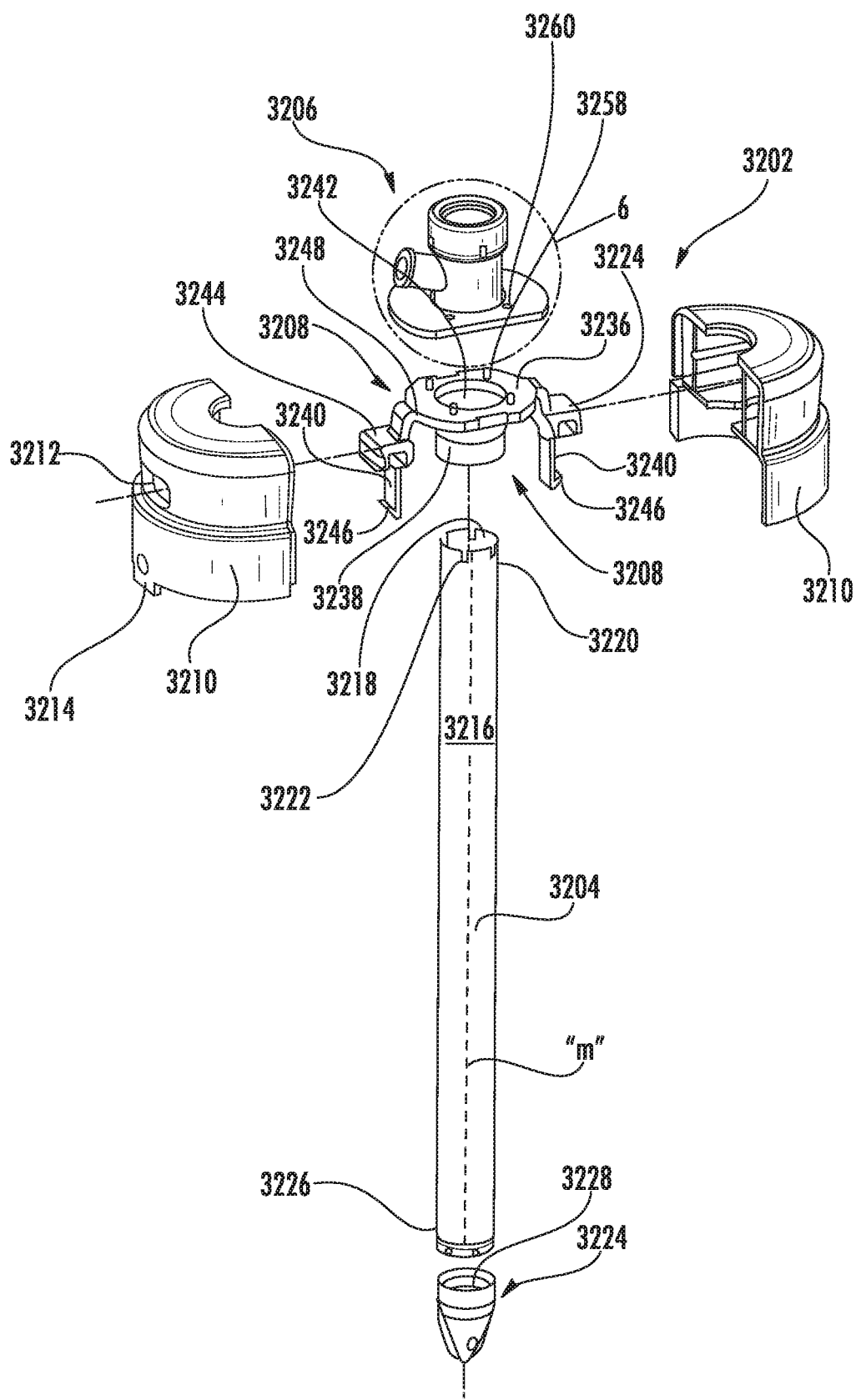
FIG. 51 is an exploded perspective view of the obturator assembly illustrating the obturator housing, the obturator member and the cap.

As best depicted in FIGS. 51-53, the obturator member 3204 defines a longitudinal obturator axis "m" which is in general alignment with the longitudinal cannula axis "k" of the cannula assembly 3100. The obturator member 3204 includes an obturator wall 3216 defining an obturator lumen 3218 extending along the obturator axis "m". The proximal end segment 3220 of the obturator wall 3216 may include a plurality of mounting elements 3222 to facilitate securement of the obturator member 3204 relative to the connector 3208 and the obturator housing 3202. In the alternative, the obturator wall 3216 may be devoid of the mounting elements 3222. The obturator wall 3216 of the obturator member 3204 is continuous, i.e., there are no apertures, openings or perforations extending through the obturator wall 3216.

Figure 54:
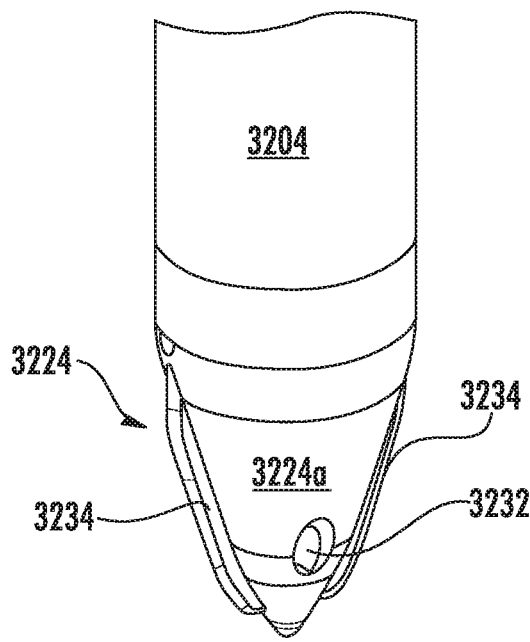
FIG. 54 is an enlarged isolated view of the area of detail depicted in FIG. 50.

With reference to FIGS. 52-54, a penetrating member 3224 is mounted to the distal end segment 3226 of the obturator wall 3216 via conventional mechanisms including, e.g., adhesives, cements, snap-fit mechanisms or the like. Alternatively, the penetrating member 3224 may be monolithically formed with the obturator wall 3216. The penetrating member 3224 defines a hollow cavity 3228 which terminates in a closed penetrating end 3230. As best depicted in FIG. 54, at least one fluid opening or aperture 3232 extends through the wall 3224a of the penetrating member 3224 in communication with the hollow cavity 3228, which, in turn, is in fluid communication with the obturator lumen 3218. More than one aperture 3232 is also contemplated. The aperture 3232 is defined at least in part by proximal and distal surface portions 3232p, 3232d of the penetrating member 3224. These surface portions 3232p, 3232d are obliquely arranged relative to the longitudinal axis "m". The oblique arrangement will minimize the potential of coring of tissue by the aperture 3232 during entry into, e.g., the abdominal cavity. The penetrating member 3224 may include a pair of diametrically opposed ribs 3234 to facilitate passage through tissue. The penetrating member 3224 includes in whole, or in part, a transparent material to permit visualization through the penetrating member 3224 with a viewing device such as an endoscope or a laparoscope.

With reference again to FIGS. 51-52, the connector 3208 includes a connector base 3236, a connector wall 3238 extending from the connector base 3236 and a pair of diametrically opposed mounting legs 3240 extending radially outwardly and longitudinally relative to the connector base 3236. The connector base 3236 and the connector wall 3238 define a connector lumen 3242 in general alignment with the obturator lumen 3218 and with the obturator axis "m". The connector wall 3238 is mounted to the proximal end segment 3220 of the obturator wall 3216. In one embodiment, the obturator member 3204 is positioned within the connector wall 3238 and retained therein by the mounting elements 3222 which may be spring-biased radially outwardly to engage the inner wall surface of the connector wall 3238. In addition, or alternatively, conventional methodologies including adhesives, cements or the like may be utilized to secure the connector 3208 to the obturator member 3204.

The mounting legs 3240 of the connector 3208 each include a manually engageable tab 3244 disposed along an intermediate portion of the mounting leg 3240 and a mounting ledge 3246 at the distal end of the mounting leg 3240. The manually engageable tabs 3244 are received within the apertures 3212 of the obturator housing 3202. The mounting legs 3240 are mounted for slight pivotal movement relative to the connector base 3236 about living hinges 3248 through radial inward and outward movement of the manually engageable tabs 3244 to cause corresponding deflection of the mounting ledges 3246. This movement causes corresponding release or engagement of the obturator housing 3202 relative to the cannula housing 3102 through engagement of the mounting legs 3240 with the diametrically opposed openings 3112 of the cannula housing 3102 (FIG. 49).

Figure 55:
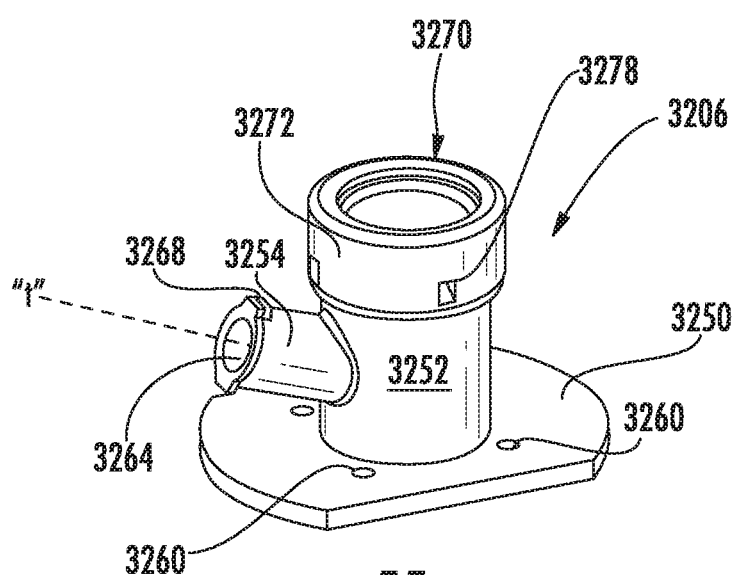
FIG. 55 is a perspective view of the cap of the obturator assembly.
Figure 56:
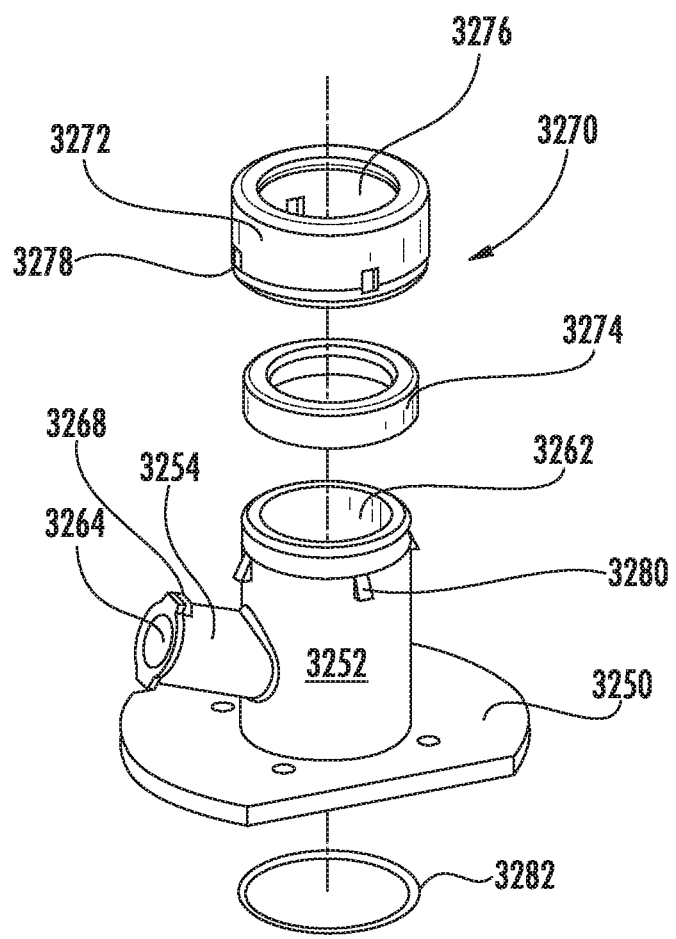
FIG. 56 is an exploded perspective view of the cap.

Referring now to FIGS. 55-56, the cap 3206 will be discussed. The cap 3206 includes a cap base 3250, a cap wall 3252 depending longitudinally from the cap base 3250 and an insufflation port 3254 depending radially outwardly relative to the cap wall 3252. The cap base 3250 is secured to the connector 3208 through conventional mechanisms. In one embodiment, the connector base 3236 of the connector 3208 includes a plurality of split rivets 3258 (FIG. 51) which are received within corresponding apertures 3260 of the cap base 3250. The cap wall 3252 defines a cap lumen 3262 in longitudinal alignment with the obturator lumen 3218. The insufflation port 3254 defines a port channel 3264 arranged about a port axis "t" in oblique relation to the longitudinal obturator axis "m" and in fluid communication with the cap lumen 3262 and, thus the obturator lumen 3218. The oblique relation of the insufflation port 3254 facilitates directing of the insufflation fluids toward the obturator lumen 3218. The insufflation port 3254 includes a luer connector 3268 or the like for coupling to tubing of an insufflation source.

The cap 3206 further includes a scope or instrument retention assembly 3270 having a retention mount 3272 and a retention member 3274 couplable to the retention mount 3272. In one embodiment, the retention mount 3272 is generally annular shaped defining a central mount passage 3276 in general alignment with the obturator lumen 3218. The retention mount 3272 may include a plurality of mounting recesses 3278 which receive mounting tabs 3280 of the cap 3206 to connect the retention mount 3272 to the cap 3206 whereby the retention member 3274 is secured between the retention mount 3272 and a proximal ledge of the cap wall 3252 (FIG. 53). The retention member 3274 may be an elastomeric gasket configured to frictionally engage a viewing device, such as a laparoscope, or other instrumentation to assist in retaining the viewing device at a predetermined position relative to the obturator assembly 3200 and/or the cannula assembly 3100. The cap 3206 may further include an O-ring seal 3282 adjacent the cap base 3250, which engages an inner surface of the connector wall 3238 of the connector 3208 to establish a seal between the cap 3206 and the connector 3208.

Referring again to FIG. 49, the isolated fluid passage provided by the aforedescribed components of the obturator assembly 3200 will be discussed. The fluid passage "f" is inclusive of the cap lumen 3262 of the cap 3206, the connector lumen 3242 of the connector 3208 and the obturator lumen 3218 of the obturator member 3204. The fluid passage "f" is completely isolated from the cannula lumen 3116. In particular, insufflation fluids introduced through the insufflation port 3254 of the cap 3206 pass within its port channel 3264, through the fluid passage "f" to exit the aperture 3232 (shown in phantom) in the penetrating member 3224 without entering the cannula lumen 3116, i.e., the insufflation fluids flow directly through the fluid passage "f" independent of the cannula lumen 3116 and are released through the aperture 3232 of the penetrating member 3224 distal of the cannula member 3104. Thus, during insertion of the access system 3000 through tissue to access an underlying cavity, e.g., the abdominal cavity, the potential for insufflation fluids within the flow passage "f" to migrate into or between layers of tissue is substantially minimized thereby reducing the risk of developing a subcutaneous emphysema. This obviates the risk associated with the conventional insufflation trocars utilizing both a lumen of the obturator and the cannula as part of the path for passage of insufflation fluid.

Figure 57:
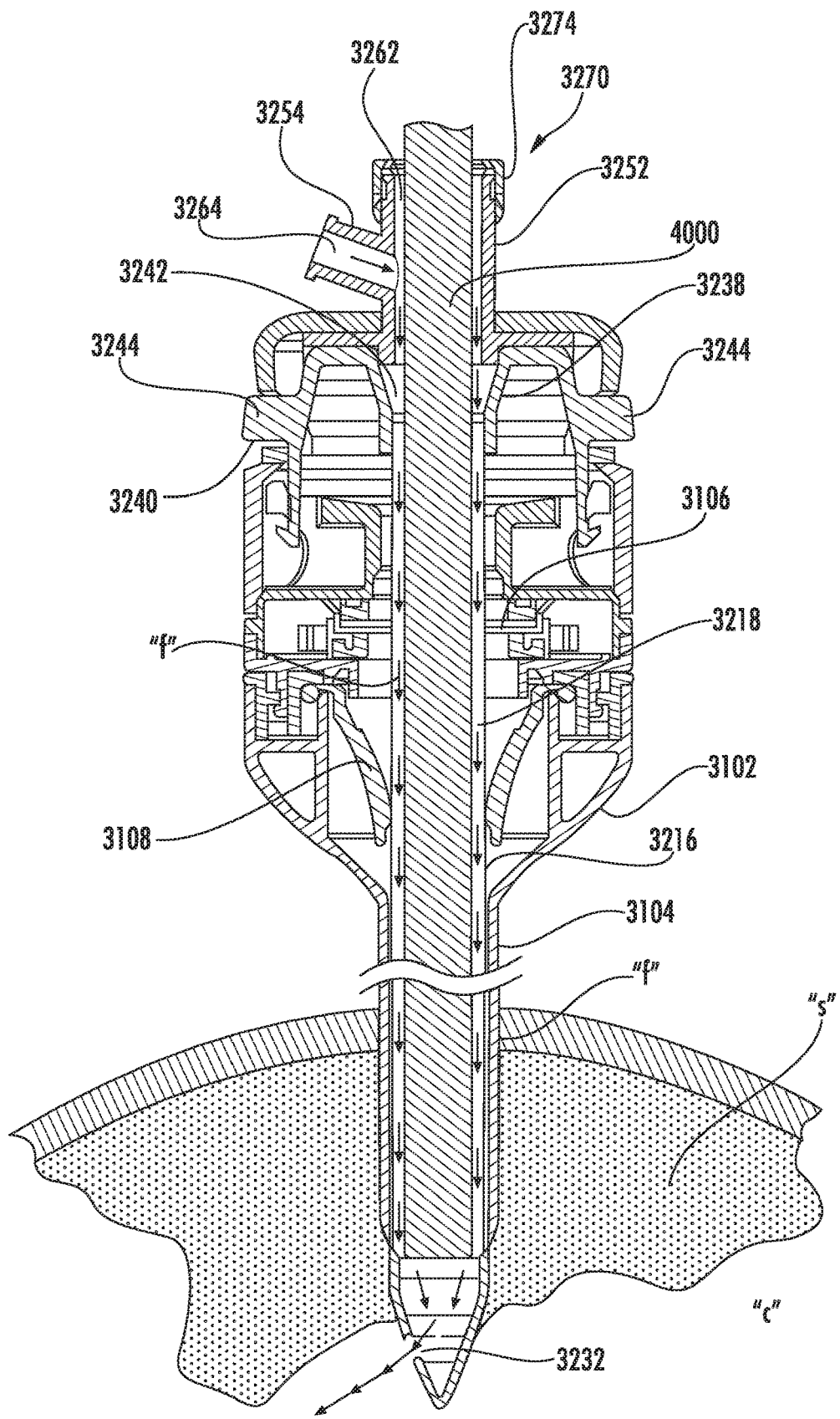
FIG. 57 is a view illustrating a viewing device positioned within the access system with the access system passing through abdominal tissue surrounding an abdominal cavity.

FIG. 57 illustrates a viewing device 4000 such as a laparoscope positioned within the access system 3000, and being advanced through tissue "s" to access an underlying cavity "c". The viewing device 4000 permits visualization through the penetrating member 3224 of the obturator assembly 3200 as the access system 3000 is advanced thereby aiding the clinician in positioning and placement of the access system 3000 while minimizing the potential of piercing underlying tissue and/or organs. The viewing device 4000 is introduced through the cap lumen 3262 of the cap 3206 and advanced into the obturator lumen 3218 of the obturator member 3204. As discussed hereinabove, the viewing device 4000 may be secured relative to the obturator assembly 3200 by the retention member 3274 mounted within the cap 3206.

During insertion of the access system 3000, insufflation fluids may be introduced through the obturator assembly 3200 to inflate the underlying body cavity, e.g., the abdominal cavity "c". The insufflation fluids are introduced through the insufflation port 3254 of the cap 3206 and pass along the fluid passage "f" (directional arrows) within the obturator assembly 3200, e.g., within the annular space defined between the outer surface of the viewing device 4000, and the cap wall 3252 of the cap 3206, the connector wall 3238 of the connector 3208 and the obturator wall 3216 of the obturator member 3204, to exit out the penetrating member 3224 of the obturator assembly 3200 to insufflate the abdominal cavity "c". The insufflation fluids are directed distal of the cannula member 3104 thereby minimizing the potential of the fluids being trapped between the cannula member 3104 and the obturator member 3204 which may be deleterious to the abdominal tissue layers for reasons discussed hereinabove. Once the access system 3000 is positioned at the desired location, the viewing device 4000 and the obturator assembly 3200 may be removed from the cannula assembly 300 leaving the cannula assembly 3100 accessing the cavity "c'. Instruments or other viewing devices may be introduced within the cannula assembly 3100 to perform one or more surgical tasks.

While various embodiments of the present disclosure have been shown and described herein, it will be obvious to those skilled in the art that these embodiments are provided by way of example only. Numerous variations, changes, and substitutions will now occur to those skilled in the art without departing from the present disclosure. Accordingly, it is intended that the disclosure be limited only by the spirit and scope of the appended claims.

The invention claimed is:

1. A surgical access system, which comprises:
  a cannula assembly including a cannula housing and a cannula member extending from the cannula housing, the cannula housing including a first insufflation port extending laterally therefrom, the cannula member defining a longitudinal axis and having proximal and distal ends, the cannula member including a cannula wall defining a cannula lumen; and
  an obturator assembly including:
    an obturator housing;
    an obturator member extending from the obturator housing and at least partially positionable within the cannula lumen, the obturator member including an obturator wall having a penetrating member configured for penetrating tissue, the obturator wall having at least one fluid opening therethrough;
    a cap mounted to the obturator housing, the cap and the obturator member defining a fluid passage extending along the longitudinal axis to the penetrating member, the fluid passage isolated from the cannula lumen; and
    a second insufflation port mounted to the cap and defining a port channel in fluid communication with the fluid passage such that insufflation fluids introduced within the port channel are conveyed through the fluid passage and exit the at least one fluid opening independent of the cannula lumen.

2. The surgical access system according to claim 1 wherein the penetrating member includes the at least one fluid opening.

3. The surgical access system according to claim 2 wherein the at least one fluid opening of the penetrating member is disposed beyond the distal end of the cannula member when the obturator member is positioned within the cannula lumen.

4. The surgical access system according to claim 2 wherein the at least one fluid opening is defined at least in part by proximal and distal surfaces of the penetrating member, the proximal and distal surfaces obliquely arranged relative to the longitudinal axis and configured to minimize the potential of coring of tissue by the at least one fluid opening during passage through tissue.

5. The surgical access system according to claim 3 wherein at least the penetrating member of the obturator wall includes a transparent material.

6. The surgical access system according to claim 5 wherein the cap includes a cap wall defining a cap lumen, the fluid passage including the cap lumen.

7. The surgical access system according to claim 6 wherein the obturator wall defines an obturator lumen, the fluid passage including the obturator lumen.

8. The surgical access system according to claim 7 wherein the cap lumen and the obturator lumen are configured to receive a surgical instrument.

9. The surgical access system according to claim 8 wherein the cap includes an instrument retention member configured for engaging the surgical instrument, to facilitate retention of the instrument at a predetermined position within the obturator member.

10. The surgical access system according to claim 9 wherein the instrument retention member includes a friction washer configured to frictionally engage the surgical instrument.

11. The surgical access system according to claim 10 wherein the instrument retention member is configured to engage a laparoscope.

12. The surgical access system according to claim 1 wherein the second insufflation port is arranged about a port axis in oblique relation to the longitudinal axis to facilitate directing of the insufflation fluids toward the fluid passage.

13. The surgical access system according to claim 1 wherein the cap is secured to the elongate obturator member and the obturator housing by a connector having mounting legs.

14. A surgical obturator assembly, which comprises:
an obturator housing having a first insufflation port;
an elongate obturator member defining a longitudinal obturator axis and proximal and distal ends, the obturator member distally extending from the obturator housing and being configured for at least partial introduction within a cannula, the obturator member including an obturator wall defining an obturator lumen and having a penetrating member, the penetrating member terminating in a closed penetrating end configured for penetrating tissue, the penetrating member having at least one fluid opening therethrough;
a cap mounted to the obturator housing, the cap including a cap lumen in longitudinal alignment with the obturator lumen, the cap lumen and the obturator lumen configured for reception of a laparoscope, and defining an isolated fluid passage extending along the longitudinal axis to the penetrating member; and
a second insufflation port mounted to the cap proximal of the obturator housing and defining a port channel in fluid communication with the fluid passage such that insufflation fluids introduced within the port channel are conveyed through the fluid passage and exit the at least one fluid opening of the penetrating member.

15. The surgical obturator assembly according to claim 14 wherein at least the penetrating member of the obturator wall includes a transparent material.

16. The surgical obturator assembly according to claim 14 wherein the cap includes a scope retention member configured for engaging the laparoscope to facilitate retention of the laparoscope at a predetermined position within the obturator member.

17. The surgical obturator assembly according to claim 16 wherein the scope retention member is configured to establish a sealing relationship with the laparoscope.

18. The surgical obturator assembly according to claim 14 wherein the at least one fluid opening is disposed in fluid communication with a hollow cavity within the penetrating member, the hollow cavity defined by the closed penetrating end.

19. The surgical obturator assembly according to claim 14 wherein the obturator housing includes a first section and a second section that is separate and discrete from the first section, the first and second sections positioned to capture the cap within the first and second sections.

20. A surgical access system, which comprises:
a cannula assembly including a cannula housing and a cannula member extending from the cannula housing, the cannula housing including a first insufflation port; and
an obturator assembly including:
an obturator housing;
an obturator member extending from the obturator housing, the obturator member including an obturator wall having a penetrating member configured for penetrating tissue, the obturator wall having at least one fluid opening therethrough;
a cap mounted to the obturator housing, the cap and the obturator member defining a fluid passage; and
a second insufflation port mounted to the cap and defining a port channel in fluid communication with the fluid passage such that insufflation fluids introduced within the port channel are conveyed through the fluid passage and exit the at least one fluid opening.

* * * * *